(12) United States Patent
Bhushan et al.

(10) Patent No.: US 11,749,437 B2
(45) Date of Patent: Sep. 5, 2023

(54) PUMPS AND HARDWARE FOR ORGAN-ON-CHIP PLATFORMS

(71) Applicant: Massachusetts Institute of Technology, Cambridge, MA (US)

(72) Inventors: Brij Mohan Bhushan, Cambridge, MA (US); Daniel R. Rathbone, Somerville, MA (US); David L. Trumper, Plaistow, NH (US); Minkyun Noh, Cambridge, MA (US); Jun Young Yoon, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1006 days.

(21) Appl. No.: 16/400,840

(22) Filed: May 1, 2019

(65) Prior Publication Data
US 2019/0338230 A1 Nov. 7, 2019

Related U.S. Application Data

(60) Provisional application No. 62/665,348, filed on May 1, 2018.

(51) Int. Cl.
*H01F 7/14* (2006.01)
*B01L 3/00* (2006.01)
(Continued)

(52) U.S. Cl.
CPC ............ *H01F 7/14* (2013.01); *B01L 3/50273* (2013.01); *B01L 3/502707* (2013.01);
(Continued)

(58) Field of Classification Search
CPC ......... B01L 2200/025; B01L 2200/027; B01L 2200/10; B01L 2300/123;
(Continued)

(56) References Cited

U.S. PATENT DOCUMENTS

| 5,468,605 | A | 11/1995 | Harris |
| 6,103,199 | A | 8/2000 | Bjornson |

(Continued)

FOREIGN PATENT DOCUMENTS

| CN | 103672016 | 3/2014 |
| CN | 107659208 | 2/2018 |

(Continued)

OTHER PUBLICATIONS

Espacenet English Translation of CN103672016. (Year: 2014).*

(Continued)

*Primary Examiner* — Christine T Mui
*Assistant Examiner* — Kathryn Elizabeth Limbaugh
(74) *Attorney, Agent, or Firm* — PABST PATENT GROUP LLP

(57) ABSTRACT

On-platform pumps provide greater flexibility and design freedom and are a key feature of organs-on-chip platforms. On-platform electromagnetic (EM) pumps have been developed for use with the organ-on-chip platforms. The EM pump uses electrical energy, which may be supplied by a battery, making the pump portable. The EM pump uses an EM actuator having a low energy consumption. The actuator's low energy consumption is achieved by a latching design which requires only a short pulse of energy to switch its state and where springs store some of the actuator kinetic energy, which is then recovered in the reverse stroke. This further reduces the energy consumption of the actuator. Also provided are injection-molded, single-use platforms with onboard diaphragm micro-pumps and various valve and pump geometries. The EM actuators easily integrate with these platforms, demonstrating pumping at a constant flow-rate, no measurable temperature rise, and valve sealing against varying back-pressure.

36 Claims, 46 Drawing Sheets

(51) Int. Cl.

| | |
|---|---|
| *B01L 9/00* | (2006.01) |
| *C12M 3/00* | (2006.01) |
| *C12M 3/06* | (2006.01) |
| *C12M 1/00* | (2006.01) |
| *F04B 43/04* | (2006.01) |
| *F04B 43/14* | (2006.01) |

(52) U.S. Cl.
CPC ... *B01L 3/502715* (2013.01); *B01L 3/502753* (2013.01); *B01L 9/527* (2013.01); *C12M 21/08* (2013.01); *C12M 23/16* (2013.01); *C12M 29/00* (2013.01); *F04B 43/043* (2013.01); *F04B 43/14* (2013.01); *B01L 2200/025* (2013.01); *B01L 2200/027* (2013.01); *B01L 2200/10* (2013.01); *B01L 2300/123* (2013.01); *B01L 2400/043* (2013.01); *B01L 2400/0415* (2013.01)

(58) Field of Classification Search
CPC ....... B01L 2400/0415; B01L 2400/043; B01L 3/502715; B01L 3/50273; B01L 3/502753; B01L 9/527; C12M 21/08; C12M 23/16; C12M 29/00; F01B 43/043; F01B 43/14; H01F 7/122; H01F 7/14; H01F 7/1646
See application file for complete search history.

(56) References Cited

U.S. PATENT DOCUMENTS

| | | | |
|---|---|---|---|
| 6,197,575 | B1 | 3/2001 | Griffith |
| 8,318,479 | B2 | 11/2012 | Domansky |
| 9,588,105 | B1 | 3/2017 | Hussain |
| 2004/0228770 | A1 | 11/2004 | Gandhi |
| 2005/0238506 | A1 | 10/2005 | Mescher |
| 2005/0244932 | A1 | 11/2005 | Harding |
| 2005/0260745 | A1 | 11/2005 | Domansky |
| 2008/0032380 | A1 | 2/2008 | Kleis |
| 2008/0170936 | A1* | 7/2008 | Den Toonder .... B01L 3/502746 137/13 |
| 2010/0230613 | A1 | 9/2010 | Pieprzyk |
| 2013/0068310 | A1 | 3/2013 | Sip |
| 2014/0196550 | A1 | 7/2014 | Chernomorsky |
| 2014/0354381 | A1* | 12/2014 | Kohlhafer ............. H01H 50/20 335/179 |
| 2016/0151778 | A1 | 6/2016 | McClelland |
| 2016/0326477 | A1* | 11/2016 | Fernandez-Alcon ........................ B01D 63/081 |
| 2016/0377599 | A1 | 12/2016 | Hughes |
| 2017/0227525 | A1 | 8/2017 | Griffith |

FOREIGN PATENT DOCUMENTS

| | | |
|---|---|---|
| GB | 2147100 | 5/1985 |
| WO | 2005123950 | 12/2005 |
| WO | 2011071772 | 6/2011 |
| WO | 2015003997 | 1/2015 |

OTHER PUBLICATIONS

Espacenet English Translation of CN107659208. (Year: 2018).*
Anna, "Droplets and Bubbles in Microfluidic Devices", Annu. Rev. Fluid Meeh. 48:285-309 (2016).
Cook, et al., "Lessons learned from the fate of AstraZeneca's drug pipeline: a five-dimensional framework", Nat Rev Drug Discov, 13(6):419-31 (2014).
Denayer, et al., "Animal models in translational medicine: Validation and prediction", New Horizons in Translational Medicine, 2(1):5-11 (2014).
Domansky, et al., "Perfused Multiwell Plate for 3D Liver Tissue Engineering", Lab Chip, 10(1):51-8 (2010).
Esch, et al., "Body-on-a-Chip Simulation with Gastrointestinal Tract and Liver Tissues Suggests that Ingested Nanoparticles Have the Potential to Cause Liver Injury", Lab Chip, 14(16):3081-92 (2014).
Halldorsson, et al., "Advantages and challenges of microfluidic cell culture in polydimethylsiloxane devices", Biosens. Bioelectron., 63:218-31 (2015).
Huebsch, et al., "Miniaturized iPS-Cell-Derived Cardiac Muscles for Physiologically Relevant Drug Response Analyses", Scientific Reports, 6:24726 (2016).
Huh, et al., "Microengineered physiological biomimicry: organs-on-chips", Lab Chip, 12(12):2156-64 (2012).
Inman, et al., "Design, modeling and fabrication of a constant flow pneumatic micropump", Journal of Micromechanics and Microengineering, 17(5):891-899 (2007).
Iverson, et al., "Recent advances in microscale pumping technologies: a review and evaluation", Microfluidics and Nanofluidics, 5(2):145-74 (2008).
Kubinyi, "Drug research: myths, hype and reality", Nat Rev Drug Discov 2(8):665-8 (2003).
Laser, et al., "A review of micropumps", Journal of Micromechanics and Microengineering, 14(6):R35-R64 (2004).
Livingston, et al., "Facilitating the commercialization and use of organ platforms generated by the microphysiological systems (Tissue Chip) program through public-private partnerships", Computational and Structural Biotechnology Journal, 14:207-10 (2016).
Long, et al., "Modeling Therapeutic Antibody-Small Molecule Drug-Drug Interactions Using a Three-Dimensional Perfusable Human Liver Coculture Platform", Drug Metab Dispos, 44:1940-1948 (2016).
Loskill, et al., "µOrgano: A Lego®-Like Plug & Play System for Modular Multi-Organ-Chips", Plos One, 10(10):e0139587 (2015).
Maschmeyer, et al., "A four-organ-chip for interconnected long-term co-culture of human intestine, liver, skin and kidney equivalents", Lab Chip, 15(12):2688-99 (2015).
Materne, et al., "A multi-organ chip co-culture of neurospheres and liver equivalents for long-term substance testing", J BiotechnoL, 205:36-46 (2015)KEL Jun. 28, 2022.
Nguyen, et al., "MEMS-Micropumps: A Review", Journal of Fluids Engineering, 124(2):384-92 (2002).
Oleaga, et al. "Multi-Organ toxicity demonstration in a functional human in vitro system composed of four organs", Sci Rep, 6:20030 (2016).
Roth, et al., "The application of 3D cell models to support drug safety assessment: opportunities & challenges", Adv Drug Deliver Rev, 69-70:179-189 (2014).
Small, et al., "Analysis of the accuracy of the bulge test in determining the mechanical properties of thin films", J. Mater. Res, 7(6):1553-63 (1992).
Sung, et al., "Microfabricated mammalian organ systems and their integration into models of whole animals and humans", Lab Chip, 13(7):1201-1212 (2013).
Tandon, et al., "Microfabricated infuse-withdraw micropump component for an integrated inner-ear drug-delivery platform", Biomedical Microdevices, 17(2):37 (2015).
Tandon, et al., "Microfabricated reciprocating micropump for intracochlear drug delivery with integrated drug/fluid storage and electronically controlled dosing", Lab Chip, 16(5):829-46 (2016).
Wikswo, et al., "The relevance and potential roles of microphysiological systems in biology and medicine", Exp Biol Med (Maywood) 239(9):1061-72 (2014).
Woias, "Micropumps: summarizing the first two decades", Proceedings SPIE—, 4560: 39-52 (2001).
Zhang, Science China Physics, Mechanics & Astronomy China-Phys. Mech. Astron, 59(59): 60624 (2016).
Zhu, et al., "A vertical-flow bioreactor array compacts hepatocytes for enhanced polarity and functions", Lab Chip, 16(20):3898-3908 (2016).
Partial International Search Report for corresponding PCT application PCT/US2019/030216 dated Jul. 24, 2019.

(56) References Cited

OTHER PUBLICATIONS

Anonymous: "MIT Thesis FAQ: Access and Availability Questions", Retrieved from the Internet, <URL:https://libguides.mit.edu/c.php?g=176367&p=1159524#13349206> [retrieved on May 27, 2019].
Busek, et al., "Design, characterization, and modeling of microcirculation systems with integrated oxygenators", Journal of Sensors and Sensor Systems, 5(1):221-228 (2016a).
Busek, et al., "Hypoxia-on-a-chip", Current Directions in Biomedical Engineering, 2(1):71-75 (2016b).
Busek, et al., "Microfluidic system for in-vitro hypoxia assays", Proc. SPIE, 10061:1006110-1-1006110-10 (2017).
Domansky, et al., "Multiwell cell culture plate format with integrated microfluidic perfusion system", Proceedings of SPIE, 6112:61120F1-8 (2006).
Domansky, et al., "Perfused Microreactors for Liver Tissue Engineering", Proceedings of the 2005 IEEE Engineering in Medicine and Biology 27th Annual Conference, 7590:7490-7492 (2005).
International Search Report for PCT/US2017/016721 dated Dec. 4, 2017.
International Search Report for PCT/US2018/023411 dated Oct. 25, 2018.
International Search Report for PCT/US2019/022887 dated Jul. 25, 2019.
Mauleon, et al., "Enhanced loading of FURA-2/AM calcium indicator dye in adult rodent brain slices via a microfluidic oxygenator", J. of Neurosci. Methods, 216:110-117 (2013).
Minuth, et al., "Supportive development of functional tissues for biomedical research using the MINUSHEET perfusion system", Clinical and Translational Medicine, 1:22, 14 pages (2012).
Rathbone, et al., "A low volume oxygenator for open well Liver-on-a-Chip tissue culture", Jan. 23, 2018, Massachusetts Institute of Technology, Department of Mechanical Engineering, 150 pages (2018).
Sonntag, et al., "Universal lab-on-a-chip platform for complex, perfused 3D cell Cultures", Progress in Biomedical Optics And Imaging, Spie—International Society For Optical Engineering, 9705: 970516-1-970516-12 (2016).
Van Nguyen, "Design, Modeling, and Validation of an Apical Flow Transwell Insert for Small Intestinal Models", Thesis submitted to the Department of Mechanical Engineering at the Massachusetts Institute of Technology, 1-81, Aug. 2, 2016.

* cited by examiner

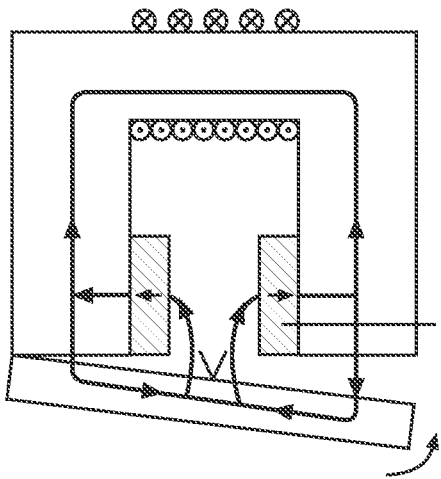 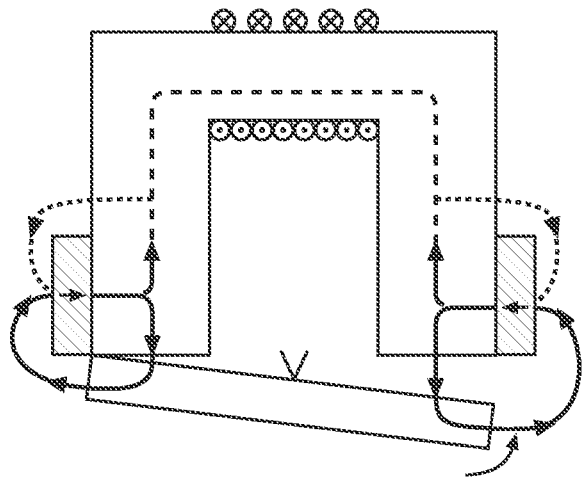
FIG. 13C  FIG. 13D
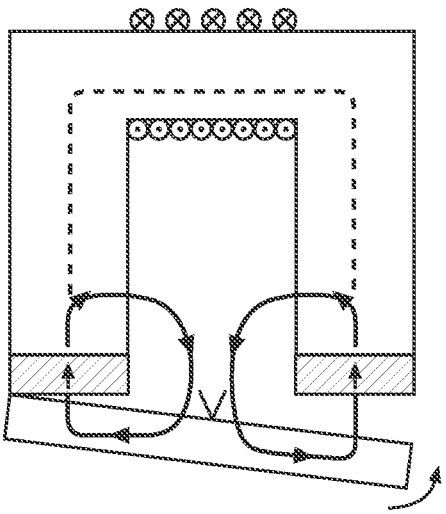 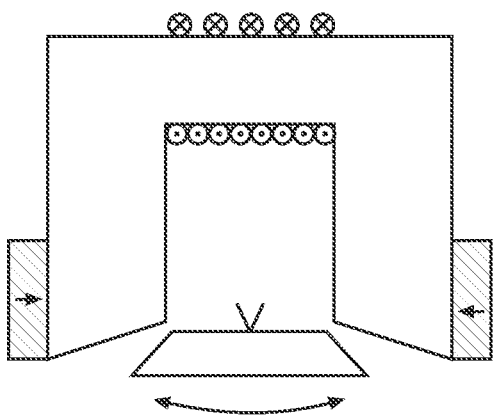
FIG. 13E  FIG. 13F
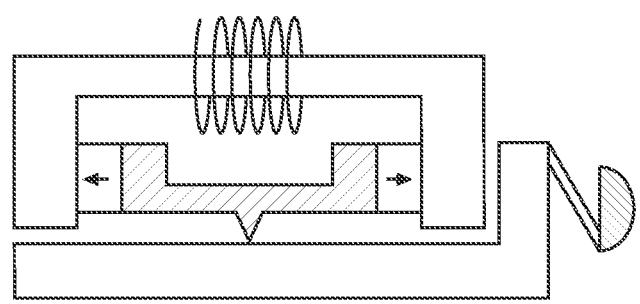
FIG. 13G

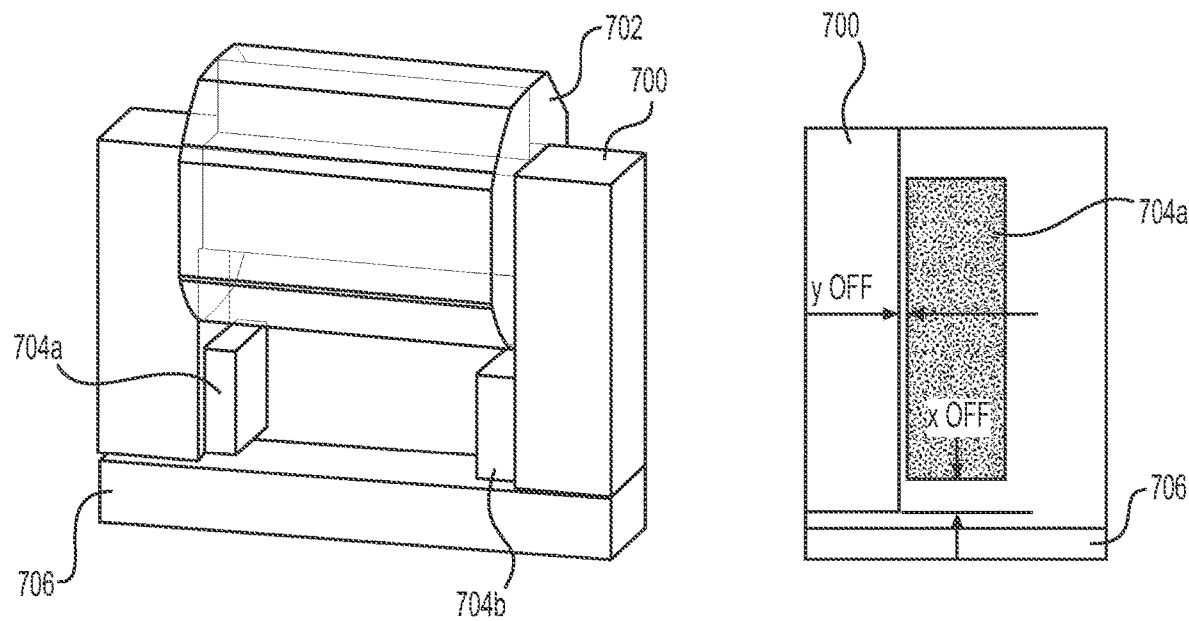
FIG. 24A
FIG. 24B
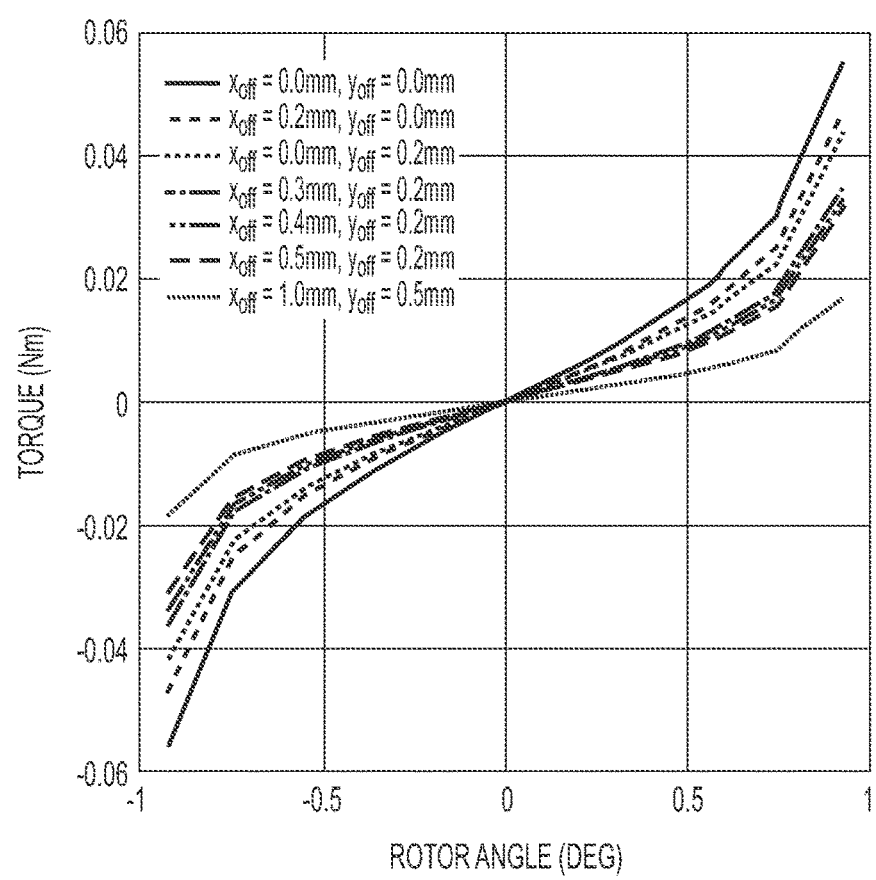
FIG. 25A

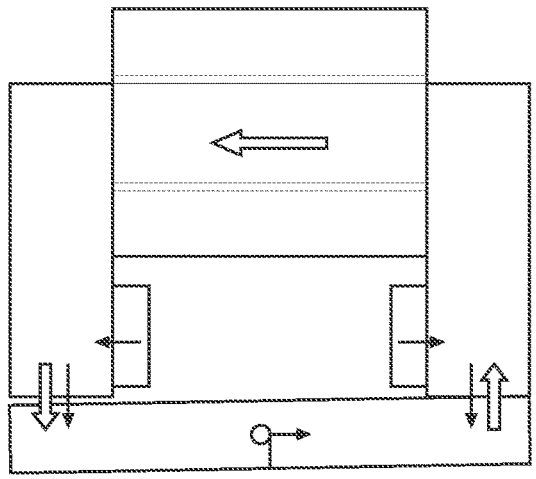
FIG. 26A
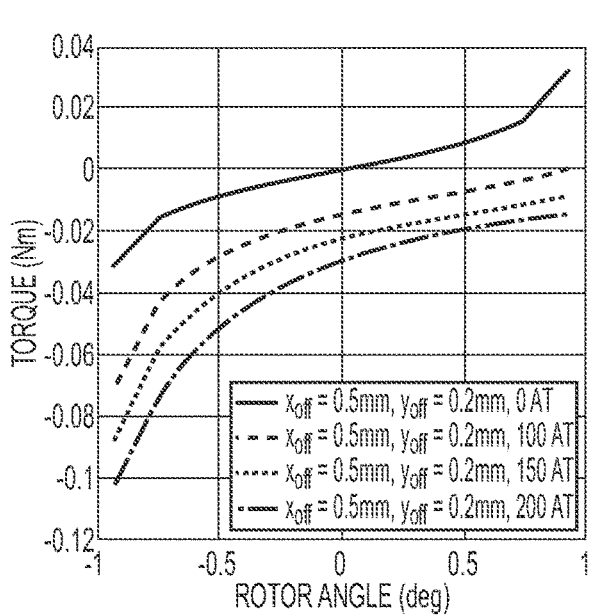 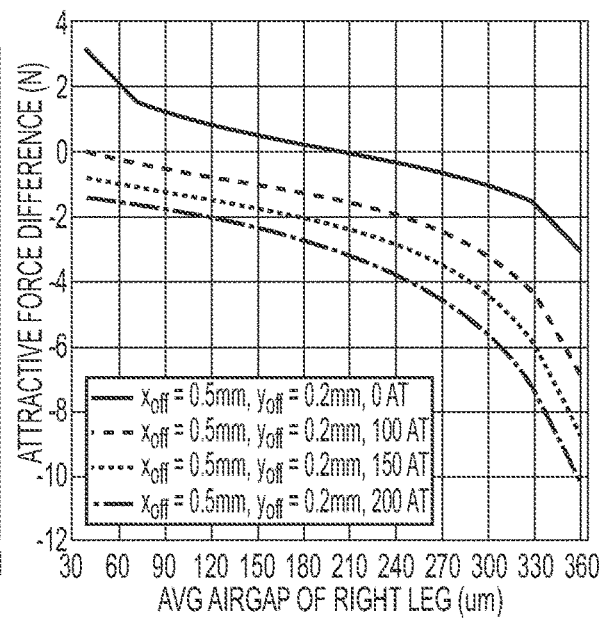
FIG. 26B  FIG. 26C

PUMPS AND HARDWARE FOR ORGAN-ON-CHIP PLATFORMS

CROSS-REFERENCE TO RELATED APPLICATIONS

This application claims the benefit of and priority to U.S. Provisional Application No. 62/665,348 filed May 1, 2018, which is incorporated herein by reference in its entirety.

FIELD OF THE INVENTION

The invention is generally directed to microfluidic devices for cell and tissue culture and to the subcomponents of the microfluidic devices.

BACKGROUND OF THE INVENTION

Recent advances in cell biology, microfabrication and microfluidics have enabled the development of microengineered models of the functional units of human organs, known as organs-on-a-chip (OOC) that could provide the basis for preclinical assays with greater predictive power. Early embodiments have been described and commercialized. For example, U.S. Pat. No. 6,197,575 to Griffith, et al., describes a micromatrix and a perfusion assembly suitable for seeding, attachment, and culture of complex hierarchical tissue or organ structures. U.S. Pat. No. 8,318,479 to Inman, et al., describes a system that facilitates perfusion at the length scale of a capillary bed suitable for culture and assaying in a multiwell plate format. U.S. Application Publication Nos. US 2016/0377599 and US 2017/0227525 A1 describe organ microphysiological systems with integrated pumping, leveling and sensing.

These platforms, termed microphysiological systems (MPSs), are designed to mimic physiological functions by integrating tissue engineering principles with microfabrication or micromachining techniques for recapitulating 3D multicellular interactions and dynamic regulation of nutrient transport and/or mechanical stimulation (Huh D, et al., *Lab Chip,* 12(12):2156-2164 (2012); Sung J H, et al. *Lab Chip* 13(7):1201-1212 (2013); Wikswo J P, et al., *Exp Biol Med (Maywood)* 239(9):1061-1072 (2014); Livingston C A, et al., *Computational and Structural Biotechnology Journal* 14:207-210 (2016); Yu J, et al., *Drug Discovery Today,* 19(10):1587-1594 (2014); Zhu L, et al. *Lab Chip,* 16(20): 3898-3908 (2016)). While significant advances have been made in the development of individual MPS (e.g., cardiac, lung, liver, brain) (Roth A, et al., *Adv Drug Deliver Rev,* 69-70:179-189 (2014); Huebsch N, et al. *Scientific Reports,* 6:24726 (2016); Domansky K, et al. *Lab Chip* 10(1):51-58 (2010)), efforts towards the interconnection of MPS are still in their infancy, with most studies primarily focused on basic viability and toxicity demonstrations (Oleaga C, et al. *Sci Rep* 6:20030 (2016); Esch M B, et al., *Lab Chip* 14(16): 3081-3092 (2014); Maschmeyer I, et al., *Lab Chip* 15(12): 2688-2699 (2015); Materne E M, et al. *J Biotechnol* 205: 36-46 (2015); Loskill P, et al., *Plos One* 10(10):e0139587 (2015)). However, lack of clinical efficacy, rather than toxicity, was identified as the leading cause of drug attrition in Phase II and III clinical trials (the most costly stage) (Kubinyi H, *Nat Rev Drug Discov* 2(8):665-668 (2003); Cook D, et al. *Nat Rev Drug Discov* 13(6):419-431 (2014); Denayer T, et al., *New Horizons in Translational Medicine,* 2(1):5-11 (2014)). Major contributing factors include incomplete understanding of disease mechanisms, the lack of predictive biomarkers, and interspecies differences. There is an urgent unmet need in drug development due to the need for humanized model systems for target identification/validation and biomarker discovery.

While toxicology and pharmacodynamic studies are common applications, pharmacokinetic studies have been limited in multi-MPS platforms. Moreover, current multi-MPS systems may employ a closed format associated with traditional microfluidic chips for operating with very small fluid volumes (Anna S L, *Annu. Rev. Fluid Mech.* 48, 285-309 (2016)). Current fabrication processes for these systems require the use of castable elastomeric polymers (Halldorsson S, et al., *Biosens. Bioelectron.* 63, 218-231 (2015)).

Other practical limitations in the design and fabrication of the hardware also significantly reduce the robustness, long-term reliability, and compatibility of customization in existing multi-MPS devices. Poor hardware designs and constructs often result in a poor control or lack of control on the directionality of fluid among wells (inter-well directionality) and within-well recirculation, leaving some wells dry due to breakage of fluid flow, the syphoning effect, and/or evaporation. Media depletion and waste removal at near-physiological scales often require single-pass media flow, making it difficult or impossible to study slow-clearing drugs, effects of drug metabolites, and inter-MPS communications. Removable inserts to fit into the wells of multi-MPS devices may be desirable in culturing some tissues, but their compatibility with fluid in-flow to support perfusion of cultures has been difficult to achieve.

In the MPS, the common fluid-media circulates between the organs using on-platform pneumatic diaphragm micropumps. These pumps require significant effort in setup and depend on external pressure and vacuum sources. For example, open-well MPS platforms typically require careful assembly of the polyurethane membrane sandwiched between the fluidic top-plates and the pneumatic bottom plates. These platforms require significant effort in setup, which is especially challenging given the sterility requirements during and after assembly. Each pump degree of freedom requires three pneumatic connections (one each for valve, pump and valve). The 7-way platform, which has seven MPSs on-board, has 12 pump degrees-of-freedom and therefore 36 tubing connections. In addition, the top and bottom plates are clamped together with 72 screws.

There remains a need for an independent, portable pump with low power consumption, to simplify the set up and assembly of the platforms. There is also a need to make low-cost sterile platform components for single use, to reduce user setup time and sterilization effort.

It is the object of the present invention to provide independent, portable pumps with low power consumption and easy integration with the platforms.

It is another object of the present invention to provide methods of making the independent pumps and integrating them with the platforms.

SUMMARY OF THE INVENTION

On-platform electromagnetic (EM) pumps for use with the organ-on-chip platforms have been developed. The EM pump uses electrical energy, which may be supplied by a battery, making the pump portable, or plugged into an Alternating Current (AC) 110 volt circuit. The EM pump may use a linear EM actuator having a low energy consumption. The EM pump may use a teeter-totter EM actuator having a low energy consumption. The actuator's low energy consumption is achieved by a latching design which requires only a short pulse of energy to switch its state, flux biasing where the magnetic flux from the winding current adds and subtracts to the magnetic flux from the permanent magnet on either side, and by using springs that store some of the actuator kinetic energy, which is then recovered in the reverse stroke. This further reduces the energy consumption of the actuator.

Also provided are injection-molded, single-use platforms with onboard diaphragm micro-pumps and various valve and pump geometries. The EM actuators easily integrate with these platforms, demonstrating pumping at a constant flowrate, no measurable temperature rise, and valve sealing against varying back-pressure.

The EM actuators are typically suitable for meso- or micro-scale OOC platforms, but may be scaled for any suitable use. Models and criteria for scaling the EM actuators for macro-, meso-, or micro-scale use are provided. The scaling may be isometric, affecting all the elements of the EM actuators and pump similarly, or non-isometric.

The EM actuators typically include a stator body with at least one set of two protruding legs and a connecting segment connecting the two protruding legs. At least two permanent magnets are attached to the body, wherein each permanent magnet forms a pole face on the body about the site of its attachment. A winding coil is typically present around the connecting segment. A rotor or a mover contacts a flexure. Examples of flexures include blade flexures, notch flexures, wire flexures, torsion flexures, folded flexures, cross-flexures, and bushings. A teeter-totter rotor rotates about its pivot point, and has at least two opposing regions. A mover moves linearly when actuated. A contact spring may be connected to the rotor or the mover. The pivot and bearing for the teeter-totter can be provided in a number of ways, including a notch flexure positioned between the two pole faces. The movement of the mover can be provided by one or more flexures positioned between the two pole faces.

Also described are meso- or micro-scale fluidic devices containing a fluidic plate with fluidic channels and at least one chamber, and a pump block containing one or more EM actuators. The chamber is typically positioned in operable proximity to the EM actuator. The fluidic device may include a diaphragm positioned between the chamber and the EM actuator.

In some embodiments, the fluidic device includes a fluidic top plate, a pneumatic bottom plate, and a diaphragm separating the top plate from the bottom plate. The diaphragm may have regions bonded to the top plate, to the bottom plate, or both the top plate and the bottom plate. The diaphragm may have regions that are not bonded to either the top plate or the bottom plate. The diaphragm may also be clamped between the top and bottom plates. The diaphragm may connect to the top plate, the bottom plate or both using bonding, such as adhesive, solvent, thermal, anodic, and/or chemical bonding, or clamping, such as mechanical clamping, clamping using fluidic pressure, and/or clamping using vacuum.

At the contact with the non-bonded diaphragm, the top plate and the bottom plate may form a micropump. The micropump may include at least one, at least two, or at least three chambers in a top plate, optionally comprising at least one, at least two, or at least three chambers in the bottom plate positioned opposite to the at least at least one, at least two, or at least three chambers in the top plate. The chambers in the top plate may have a chamber geometry such as a conical geometry, mid-wall geometry, doormat geometry, and rounded geometry.

Also described are methods for actuating fluid in a fluidic device. The methods typically include contacting the fluid with the diaphragm, displacing volume by moving the diaphragm with the EM actuator. The diaphragm ensures physical separation of the fluidic and the actuation side thereby maintaining fluidic sterility. The actuator typically provides a constant force sufficient to deflect the diaphragm against varying fluid back-pressure to stop fluid flow. The actuator generally operates with low energy consumption and maintains constant displacement stroke with varying back-pressure. The actuator operates without substantial increase in actuator or fluid temperature.

BRIEF DESCRIPTION OF THE DRAWINGS

FIG. 4A shows diaphragm actuation by switching between pressure (P) and vacuum (V) using a bi-stable EM actuator 300 with low power consumption. An advantage is that the pneumatic channels can be placed with a high density on the platform and one pressure switching actuator can actuate many diaphragms at the same time in parallel. FIGS. 4B, 4C, and 4D show embodiments with direct mechanical contact with the membrane to actuate the diaphragm. The membrane makes contact with the sealing lands, sealing the gap thereby closing the valves. FIG. 4B is a diagram showing an embodiment where an EM actuator 344 actuates an elastomer pushing element, such as a button 360 to deflect the membrane 350 and seal the valve 342. FIG. 4C is a diagram showing that the membrane 350 may be pre-stressed for quicker return following deflection by the actuator 344 and button 360 into the valve 362 with ridges 364. FIG. 4D is a diagram of showing a pump chamber 358 and an EM actuator 344 with button 360 positioned bellow the pump chamber 358 and the membrane 350 separating the pump chamber 358 from the button 360. The button 360 may be any elastomer, such as a silicone.

FIGS. 13A-13J are diagrams showing a stator body with two protruding legs and the different embodiments of positioning the permanent magnets on the stator legs. FIGS. 13F, 13G, 13H, and 13I are linear variants of the EM actuators and FIG. 13J shows a cylindrical version of the EM actuator.

FIG. 17B shows diaphragm deflection parameters with coordinate axes r̂, θ̂, ẑ. Shown are chamber wall 603, diaphragm 600, chamber depth h, actuation pressure P, radial displacement u(r), vertical displacement w(r), diaphragm diameter d, and diaphragm radius a. The parameters and their values are shown in Table 7.

FIG. 18A shows diaphragm vertical deflection profile (deflection (mm)) for 5 mm dia. COC diaphragm with increasing radial distance, r (mm) under varying actuation pressure. The curve is modeled using the Timoshenko solution. The membrane solution satisfies the boundary condition for deflection value and slope at the center and the edges. The initial tension in the diaphragm is assumed to be 0. FIG. 18B shows the maximum center deflection ($w_o$ (mm)) vs. pressure (p (kPa)) for various diameters. The region 620 is that which encompasses the pressure actuation range and the allowable maximum deflection, limited by the chamber depth. For the presented pumps, 3-5 mm is the feasible range for chamber diameters. The initial tension in the diaphragm is assumed to be 0. FIG. 18C shows modeling chamber profile and different deflection solutions. Bending solution only considers the bending stresses and therefore overestimates the deflection (dash-dot line). Tensile stress solution only considers the tensile stresses and ignores bending and it also overestimates the deflection for small values of pressure (dash line). The Timoshenko solution incorporates both the tensile and bending stresses and are most representative of the actual deflection (dotted line). In this particular case, the diaphragm touches the chamber walls at a pressure of 12 kPa, beyond which the diaphragm becomes much stiffer and thus there will be a much smaller change in volume with increasing pressure. FIG. 18D shows vertical displacement profile—Timoshenko solution (solid line) overlapped with FEA result (ribbon). FIG. 18E is a diagram showing volume displaced by the diaphragm within the pump chamber 622. The volume displaced would be bounded between the shapes of the Timoshenko deflection 624 and the Tensile stress deflection shape 626 when considering a radius at the edge 628 of the pump chamber.

FIG. 21A measured for a 3 mm chamber diameter, 0.15 mm depth. FIG. 21B measured for 5 mm chamber diameter, 0.25 mm depth. Considering uncertainties of the model and the experiments, the model bounds the displaced volume per stroke well.

FIGS. 24A and 24B are diagrams showing a perspective view of the 3D FEA model of the stator 700, winding 702, permanent magnets 704a and 704b and the rotor 706 (FIG. 24A) and an enlarged view of the bracketed region in FIG. 24A (FIG. 24B). Due to coating of the magnet and the adhesive bonding and alignment and tolerances in assembly, there is an offset in position, which is shown as $y_{off}$ and $x_{off}$.

FIGS. 25A, 25B, and 25C are graphs for the case of zero winding current, showing torque (Nm) versus rotor angle (deg) (FIG. 25A), attractive force difference (N) versus average airgap of right leg (μm) (FIG. 25B), and total attractive force (N) versus rotor angle (deg). (FIG. 25C).

FIG. 26A is a diagram showing winding driven flux density. FIGS. 26B, 26C, and 26D are graphs showing torque (Nm) versus rotor angle (deg) (FIG. 26B), attractive force difference (N) versus average airgap of right leg (μm) (FIG. 26C), and total attractive force (N) versus rotor angle (deg) (FIG. 26D). Winding driven flux density adds to the magnetic field on the left side, while subtracting from the magnetic field on the right side, thereby creating a force differential and a net torque tilting the rotor to contact the left pole face. Positive rotor angle corresponds to the right side of the rotor being closer to the pole face than the left side. Positive attractive force difference corresponds to a greater force on the right side as described in FIGS. 25A-25C.

FIG. 27A shows the right side membrane is fully deflected and is in contact with the pump/valve chamber walls. The left side membrane is undeflected. The maximum stroke of the rotor at the pole face is 400 μm. The maximum membrane deflection is 400 μm. The elastomer gets loaded in a hydrostatic state to uniformly distribute the pressure on the valve sealing lands and seal. FIG. 27B is a simplified schematic with springs connected to the rotor. Rotor is in contact with the left stator pole face. The hard-stops in red limit the deflection of various elements. The stator pole faces limit the deflection at the top of the rotor. The membrane deflection is limited by the chamber walls. Once the contact spring and membrane come in contact, they act as springs in series.

FIG. 30B shows the design of the contact spring 756. The rotation center of the contact spring is close to the rotation axis of the rotor. The pusher 754 pushes at the middle of the contact spring 756. The contact spring 756 gets loaded once the contact spring push-button 758 comes in contact with the membrane 802. The vertical heights are maintained such that the contact spring 756 is parallel to horizontal at the final position of the rotor 752 (rotor latched to the left side pole face (not shown)).

In FIG. 33A the deflection of springs is during rotor switching from the right to the left pole face. When the rotor is latched to the right, the spring elements on the left are deflected. Membrane deflection saturates at 0.1 mm, the notch flexure moves along with the rotor and hence deflects an equivalent ±0.2 mm. Contact springs deflect 0.4 mm keeping push-button vertical at the end of rotor stroke. Note the larger displacements and hence deflections in the push-button and contact springs are due to the larger radius from the center of rotation as compared with the pole face. In FIG. 33B corresponding forces in the springs and the total force on the rotor referred to the right pusher location. The maximum force on the rotor is 1.7 N at end of stroke.

DETAILED DESCRIPTION OF THE INVENTION

I. Definitions

Figure 1A:
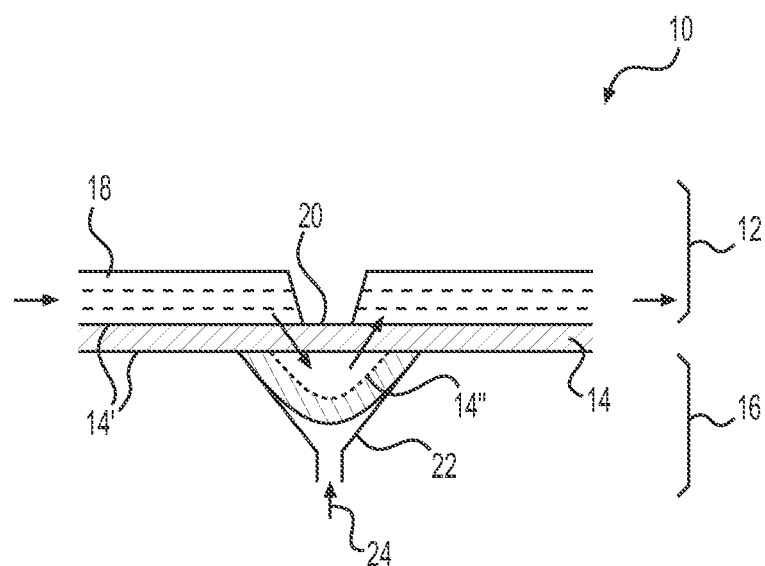
FIGS. 1A-1F are diagrams showing side-section view (FIGS. 1A, 1C, and 1E) and top view (FIGS. 1B, 1D, and 1F) of doormat (FIGS. 1A and 1B), mid-wall (FIGS. 1C and 1D), and rounded (FIGS. 1E and 1F) valve geometries.

The terms "organ-on-chip (OOC)", "bioreactor", and "microphysiological system (MPS)", used interchangeably, refer to the platform providing interactions between single or multiple organs, cell types, or tissue types on a single in vitro platform.

The term "pneumatic" refers to a system which uses air or vacuum pressure for operation.

As used herein, the term "power consumption" refers to a mode of power consumption by a pump to complete one stroke of the pump. As used herein, "low power consumption" refers to a power consumption mode by the pump where the pump consumes power only when the pump is in operation. Typically, the electromagnetic pumps and actuators have a low power consumption, i.e., they consume power only when the rotor is being flipped. For example, in a pump operating at 1 Hz (1 stroke per second (s)), low power consumption pumps would require power for less than 1 second, such as for 1 ms, to flip the rotor once per second, and would not consume power the remaining 999 ms.

As used herein, the term "latching force" refers to the threshold force at which the rotor just flips from one pole face to the other. "Latching" refers to the effect of attaching a portion of the rotor to a pole face of the stator.

As used herein, the term "back-pressure" refers to a pressure in the fluid, which arises due to resistance from internal channels and destination wells, and the tissue-scaffold support structures. This is the minimum pressure that the pump has to develop to cause net flow through the pump.

As used herein, the term "to deflect" refers to a movement by a planar object, such as an elastomeric membrane, in which a portion of the object moves away from, i.e., deflects, from the plane encompassing the surface area of the object.

As used herein, the term "displaced volume per stroke" or "displacement stroke" refers to an actuation parameter describing a volume of fluid displaced per one action (stroke) of the pump. It may be fragmented to describe the volume displaced per action of each one of the valve or a pump in a valve-pump-valve pump, or by the action of the entire pump. The displaced volume per stroke may also be fragmented to describe the volume displaced by the fluidic side, pneumatic side, or on both sides, of the valve per one valve action (stroke).

As used herein, the term "sealing pressure" refers to pressure which is at least the difference between pressure at contact and pressure required to make contact (sealing pressure=(pressure at contact)−(pressure required to make contact)).

As used herein, the term "body" in the context of an actuator refers to an object of a three-dimensional shape with an axis of symmetry, such as symmetry about a horizontal axis, a vertical axis, both, or at an angle. The body typically includes at least one set of two protruding portions in opposition to one another and symmetrical to one another along the vertical axis of symmetry. The body may include more than one set of the two portions, such as two sets, three sets, four sets, etc. The two protruding portions may be three-dimensional objects in the shape of letters I, L, P, etc. For example, the body may be I-shaped, which includes one set of two protruding portions, where each end of the I-shaped body contacts a plane parallel to the vertical axis of summery. In another example the body may be U-shaped, which includes one set of two protruding portions in the shape of the letter L, where each of the protrusions is positioned opposite to the other. Typically, the ends of the protrusions in this example contact the same plane perpendicular to the vertical axis of symmetry. The body may have a cross-sectional area in the shape of pyramid, an oblong, a square, a rectangle, a circle, or any other shape.

As used herein, the term "absorption" refers to incorporation of compounds into the bulk of material, while "adsorption" refers to binding only at the surface.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%.

II. Pumps and Pump Blocks for Organ-On-Chip Platforms

Described are organ-on-chip platforms with independent, portable pumps with low power consumption and easy integration with the platforms. Also provided are methods of making the portable pumps and integrating them with the platforms. Described are also different means of actuation, diaphragm pumps, and electromagnetic pumps.

A. Micro-Pumps for the Pneumatic Plate

The pneumatic diaphragm micro-pumps for the existing platforms consist of three linked valve-pump-valve chambers embedded into these fluid channels (Inman, et al., *Journal of Micromechanics and Microengineering*, 17(5): 891-899 (2007)). The acrylic bottom plate acts as a pneumatic manifold, delivering pressurized air and vacuum locally to each pump and valve chamber. The polyurethane diaphragm sandwiched between the top and bottom plate is actuated by setting pressure or vacuum under the diaphragm.

Sequential actuation of the valve and pump chambers transports fluid in the forward or reverse direction. These pumps are a type of positive displacement pump, transporting an approximately constant volume per stroke over a range of back-pressures. The top and bottom plates are clamped together using an array of screws and spring washers to evenly distribute the clamping force throughout the platform area in order to get sealing across all the fluid elements.

On-platform pumps provide greater flexibility and design freedom. They transport fluid with low dead volumes which is important for studying concentrations of various analytes. In addition, on-platform pumps allow easy interfacing with closed and open microfluidic devices. In the MPS platforms, on-platform pumps transport fluid not only from the mixing chamber to the various organs but also provide recirculation flow to mix the media within an MPS, enhancing nutrient and oxygen transport.

A downside of the current pumps is that they require significant effort in setup, and depend on external pressure and vacuum sources for their operation. This is especially challenging, given the sterility requirements of the platform after assembly.

Provided are embodiments of independent, portable pumps with low power consumption. Platforms containing the portable pumps may be low-cost platforms for single-use, so as to further reduce the sterilization and setup time and effort. Pumps typically include a diaphragm in the pump chamber and at least two valves. At least one of the valves is positioned upstream and at least one of the valves is positioned downstream of the pump chamber. The valves are fluidically connected with the pump chamber, as well as to the source and delivery points, via fluidic channels.

1. Diaphragms

The pump chamber typically includes at least on diaphragm, which may be a flexible membrane.

a. Materials and Geometry

Typically, the diaphragms are made of materials such as elastomeric synthetic or natural polymers. Examples of synthetic elastomers include polyurethane (PU), polyethylene oxide (PEO), polybutylene terephthalate (PBT), polyether sulfone (PES), polyimide (PI) polymers, TEFLON®/PTFE, polystyrene, cyclic olefin copolymer (COC), and block copolymers and asymmetric blends thereof.

The diaphragm may have geometry of a flat sheet, such as a membrane, with length, width, and thickness suitable for assembly and operability with the organ-on-chip platforms. For example, the diaphragm may have a length and width substantially similar to the length and width of the bottom surface of a fluidic plate. The diaphragm may have a length and width substantially similar to the length and width of a pump block. For the actuating diaphragm, i.e., the unbound or unsealed region of diaphragm within each chamber, the range of dimensions for the diaphragm depend on the pump and valve geometry chambers and can be matched to those dimensions. Typically, these dimensions range between about 1 mm and about 10 mm in diameter, such as between about 1 mm and about 8 mm, between about 1 mm and about 6 mm, such as about 1 mm, about 2 mm, about 3 mm, about 4 mm, about 5 mm, about 6 mm, about 7 mm, about 8 mm, about 9 mm, or about 10 mm in diameter. The diaphragm may thickness may be between 0.025 mm and 1 mm. Suitable thickness for the diaphragm includes between about 0.025 mm and about 0.75 mm, between about 0.025 mm and about 0.5 mm, between about 0.025 mm and about 0.25 mm, between about 0.025 mm and about 0.1 mm, between about 0.05 mm and about 0.1 mm, or between about 0.05 mm and about 0.75 mm, such as about 0.05 mm, about 0.06 mm, about 0.065 mm, about 0.07 mm, about 0.075 mm, or about 0.1 mm.

b. Deflection

The diaphragms typically deflect and provide a set displaced volume for a given actuation pressure. The diaphragm deflection and the displaced volume for a given actuation pressure may be modeled and verified. This allows determining the suitable geometry of the diaphragm and the displaced volume per stroke. Finite Element Analysis (FEA) may be used to experimentally validate the models.

In some embodiments of single-use platforms, the pneumatic and fluidic plates are made of Cyclic-Olefin-Copolymer (COC) and the diaphragm is also made of 0.065-0.075 mm thick sheet of COC. Modeling may be used to predict the impact of various factors such as the actuation pressure and diaphragm area on the deflection of the diaphragm to design the pump and valve chamber geometries. The deflection behavior of the diaphragm within the pump and valve chambers is responsible for the pressure vs. volume-flow-rate characteristics such as volume-per-stroke, back-pressure capability, and sealing pressures for these micro-pumps.

Diaphragm deflections can be categorized into four categories.

i. Small Deflections

In small deflections, the diaphragm deflection is limited to be smaller than the diaphragm thickness. The stress state within the diaphragm is primarily bending-dominated. These are usually analyzed using von-Kármán plate theory as the boundary conditions are easier to resolve and exact analytical solutions exist (Timoshenko and Woinowsky-Krieger, *Theory of Plates and Shells*, 2nd ed. McGraw-Hill, New York, (1959)).

ii. Large Deflections

In large deflections, the diaphragm deflection is larger than about 1.5 times the diaphragm thickness. The stress state is dominated by tensile stresses in the diaphragm. These are also called membrane deflections. A spherical deflection shape is assumed and these are analyzed using solutions for thin spherical shells.

iii. Intermediate Deflections

In intermediate deflections, the diaphragm deflections are of the order of the diaphragm thickness. Both bending moments and tensile stresses contribute significantly to the stress state. This is a general case and the solutions to this should lead to the small deflection solution for the limit of small deflections and the large deflections solutions at the upper limit. This solution is most applicable for analysis of diaphragm deflections as typical pump and valve chamber depths are of the order of the membrane thicknesses.

iv. Flexible, Free Diaphragms

In flexible, free diaphragms, as noted in (Schomburg, "Membranes," *Introduction to Microsystem Design*, Springer, Berlin, Heidelberg, 1:29-52 (2011)) the diaphragm is so flexible that bending moments and tensile stresses are negligible. There is slack in the diaphragm to accommodate the deflections of interest with almost zero stress in the diaphragm until all the slack is removed, beyond which the diaphragm stiffness suddenly increases. The diaphragm acts as a partition between the two sides and allows for the net transfer for pressure from one side to another with minimal pressure difference across the membrane. The diaphragm shape at equilibrium is undetermined, and at equilibrium, the pressures on both sides of the diaphragm are equal.

2. Valves

Valves are typically designed to operate under a sequential open and closed configurations. A pressure or vacuum source, or other actuation source acts on the diaphragm to close or open the valve. The valve typically includes at least one sealing land or sealing region. The diaphragm in the valve typically contacts the sealing land or the sealing regions with a pre-determined pressure to seal the valve.

When the valves are closed, fluid flow through the valve is prevented by the sealing of the diaphragm against the sealing lands. The minimum pressure to seal against the sealing lands ($P_{min}$) is typically low enough to give a high back-pressure capability ($P_{back\text{-}pressure}$). For an actuation pressure ($P_{act}$) greater than $P_{min}$, $P_{back\text{-}pressure}$ is defined as, $$P_{back\text{-}pressure} = P_{act} - P_{min} \qquad \text{Equation 3.1}$$

When the valves are open, fluid flows through the valve with minimal resistance. The fluidic resistance is typically low and the resistance to flow may be negligible compared to the upstream and downstream fluid channels. During the switching between closed and open, valves minimize the displaced volume as these are seen as pulses in the pump flow profile.

Valves typically displace minimal volume in operation. When closed, they seal up to a certain pressure, and when open they typically add negligible resistance to the fluid flow path. Since the flow regime is laminar, the flow is viscous-dominated on the average flow-rate and the flow resistance comes from friction at the walls. In operation, as long as it provides greater cross-sectional area for flow compared to the fluid channel, the relative fluid resistance by the valve should be small.

The net volume displaced by the valves across a pump cycle may be about 0. Each valve undergoes a suction and discharge stroke within one pump cycle, pushing or pulling the same amount of fluid with each stoke from a side of the pump. In operation, the volume displaced when the valve opens or closes will be seen as a flow pulse. Typically, the amplitude of the pulse becomes smaller as the volume displaced by the valve reduces.

a. Valve Geometries

Valves may have different geometries, such as described in FIGS. 1A-1F. Valve geometries include doormat valve, mid-wall valve, and rounded valve.

Valves may include structures such as one or more sealing lands, one or more fluid channels, a membrane, one or more pressure channels, one or more pressure points, and/or valve walls. All or some of the structures may be arranged in a fluidic (top) plate. All or some of the structures may be arranged in the bottom plate.

i. Doormat Valve

Figure 1B:
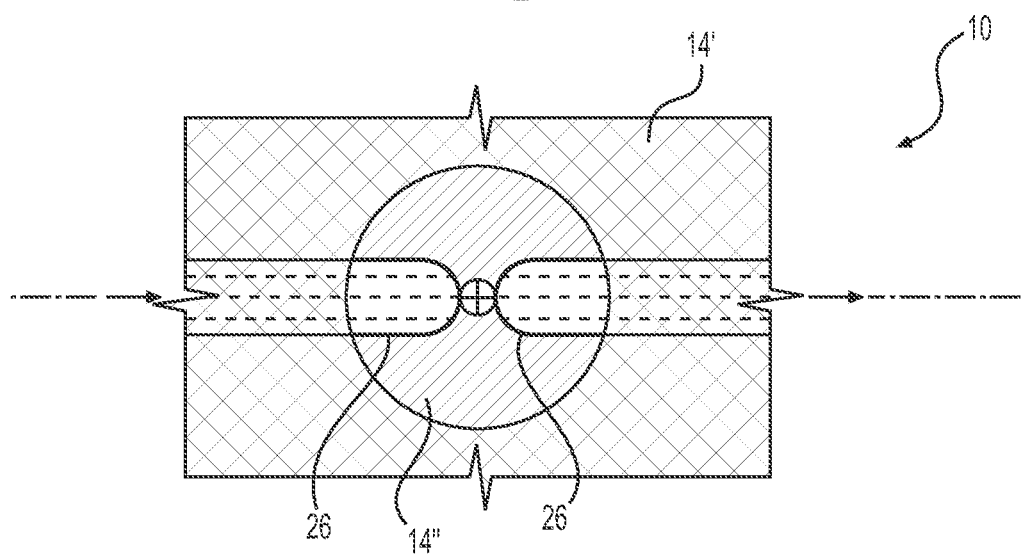

In some embodiments, the valves include, in the top plate, at least one sealing land and two opposing fluid channels separated by the sealing land, and, in the bottom plate, valve chamber walls and at least one pneumatic channel. A diaphragm membrane separates the structures of the top plate from the structures of the bottom plate. This embodiment encompasses doormat valves presented in FIGS. 1A and 1B. FIGS. 1A and 1B show the doormat valve 10 with the fluidic channel 18 and sealing land 20 in the top plate 12, a membrane 14 positioned between the top plate 12 and the bottom plate 16, as well as chamber wall 22 and a pneumatic port 24 for providing pressure to close or vacuum to open the valve, positioned in the bottom plate 16. The membrane 14 has regions 14' bonded to the top plate 12 and the bottom plate 16, as well as regions 14" without bonding. The membrane 14 forms sealing regions 26 for sealing fluid flow through the fluid channel 18.

ii. Mid-Wall Valve

Figure 1C:
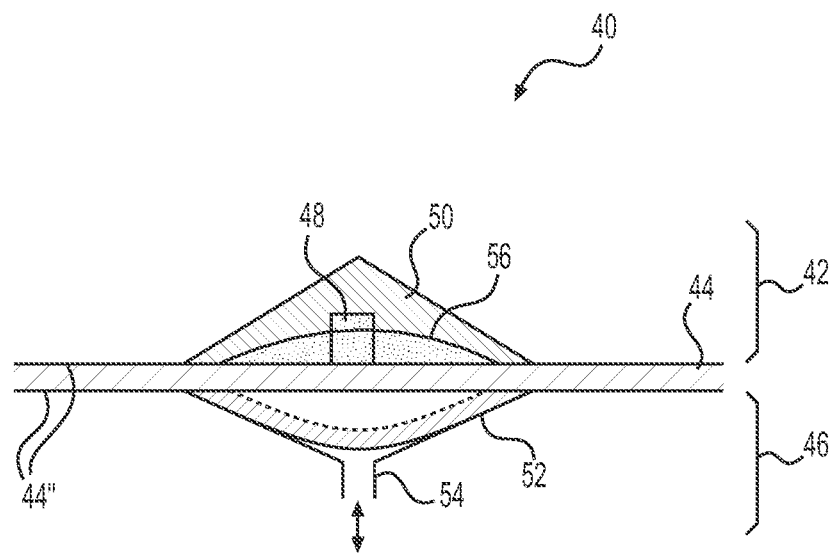
Figure 1D:
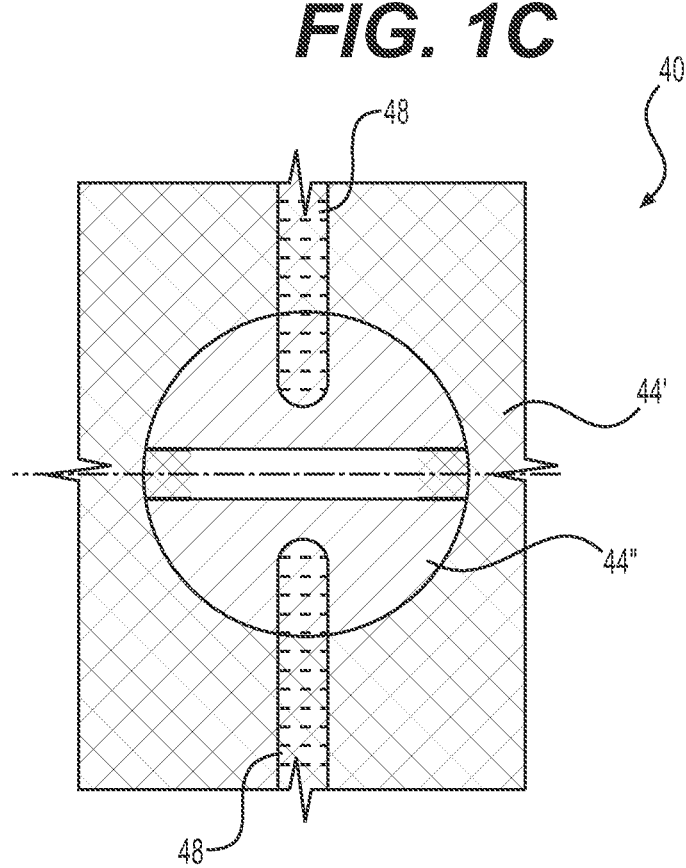

In some embodiments, the valves include, in the top plate, at least two sealing regions, one fluid channel, and valve top chamber walls, and, in the bottom plate, valve chamber walls and at least one pneumatic channel. A diaphragm membrane separates the structures of the top plate from the structures of the bottom plate. This embodiment encompasses mid-wall valves presented in FIGS. 1C and 1D. FIGS. 1C and 1D show the mid-wall valve 40 with fluid channel 48 and valve sealing region 56 in the top valve chamber 50 positioned in the top plate 42, a membrane 44 positioned between the top plate 42 and the bottom plate 46, and a pneumatic channel 54 for providing pressure to close or vacuum to open the valve, with bottom valve chamber wall 52 positioned in the bottom plate 46. The membrane 44 has regions 44' bonded to the top plate 42 and the bottom plate 46, as well as regions 44" without bonding. The membrane 44 forms sealing region 56 for sealing fluid flow through the fluid channel 48.

iii. Rounded Valve

Figure 1E:
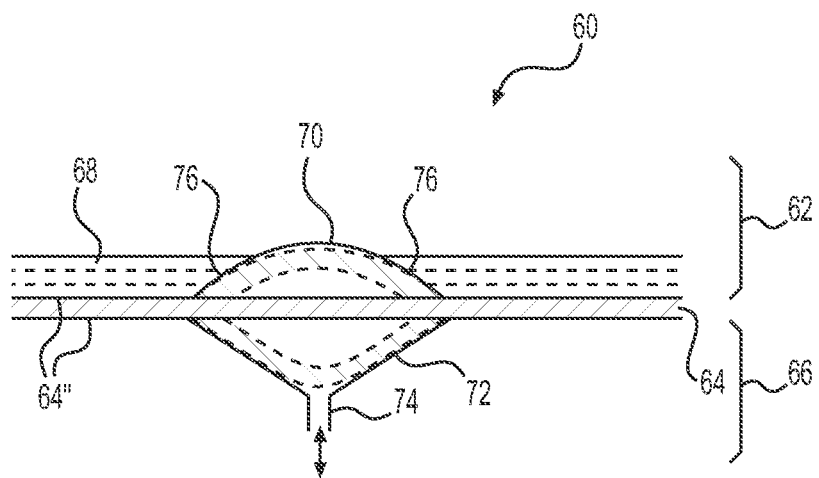
Figure 1F:
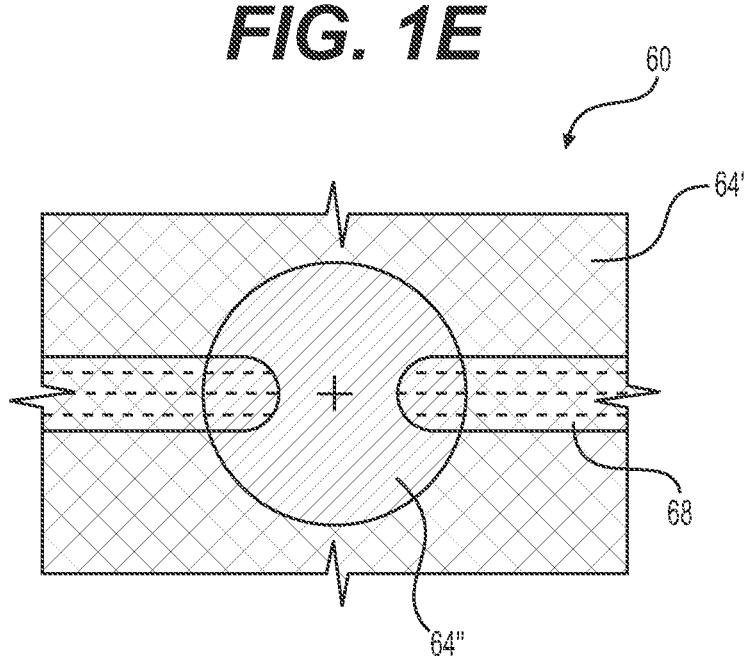

In some embodiments, the valves include, in the top plate, a valve sealing region and a valve top chamber wall, and, in the bottom plate, valve chamber walls and at least one pneumatic channel. A diaphragm membrane separates the structures of the top plate from the structures of the bottom plate. This embodiment encompasses rounded valves presented in FIGS. 1E and 1F. FIGS. 1E and 1F show the rounded valve 60 with fluid channel 68 and valve sealing region 76 in the top valve chamber 70 positioned in the top plate 62, a membrane 64 positioned between the top plate 62 and the bottom plate 66, and a pneumatic channel 74 for providing pressure to close or vacuum to open the valve, with bottom valve chamber wall 72 positioned in the bottom plate 66. The membrane 64 has regions 64' bonded to the top plate 62 and the bottom plate 66, as well as regions 64" without bonding. The membrane 64 forms sealing region 76 for sealing fluid flow through the fluid channel 68.

The structures of valve chambers in the bottom plate accommodate features for actuation of the diaphragm. These may include actuation schemes which apply a pressure differential across the membrane such as pneumatic, hydraulic, electrostatic, thermal and also direct actuation schemes which apply a force on the diaphragm using electromagnetic, piezoelectric, and other means of developing forces in contact with the diaphragm such as with linkages, cams and flexures.

b. Valve Function

For normally closed valve geometries such as the doormat valves, vacuum pulls the diaphragm opening the valve (FIGS. 1A and 1B). Since the valves do not contribute to the net volume per stroke of the pump, bounding of the diaphragm deflection is not necessary for the valves. In operation, opening the valves such that the cross-sectional area is more than the fluid channel is adequate.

In one embodiment, a 3 mm doormat valve may be used. The spacing between the fluid channels on each side of the valve may be selected nominally as the width of the fluid channel, i.e., 0.4 mm. The model, described in Example 1, predicts that it requires 25 kPa to deflect the membrane to have the same cross-sectional area as the fluid channel (0.4×0.1=0.04 mm$^2$). Actuating at 40 kPa, the deflection would be 0.06 mm and the volume displaced would be 0.2 µL (Table 1). The diaphragm may be bonded on both sides and may not require additional sealing lands which are facilitated by V-cuts like the machined pumps of existing pneumatic diaphragm micro-pumps.

For the normally open geometries such as the mid-wall valves (FIGS. 1C and 1D), pressure pushes the diaphragm against the sealing land and closes them. At the neutral position of the diaphragm, they may have cross-sectional area more than that of the channels. When open, the selected valve dimensions of 4 and 5 mm diameter have a larger cross sectional area than the fluid channels. Table 1 compares the volume displaced by various valve configurations. Providing a gentle valve seat curvature prevents forming points of high stress concentration in the membrane. Mid-wall valve configurations have a larger volume displaced per stroke, especially for bi-directional pneumatic actuation. This volume can potentially be reduced if the chamber depth on the pneumatic side is reduced. Due to concerns with bonding touchdowns (unintended bonding of the diaphragm with the fluidic plate at the active pump and valve features), the depth may be at 0.1 mm on the pneumatic side.

The rounded valve geometry (FIGS. 1E and 1F) requires much larger pressures for actuation as the sealing surfaces have a sharper curvature. Therefore a larger diameter, 5 mm may be selected with a chamber depth of 0.1 mm.

The doormat valve requires masking of the flat sealing-land region of the top-plate during bonding, so that the diaphragm is not bonded at that region and is free to actuate (FIGS. 1A-1F). This is a more complex process and has a higher risk of failure in manufacturing. The mid-wall and the rounded valves have recessed sealing lands which makes it easier to bond the diaphragm to the top plate. Therefore, all the three types of valves were selected for evaluation with the test pump block (described in Example 4).

TABLE 1

Valve actuation parameters. The minimum pressures and forces required to actuate the diaphragm to open (doormat) and seal the valves are tabulated. The volume displaced per stroke on each side (F: fluidic side, P: pneumatic side) for a nominal 40 kPa actuation are also given.

| Valve | Dia. [mm] | Height (min.) [mm] | Press (min) [kPa] | Force (min.) [N] | ΔVol. (one-sided) [µL] | ΔVol. (two-sided) [µL] |
|---|---|---|---|---|---|---|
| Doormat | 3 | 0.025 | 25 | 200 | 0.15(P)/0.0(F) | 0.15 |
| Midwall | 4 | 0.075 | 20 | 250 | 0.4(P)/0.2(F) | 0.60 |
|  | 5 | 0.075 | 10 | 200 | 0.6(P)/0.4(F) | 1.00 |

3. Pump Chamber

Similar to valves, pumps include a diaphragm separating pump chamber structures positioned in the top plate form pump chamber structures positioned in the bottom plate. The structures of the bottom plate may be connected to the same or similar actuation means connected to the valves' structures.

a. Pump Chamber Geometry

Figure 2:
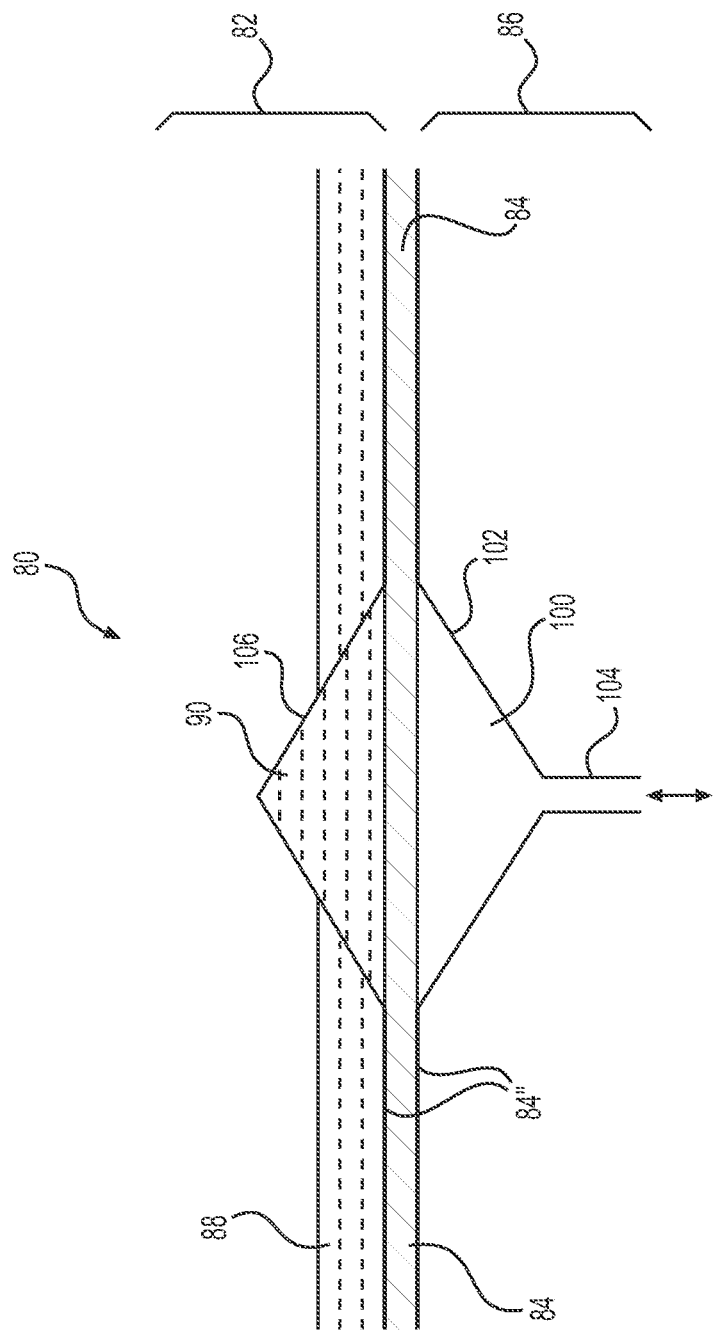
FIG. 2 is a diagram showing a cross-section through a pump chamber. Pump chamber 80 has an upper fluidic chamber 90 and a bottom chamber 100, both of a conical shape. The pump chamber 80 has a fluid channel 88 and the upper fluidic chamber 90 positioned in the top plate 82, and a membrane 84 positioned between the top plate 82 and the bottom plate 86. The bottom plate 86 includes a pneumatic channel 104 for providing pressure to close or vacuum to open the pump, bottom chamber 100 and a bottom chamber wall 102. The membrane 84 has regions 84" bonded to the top plate 82 and the bottom plate 86, as well as regions without bonding positioned between the upper fluidic chamber 90 and the bottom chamber 100.

Pump chambers may have different geometries, and one suitable pump chamber arrangement is described in FIG. 2. The pump chambers may include structures selected from the group of one or more pump chamber walls, one or more sealing lands, one or more sealing regions, one or more sealing points, a membrane, one or more pressure channels, and one or more pressure points. All or some of the pump chamber structures may be arranged in a fluidic (top) plate. All or some of the pump chamber structures may be arranged in the bottom plate.

In some embodiments, the pump chambers include, in the top plate, at least one pump chamber wall and a fluidic channel in contact with the pump chamber wall, and, in the bottom plate, pump chamber walls and at least one pressure channel in contact with the pump chamber walls. A diaphragm membrane separates the structures of the top plate from the structures of the bottom plate.

The pump chamber depth may be between about 0.01 mm and about 0.5 mm, such as between about 0.02 mm and about 0.4 mm, between about 0.05 mm and about 0.3 mm, between about 0.05 mm and about 0.15 mm, or about 0.1 mm. In preferred embodiments, the pump chamber depth is between about 0.05 mm and about 0.15 mm, such as 0.1 mm.

b. Pump Chamber Function

For deterministic volume displacement per stroke, the actuation pressure ($P_{act}$) is typically greater than the minimum pressure required to drive the diaphragm deflection into contact with the pump chamber walls ($P_{min}$). The back-pressure capability is then also given by Equation 3.1. The geometry of the pump chamber walls and the shape taken by the membrane together determine the volume displacement per pump stroke.

Both pumps and valves typically avoid situations where the diaphragm deflection can get self-locked. For example, when actuated with vacuum, the diaphragm can seal off the pneumatic port and the diaphragm deflection becomes undetermined. A similar situation may happen if the diaphragm deflection seals off the fluid channel entering the valve or pump chamber. In addition, stiction of the diaphragm with the chamber walls or sealing lands is typically avoided. There may be regions in the contact region where the fluid (media or air) may displace the diaphragm from such a state when actuated. For example, if the diaphragm is stuck to the pneumatic chamber walls when under vacuum, since the pneumatic port (pressure channel) is at the bottom of the chamber (FIG. 2) during the next pressure stroke, the diaphragm typically get dislodged again. Stiction depends on the surface properties of the materials in contact and the presence of fluids can modify the stiction forces significantly.

In preferred embodiments, the pump chamber uses a conical chamber geometry which makes the diaphragm have a well-defined contact propagation with the chamber walls and ensures that the diaphragm can never go into a self-locked state. It touches the slant wall of the cone at first contact. Further deflections bring more of the diaphragm in contact with the walls, with the diaphragm sequentially progressing towards the pneumatic port.

As discussed in Example 1, as the diaphragm comes in contact with the chamber walls, it becomes much stiffer, and the volume displaced almost saturates. The difference between the actuation pressure and the minimum pressure for contact is approximately the back-pressure capability of the pumping chamber.

Figure 3A:
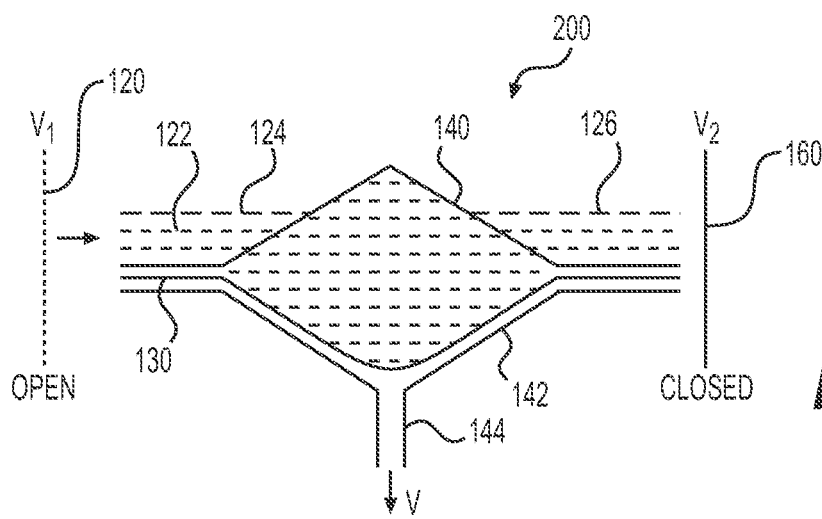
FIGS. 3A-3C are diagrams showing the steps of fluid flow through the pump chamber 200 and the corresponding membrane deflections with inlet/outlet fluidic channels shallower than the upper fluidic chamber height.
Figure 3B:
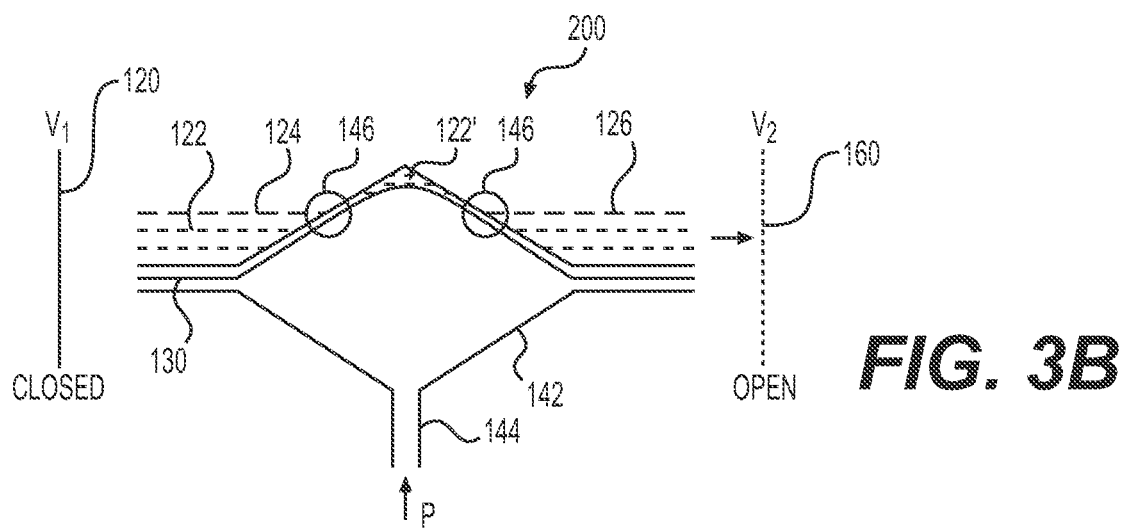
Figure 3C:
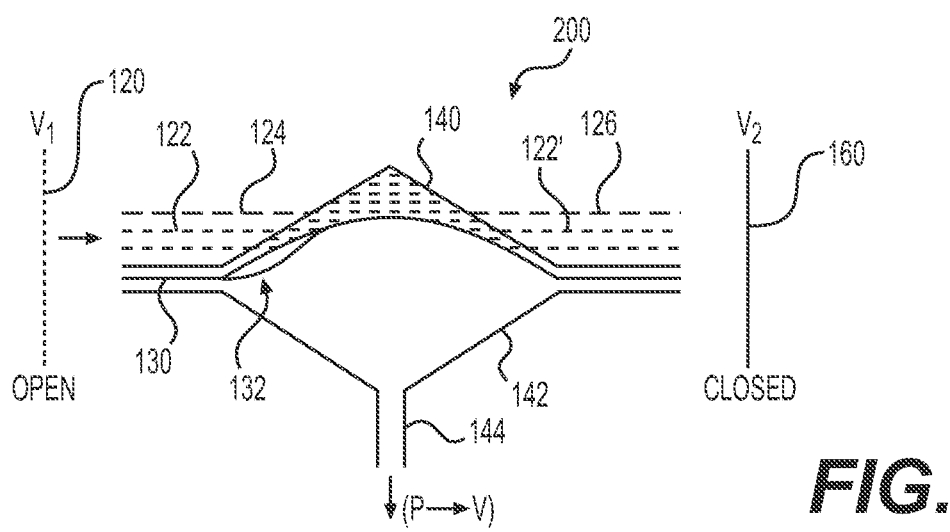
Figure 4A:
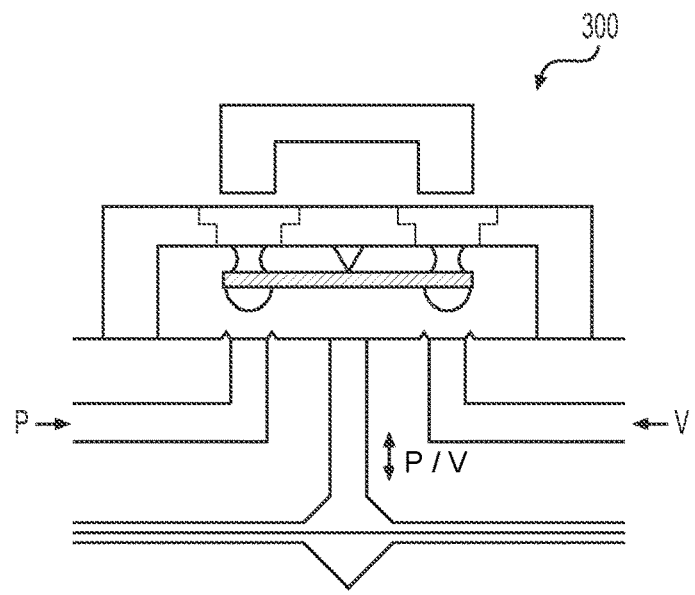
FIGS. 4A-4D are diagrams showing different pump embodiments.
Figure 4B:
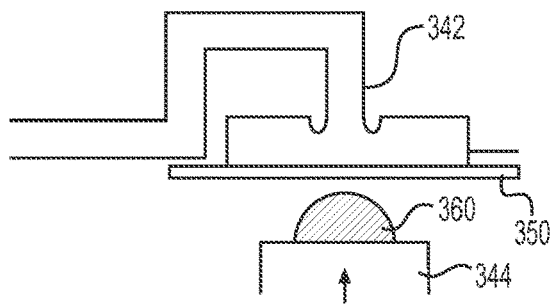
Figure 4C:
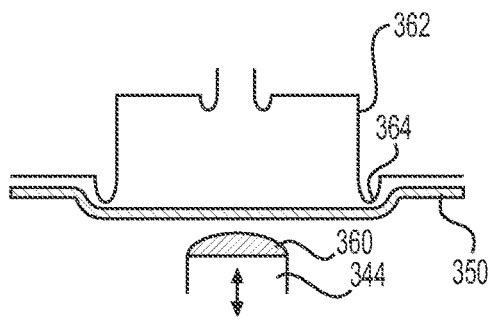
Figure 4D:
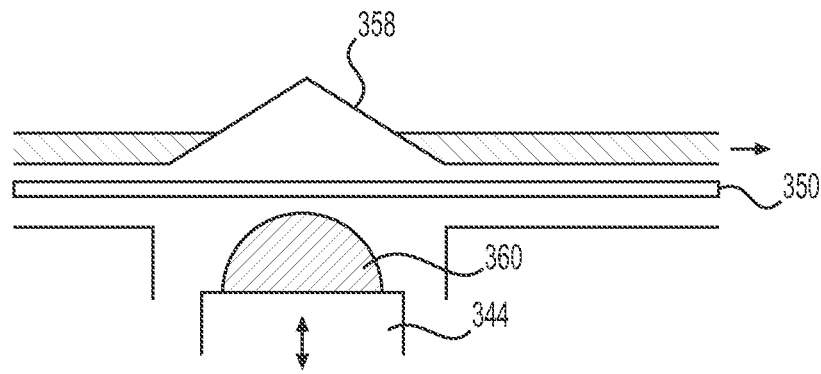

To prevent a state of self-locking, the fluid channels which enter the pump chamber may have a shallow depth, such as a depth of 0.1 mm. Therefore, there is always a pathway for the fluid to get evacuated, and no fluid can get trapped as shown in FIGS. 3A-3C. The COC membrane has a relatively low coefficient of friction with COC and maintains surface integrity under contact stresses. Therefore, it exhibits low stiction with the chamber walls in operation. FIG. 3A shows the step of fluid 122 filling through fluid channel 124 into the upper fluid chamber 140 when the membrane 130 is deflected into the bottom chamber 142 with vacuum (V) provided through the pneumatic channel 144. At this step, the valve 120 preceding the pump chamber 200 is open, and the valve 160 succeeding the pump chamber 200 is closed. FIG. 3B shows the step of fluid pumping (evacuating) in the pump chamber 200. The fluid 122 is pumped out of the upper fluid chamber 140 and into the fluidic channel 126 by deflection of the membrane 130 into upper fluid chamber 140 with pressure (P) provided through the pneumatic channel 144. This stops fluid flow by forming sealing points 146 in the upper fluid chamber 140. Fluid 122' is trapped in the upper fluid chamber 140. At this step, the valve 120 preceding the pump chamber 200 is closed, and the valve 160 succeeding the pump chamber 200 is open. FIG. 3C shows the step of opening the pump chamber 200 for fluid flow. The membrane 130 unlatches from the upper fluid chamber 140 at point 132 to break the suction when pressure (P) is changed to vacuum (V) through the pneumatic channel 144. At this step, the valve 120 preceding the pump chamber 200 is open, and the valve 160 succeeding the pump chamber 200 is closed. The shallower inlet/outlet fluid channels 124 and 126 lead to a potential sealing point 146 where the diaphragm can seal off either the entry or the exit to the pump chamber. This may cause non-deterministic fluid volumes per pumping stroke, and may be adjusted by changing the fluid channel height.

TABLE 2

Parameters of exemplary pump chamber geometries s. Diaphragm material is COC with thickness 0.065-0.075 mm. Modeling details are in Example 2.

| Dia. [mm] | Height [mm] | Stroke vol. (one-sided) [μL] | Stroke vol. (two-sided) [μL] | Pressure (wall-contact) [kPa] | Force (wall-contact) [mN] |
|---|---|---|---|---|---|
| 5 | 0.1 | 0.65 | 1.30 | 10 | 200 |
| 4 | 0.1 | 0.42 | 0.84 | 25 | 325 |
| 3 | 0.1 | 0.24 | 0.42 | 75 | 525 |

4. Fluid Channels

The fluid channels connect the pump to the source and delivery points, and also between the valves and the pump chambers. The flow through fluid channels may affect pump behavior. During pumping, especially for pulsatile flows, the flow resistance and inertance of the channels may affect pump behavior. In addition, the fluid channels may hold a certain volume captive that needs to be evacuated before the media introduced at the source point reaches the delivery point.

The fluid channels are located at the entrance and exit to the pumps and valves, and may interconnect the valves to pumps.

At the entrance and exit to the pumps and valves, the fluid channels typically have a same or greater depth than the chamber depth. A smaller channel depth could be sealed off by the membrane, causing self-locking (FIGS. 3A-3C). Propagation of diaphragm deflection in a conical chamber may proceed as follows. The contact with the wall linearly propagates upwards with increasing pressure. As that happens, the effective diameter of the diaphragm reduces and the diaphragm stiffness increases approximately quadratically.

However, deeper channels running across the pump chamber may increase the chance of membrane deflection into the channels leading to an uncertainty of the displaced volume and possible membrane damage due to the channel sharp corners. The channel depth may be the same as or greater than the chamber depth. The channel depth may be between about 0.01 mm and about 0.5 mm, such as between about 0.02 mm and about 0.4 mm, between about 0.05 mm and about 0.3 mm, between about 0.05 mm and about 0.15 mm, or about 0.1 mm. In preferred embodiments, the fluid channel depth is between about 0.05 mm and about 0.15 mm, such as 0.1 mm.

The channel width may be between about 0.1 mm and about 2 mm, between about 0.5 mm and about 1.5 mm, such as about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.2 mm, about 1.4 mm, about 1.6 mm, about 1.8 mm, about or 2 mm.

A sufficiently large hydraulic diameter (cross-sectional area/perimeter) leads to a low fluidic resistance. At the same time, the cross-sectional area should be small to minimize the captive volume within the fluid channels. In preferred embodiments, a fluid channel has dimensions of about 0.4 mm wide and about 0.1 mm deep. This channel has a fluid pressure drop of about 0.03 kPa/mm for a flowrate of 1 μL/A and a captive volume of about 0.04 μL/mm.

B. Actuation Means and Pumping Designs

Pumps can be classified into two main categories, along the lines of pump classifications (Woias, *Proceedings of the SPIE—The International Society for Optical Engineering*, 4560: 39-52 (2001); Iverson, et al., *Microfluidics and Nanofluidics*, 5(2):145-174 (2008); Laser, et al., *Journal of Micromechanics and Microengineering*, 14(6):R35-R64 (2004); Nguyen, et al., *Journal of Fluids Engineering*, 124(2):384 (2002)):

1. Mechanical displacement micro-pumps exert oscillatory or rotational pressure forces on the working fluid through a moving solid-fluid (vibrating diaphragm, peristaltic, rotary pumps), or fluid-fluid boundary (ferrofluid, phase change, gas permeation pumps).

2. Electro-kinetic and magneto-kinetic micropumps provide a direct energy transfer to pumping power and generate constant/steady flows due to the continuous addition of energy (electroosmotic, electrohydrodynamic, magnetohydrodynamic, electrowetting).

At the scale of milli-, and microfluidics, the surface to volume ratio is much larger than that on a macro scale, which leads to high viscous forces and restricts downscaling of well-known macro-scale mechanical pump principles. In addition, surface energy effects can become dominant and need to be considered (Nguyen et al., *Journal of Fluids Engineering*, 124(2):384-392 (2002)).

Typically, micropumps have flowrate range from a few μL/s to several mL/s. With these flow rates, most of the micropumps work in the range of Reynolds number from 1-100, and are therefore in a laminar regime (Nguyen et al., *Journal of Fluids Engineering*, 124(2):384-392 (2002)).

Typically, the structural features for pumps are the following:

1. the pump material is typically biocompatible; for example, the portion of the pump that comes most in contact with the pumped fluid is typically sterile, bio-compatible, and does not substantially absorb or adsorb drugs, 2. the mean and maximum flow-rates and flow profiles of the pumps permit their use with meso-scale and micro-scale features of the organ-on-chip platforms, 3. the maximum back-pressure the pumps have to pump against may vary, and in some aspects may be up to 20 kPa in operation. Independent of the back-pressure, the pump typically delivers a consistent volume of fluid per pump stroke. In some aspects, the back-pressure may be up to about 100 kPa, such as between about 5 kPa and about 75 kPa, between about 10 kPa and about 40 kPa, such as about 20 kPa, while providing a constant displaced volume per stroke, 4. the size and structure of the pumps permit scalability (ability to be multiplexed), 5. the pumps have a bidirectional capability, 6. the pumps have a low power requirements, 7. the pumps permit media recirculation or single flow-through, and 8. the pumps do not obstruct flow by clogging and can clear bubbles through function/actuation.

The pneumatic diaphragm pumps have been used successfully to demonstrate up to 10-organ interactions. These pumps require significant effort in setup and depend on external pressure and vacuum sources. An independent, portable pump with low power consumption may enable a quick setup and deployment and is energy efficient. The functional aspects of on-platform pumps for the MPS systems are given in Table 3.

TABLE 3

Functional requirements for on-platform pumps to transport biological fluids.

| Parameter | Value | Description |
|---|---|---|
| Flowrate precision | ≤±5% | Deterministic flow volume against varying back-pressures allows to use the pumps in dosing applications and where precise amounts of fluids need to be transported. Accurate flow control against varying conditions helps in multi-organ interaction studies. |
| Flow-rate range | 0.001-0.01 μL/s (or) 1-5 μL/s | There are two distinct ranges for the flow-rates. The flow from the mixer to various MPS occurs at low flowrates while the perfusion and recirculation occurs at the higher range of flowrates. Low pulsation flow profiles are preferred. |
| Back-pressure capability | 20 kPa | Pump a constant volume flowrate for given actuation condition, up till the back-pressure rating. Back-pressure arises due to resistance from internal channels and destination wells, and the tissue-scaffold support structures. These values are determined experimentally. |
| Biocompatibility and no drug-adsorption | — | Do not modify the physical or chemical properties of the media or cells. All the fluid surfaces that the fluid comes in contact with should be sterile and bio-compatible. Lipophilic (high logD), small molecule drugs should not be adsorbed to maintain accurate low concentrations in the system. |
| Self-priming, and bubble-tolerant | — | Evacuate air inside and create enough suction to fill with fluid even when started dry. Bubbles should not affect the pump performance. |
| Energy efficiency, and bi-directional flow | — | For portable systems, energy efficiency should be maximized. Bi-directional pumping is desirable, especially while seeding cells on the tissue scaffolds. |
| Long-term reliability, and scalability | — | The platforms run in the incubator for up to 4 weeks at a time and should be capable of multiple such runs at the same performance. They should be small enough to assemble multiple pumps on a single platform. |

The requirement of sterility places restrictions on the types of pumping schemes that can be used. A clear method of containing the biological media and acting through a membrane or directly using component forces is described.

Using component forces requires manipulation of a field which can act directly on the fluid at a distance. For contact volume flow-rates under back-pressure, some form of valving is needed. Suitable pumps with valving include diaphragm pumps as they intrinsically have valves in the valve-pump-valve design.

A comparison between the functional aspects of pumps and valves are given in Table 4. The pumping designs may include pump-pump-pump or a valve-pump-valve configurations, as described in Table 5.

TABLE 4

Different functional aspects for pumps and valves.

| | Pumps | Valves |
|---|---|---|
| Action time | Controlled motion for low pulsatility while discharge. Suction is typically fast. | Fast action for opening and closing. |
| Displaced volume | Most of the pumped volume per stroke typically comes from discharge of the pump chamber. | Minimize volume displacements during actuation. |
| Force | The force required to deflect the diaphragm subtracted from the actuation force is the force into the fluid. Volume determinism required bounding of the pump diaphragm deflection | Force required to deflect the diaphragm till it seals the sealing lands is the minimum actuation force to seal the valve. |

TABLE 5

Pump-pump-pump vs. valve-pump-valve configuration of pumping.

| | Pump-Pump-Pump | Valve-Pump-Valve |
|---|---|---|
| Design Considerations | Multiplexed design requirements. For deterministic volume flow rate, each chamber typically seals as well as displaces significant fluid volume. | Specialized design requirements. For deterministic volume flow rate, valve chambers seal and rectify the flow while pump chambers transfer energy into the fluid. |
| Manufacture | Relatively easier due to only one chamber profile | More complex manufacturing due to different profile. |
| Power Efficiency | For deterministic volume flow rates, only the volume displaced by the last pump chamber is important. If valves consume lesser energy, then this is less efficient. | Lower power consumption with efficient valves designs. |

1. Pump Components and Actuation

Described are different methods to transfer energy into fluid to cause pumping, different embodiments for valve geometries, pump chamber geometries, pumps (including diaphragm pumps), methods of actuation, actuators, and membrane sealing. Also described are combinations of any one of the embodiments for valve geometries, pump chamber geometries, pumps (including diaphragm pumps), with any one of the methods of actuation, actuators, and membrane sealing. For example, any one of valve geometries, pump chamber geometries, or pumps described herein may be used with any one method of actuation or actuators to provide pumps with efficient pumping of fluid. Pumps with efficient pumping of fluid include pumps that have at least one of the functional aspects described in Table 3.

a. Methods to Transfer Energy to Fluid

Provided are different methods to transfer energy into fluid to cause pumping. Typically, the flow is rectified using valves, which is achieved (1) through deforming a membrane, (2) sliding element like a piston, (3) constrained volume where the chamber geometry moves and at the same time changes shape and size, causing pumping, (4) deformation of some element submerged in the fluid volume. The element can be activated thermally (bubbles), magnetically (magnetostritive materials—Magnetic Shape Memory Alloys), or electrically (electroactive polymers) (5) deformation of walls of the chamber like in peristaltic pumps.

b. Diaphragm Actuation i. Diaphragm Pump Embodiments

One embodiment of diaphragm pumps includes a direct mechanical contact with the membrane to actuate the diaphragm. The membrane makes contact with the sealing lands, closing them. This embodiment may include an elastomeric pusher in contact with the diaphragm. The diaphragm state needs to be restored after deflection. One way to restore the diaphragm state is to rely on the diaphragm stiffness. This is described in FIGS. 4A-4D.

ii. Bi-Directional Actuation of Membrane

Figure 6A:
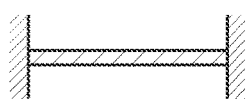
FIGS. 6A-6I are different embodiments for bidirectional actuation of membrane.
Figure 6B:
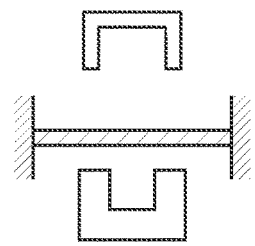
Figure 6C:
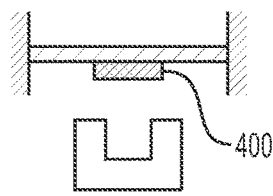
Figure 6D:
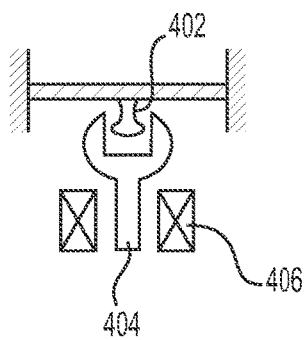
Figure 6E:
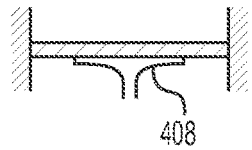
Figure 6F:
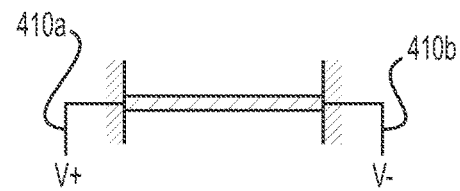
Figure 6G:
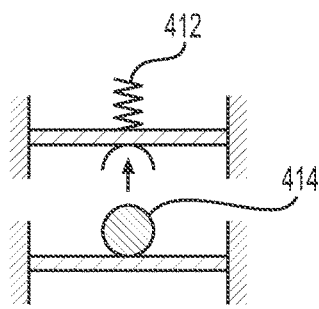
Figure 6H:
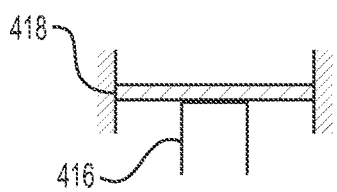
Figure 6I:
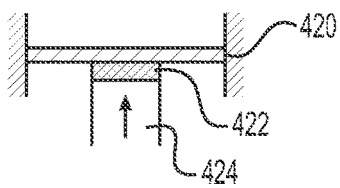

Embodiments for bidirectional actuation of membrane include (1) biasing with pressure or vacuum, which may allow to push or pull the membrane, (2) if the membrane material is magnetic or it is coated or embedded with magnetic particles, a varying electromagnetic field may be used to push or pull on the membrane, (3) a magnet attached to the membrane, a varying electromagnetic field may be used to push or pull on the membrane, (4) a clamp that clamps onto the holding structure on the membrane and makes the membrane move along with the actuator, (5) a vacuum cup makes a temporary bond with the membrane, (6) piezo-actuators, which can actuate in either direction by modulating the sign of the actuation signal, (7) some spring element placed within the fluidic side, which stores energy and assists the membrane return, (8) temporary bonding, such as those activated by UV light, could bond the pusher with the membrane, (9) a combination of embodiments 2, 3, and 4 may be a soft-magnetic material in the membrane that attaches to a permanent magnet on the pusher giving a temporary bond. This is described in FIGS. 6A-6I. FIG. 6A shows biasing with pressure or vacuum allows to push or pull the membrane, FIG. 6B shows the membrane material may be magnetic or it is coated or embedded with magnetic particles, or a magnetic mesh. A varying electromagnetic field may be used to push or pull on the membrane. FIG. 6C shows a similar embodiment to that in FIG. 6B with a magnet 400 attached to the membrane. FIG. 6D shows a clamp 404 clamps onto the holding structure 402 on the membrane and makes the membrane move along with the actuator 406. FIG. 6E shows a vacuum cup 408 makes a temporary bond with the membrane. FIG. 6F shows piezo-actuators 410a and 410b actuate in either direction by modulating the sign of the actuation signal. FIG. 6G shows a spring element 412 or a deformable ball 414 placed within the fluidic side stores energy and assists the membrane return. FIG. 6H shows a temporary bonding such as the ones which are activated by UV light could bond the pusher 416 with the membrane 416. FIG. 6I is an embodiment combining the aspects shown in FIGS. 6B, 6C, and 6D. A soft-magnetic material 422 in the membrane 420 attaches to a permanent magnet 424 on the pusher giving a temporary bond.

iii. Diaphragm Actuation with Mechanical Contact

Provided are valve and pump features for diaphragm actuation with mechanical contact. One feature is a conical pump chamber, which allows for a progressive, determined deflection front of the membrane. Another feature is a valve with a fluid port from the top which acts as the sealing surface, another feature are mid-wall valves with a middle wall extending downwards, which provides a well-defined region of sealing with lower fluid volume displacement per stroke compared to a valve with a fluid port.

Another embodiment for direct mechanical contact with the membrane to actuate the diaphragm is a stiff plastic blister pack, which may contain hydraulic fluid. In this embodiment, a spherical cap is pushed down and pressurizes the hydraulic fluid within the system which actuates the diaphragm at pumps and valves. The return of the diaphragm is by its own stiffness, or any of the embodiments for the bidirectional actuation of the membrane. A benefit of this embodiment is a higher packing density of the pneumatic ports and the actuation of multiple diaphragms in parallel. For this embodiment sealing of hydraulic fluid under pressure may be needed.

This embodiment may include a hydraulic plate docking onto a docking station with EM actuators. This embodiment may include a hydraulic plate incorporated into a docking station with EM actuators and form the bottom plate. The hydraulic plate may be an intermediate between the fluidic plate and the EM actuators on the docking station. The hydraulic plate, as an intermediate hydraulic bottom plate or as incorporated into the bottom plate, may optionally have a cap contacting at least one region of the rotor or the mover of the EM actuator. Deformation of the cap increases pressure of the hydraulic fluid in the hydraulic plate causing the deformation of the diaphragm.

Figure 5A:
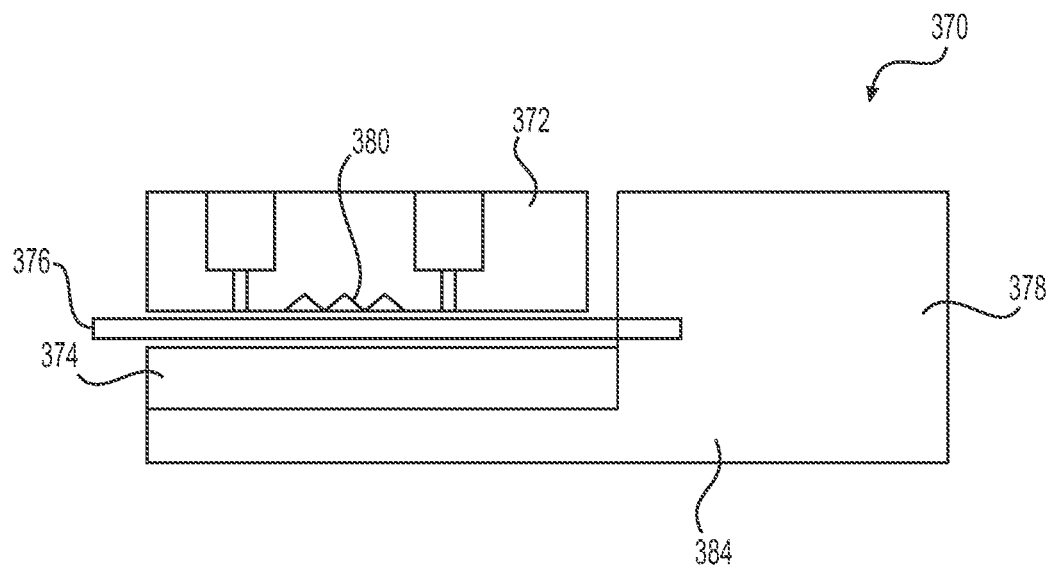
FIGS. 5A, 5B, and 5C are diagrams showing a pump embodiment with EM actuators and hydraulic ports.
Figure 5B:
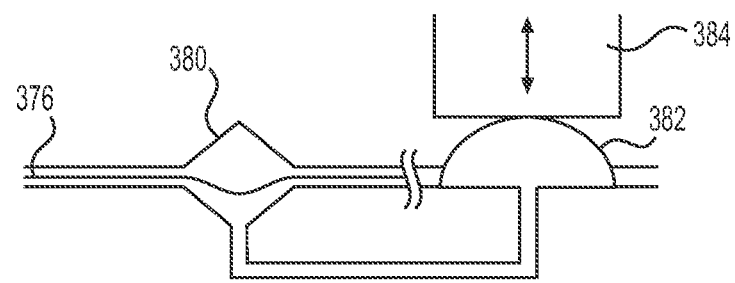
Figure 5C:
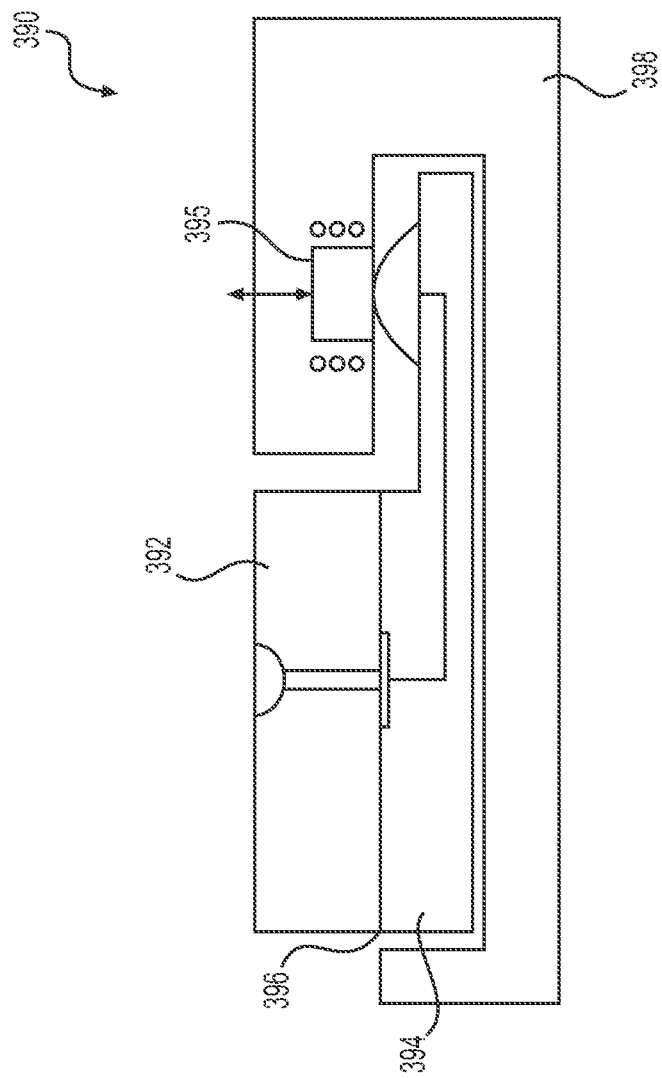
Figure 7A:
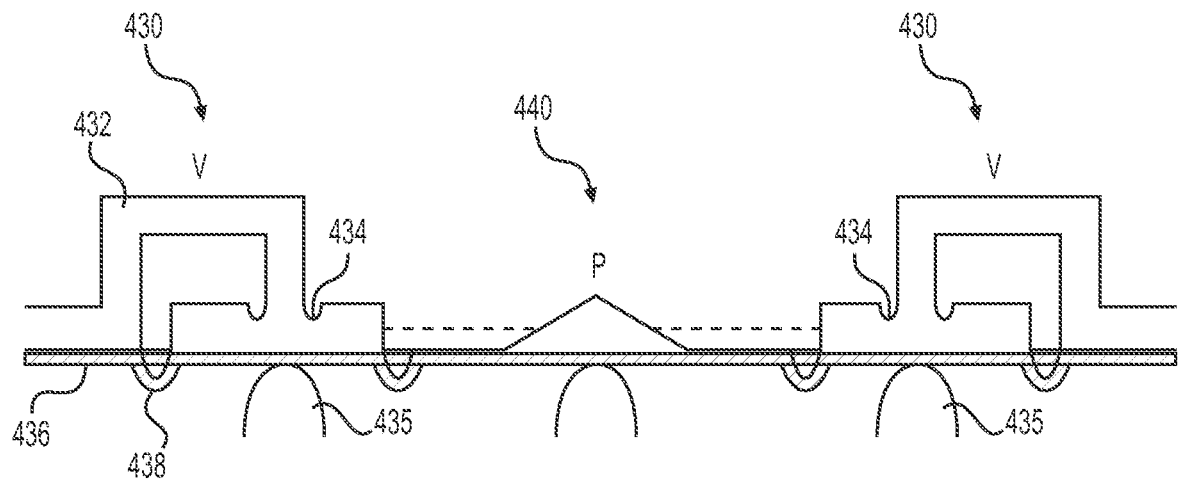
FIGS. 7A and 7B are diagrams showing section views of valve and pump features for diaphragm actuation with mechanical contact.
Figure 7B:
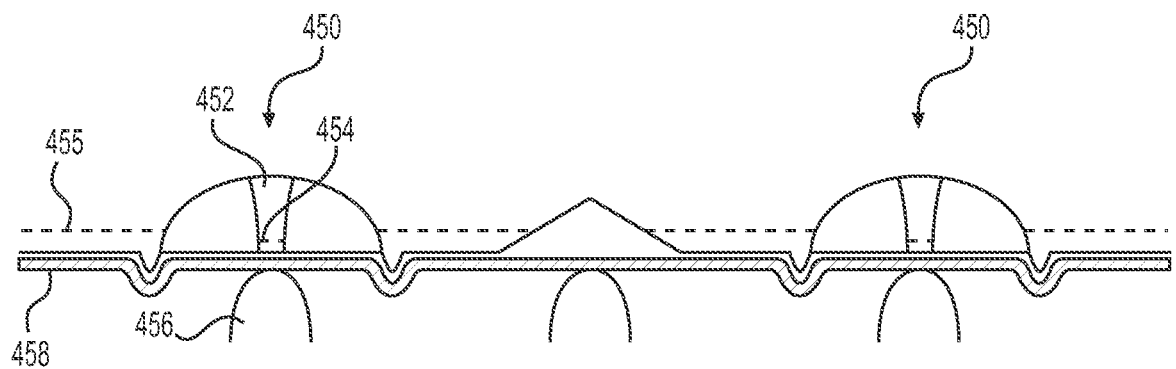

This is described in FIGS. 5A-5C. FIG. 5A shows a platform 370 with the fluidic plate 372 and pump chamber 380 positioned above a hydraulic stage 374. A membrane 376 separates the fluidic plate 372 from the hydraulic stage 374 incorporated into a pump block 378 containing EM actuator 384. FIG. 5B shows the EM actuator 384 actuating a stiff cap 382 (hydraulic) fluidically connected to the membrane 376. The stiff cap 382 may be a plastic blister pack containing hydraulic fluid. In these embodiments, the spherical stiff cap is pushed down and pressurizes the hydraulic fluid within the system which actuates the membrane at pumps and valves. The return of the diaphragm is by its own stiffness or by use any of the concepts described in FIG. 6A-6I. A benefit is higher packing density of the pneumatic ports and the actuation of multiple diaphragms in parallel. The hydraulic fluid is typically sealed under pressure. FIG. 5C shows an alternative embodiment for a platform. Here, the platform 390 includes a fluidic plate 392, a membrane 396, and a pre-made hydraulic plate 394. The pre-made hydraulic plate 394 with the fluidic plate 392 and a membrane 396 dock onto a docking station 398 containing EM actuators 395. In these embodiments, diaphragm is actuated by a minimally-compressible fluid such as water. This configuration offers good conformance of the sealing diaphragm (membrane) to the valve or pump chamber, flexibility in actuator positioning and the potential for push-pull action. Push-pull version of actuating the diaphragm is by using a vacuum or magnetic force for pre-loading (pulling the diaphragm) or by bonding the pusher to the diaphragm to enable push-pull motion. A compact embodiment of the pump and valve features for diaphragm actuation with mechanical contact is a pump with slots in the walls partitioning the valve and pump chambers, which allow fluid flow but also prove a boundary to the membrane during deflection. This embodiment may require positioning the actuators under each valve and pump chamber, to actuate pressure fingers under pump and valve chambers. This is described in FIGS. 7A and 7B. Conical pump chamber 440 allows for a progressive, determined deflection front of the membrane. FIG. 7A shows a valve 430 with ridges 436 and a fluid port 432 from the top which acts as the sealing surface providing sealing lands 434. The ridges 436 pre-stress the membrane 438 for quicker return to neutral position. A circular profile to the pusher 435 is profiled to match the sealing lands 434. The pusher 435 may be an elastomer or a cantilever flexure. FIG. 7B shows mid-wall valves 450 with a middle wall 452 extending downwards which provides a well-defined region of sealing, sealing region 454, with lower fluid volume displacement per stroke compared to that generated by valve 430. The membrane 458 is pushed by a pusher 456 shaped to match the sealing region 454.

iv. Rigid Diaphragms

Provided are also rigid diaphragms, which have the advantage that the spring force can be precisely determined by the curved sections. Such diaphragms have significant stiffness at the neutral position as compared to a flat diaphragm. The fluidic sealing with the fluid channels and the valve and pump chambers may be achieved by bonding the membrane with the fluidic side or using another softer material (such as a gasket) for sealing and using the diaphragm only for force transmission to the fluid.

c. Valve Embodiments

Additional valve embodiments that do not use a membrane are also described. The alternate valve embodiments may use (a) an elastomer gel conforming to the cavity and sealing the channel; (b) a duckbill geometry of the valve, which is normally closed and opens when actuated; or (c) an elastomer as a hydraulic piston. Pushing from the top loads the elastomer in a hydrostatic stress state and causes longer deformation at the bottom, sealing the channel. These valves may reduce the volume of fluid displaced when compared to that during actuation of diaphragm valves. This also requires sealing of the biological fluid during which the material of elastomer contacts with the fluid. Therefore, biocompatible elastomers are preferred.

When open, a valve allows free flow of fluid and when closed, seals the fluid flow. Sealing may be accomplished either by contact with sealing lands, or by greatly increasing the flow resistance through the valves. For sealing by local deformation at the contact, a combination of soft and hard material or two smooth surfaces may be used.

In another valve embodiment, a porous material allows fluid to flow through with low resistance. When acted upon by a field, such as temperature, or electromagnetic fields, the material swells thereby shrinking the pores and the flow-through stops. In another embodiment, a valve sealing may be achieved with multiple sealing lands in one valve chamber. Valve sealing may be established by concentric rings at which the membrane makes contact with the sealing lands.

In another valve embodiment, sealing may be achieved using rolling sealing by an active element. The active element rolls into the sealing cavity and seals by pushing the membrane against the sealing lands. Sealing may be done either through a membrane, some element within the fluid, or by deforming an elastomer.

In another valve embodiment, a mechanism for latching of valves may be used. This embodiment uses over-center mechanisms, such as rigid links attached to an element with contoured surface and springs, which latch into position and which thus only require energy to switch their state. Another example is a cantilever flexure. Stiffness of the metal cantilever flexure pushes the membrane down by default, keeping the valve open, and the cantilever may be pulled up by EM force, closing the valve. Latching can either be achieved fluidically as in macroscale pilot valves, or using a coined membrane which flips to either side, or within the actuator mechanism.

d. Pump Embodiments

Provided are various pump embodiments.

In one embodiment, the pump may be a magnetic material embedded in an elastomer, which can be acted upon from a distance to produce a force and a deflection in the elastomer. Another way may be to push an elastomer in a large area region and amplify that deflection over a smaller area. Embodiments for valve actuation by elements inside the fluid are also described. For example, a pump using internal elements may be used. A field, such as temperature, or electric/magnetic field, acts at a distance and causes deformation in the pump chamber material. Valves rectify the flow to cause net pumping of fluid volume.

Figure 8A:
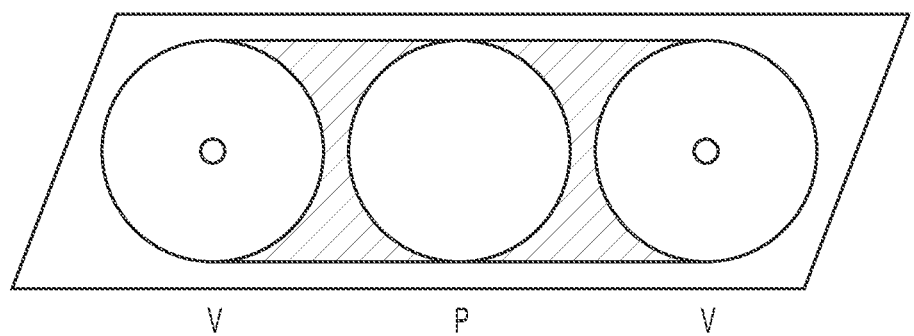
FIGS. 8A, 8B, and 8C are diagrams showing a compact embodiment of a valve (V)-pump (P)-valve (V) arrangement shown in FIGS. 7A and 7B.
Figure 8B:
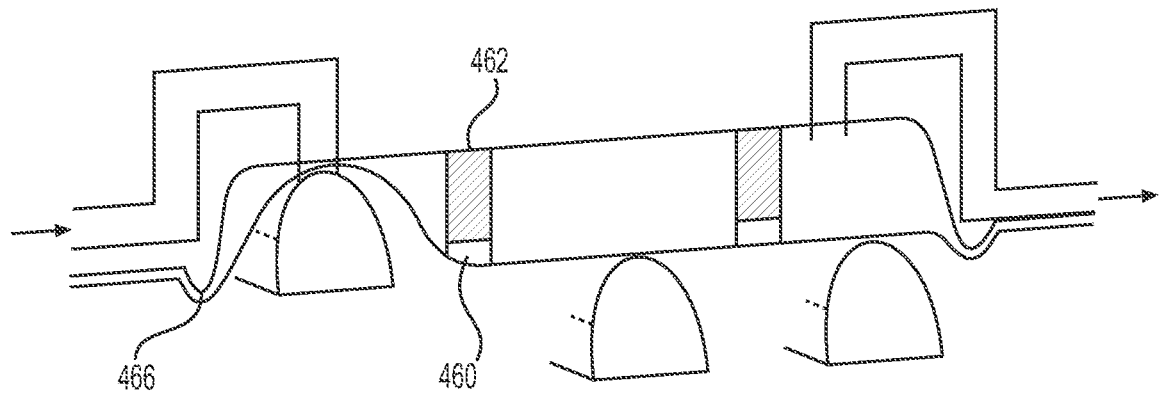
Figure 8C:
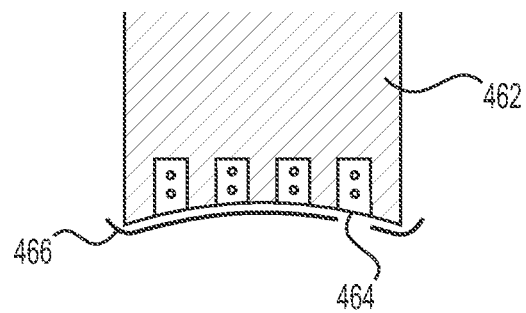

A compact embodiment of the pump and valve features shown in FIGS. 7A and 7B: instead of fluid channels, there are slots in the walls partitioning the valve and pump chambers which allow fluid flow but also prove a boundary to the membrane during deflection. Placement of actuators close to each other is needed. This is described in FIGS. 8A, 8B, and 8C. FIGS. 8A, 8B, and 8C are diagrams showing a compact embodiment of a valve (V)-pump (P)-valve (V) arrangement shown in FIGS. 7A and 7B. FIG. 8A is a plan view and 8B is a section view showing that instead of fluid channels, there are slots 460 in the walls 462 partitioning the valve and pump chambers which allow fluid flow but also prove a boundary to the membrane during deflection. FIG. 8C shows an enlarged cross-section view of walls 462 with channels 464 thin enough that the membrane 466 cannot bend.

Tandem pumps in which both directions of the diaphragm actuation are utilized are described. The valving can be passive (uni-directional flow) or active (bi-directional flow). A benefit is a smoother flow-profile due to tandem operation. During each half of the stroke, one side of the chamber is pumping while the other is in suction. This reduces the gap between subsequent pulses in the flow profile, thereby reducing the overall pulsatility. The materials may be biocompatible. Coated piezoelectric diaphragms may be used.

Another embodiment is a rotating cylinder pump. Motors can be power-efficient, and small motors are commercially available. A force may be applied at a distance through magnets or by direct mechanical contact. The actuation frequency of the pump may be determined by the rotation speed of the cylinder and the phasing may be determined by the relative placement of the magnets and fingers around the circumference.

Another embodiment is a tandem nozzle-diffuser pump. In each stroke of an oscillating actuator, there is net fluid flow at the outlet. This may help to reduce the pulsations. The two pump diaphragms are the only active elements. There may be some back-flow and the volume is non-deterministic. The operation of the tandem nozzle-diffuser pump is typically uni-directional.

In another embodiment, a single actuator is provided for sealing both valves. A shaped elastomeric material facing two side-by-side valve ports is typically used. When the elastomer is to the left it seals the left valve and opens the right. When the elastomer is to the right, it opens the left valve and closes the right. In one example of this embodiment, the fluid channels and the pump diaphragm are in a plane and the valve sealing actuator acts perpendicular to this plane and seals at the sealing locations. The benefit is that it reduces the requirement of the number of actuators. The pump may be actuated by a single actuator if the valves and the pump diaphragm can be synchronized. An effective sealing of the valves may be required to prevent back-flow when the valve actuator switches state.

Another embodiment is a ball-bearing pump. In this embodiment, a circular tube with recirculating ball bearings positioned at a predetermined distance from one another is used. The pump is a tube fluidically connected to the tube with ball bearings. As one ball stops in the tube pump, the one in front keep moving to evacuate the fluid, and the cycle continues. Fluidic sealing occurs between the ball surfaces and the tube inner walls. The volume of fluid captured between two balls is fixed, and this is a positive displacement pump.

The balls in the circular tube may be actuated using permanent magnets attached to a rotating DC motor. Volume determinism comes from the deterministic spacing between the balls. The ball-bearing pump typically operates without valves. A single actuator with magnets from the outside of the circular tube can actuate the balls. Slightly oversizing the balls with respect to the inner diameter of the tubing may provide improved sealing.

e. Membrane Sealing
i. Pump Chamber

Figure 9A:
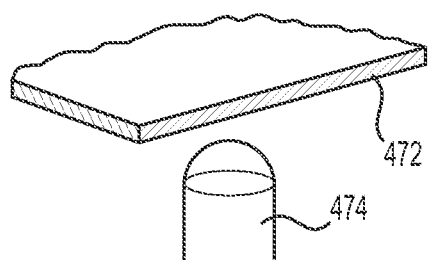
FIGS. 9A-9E are diagrams showing membrane contact in a pump chamber 470.
Figure 9B:
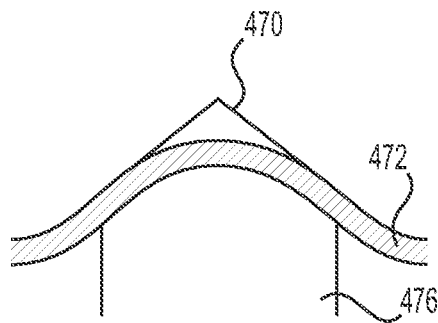
Figure 9C:
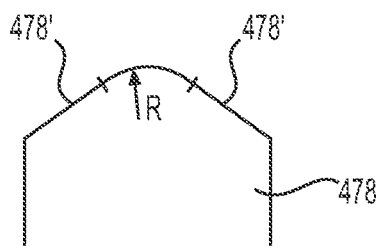
Figure 9D:
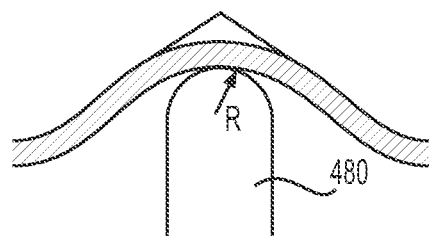
Figure 9E:
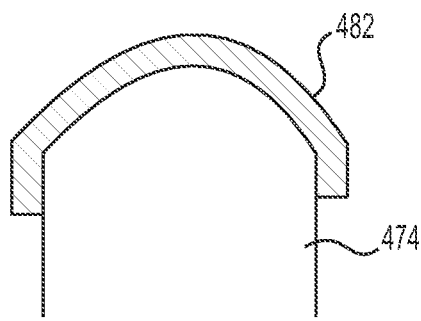

Described are also different embodiments of the membrane contacting the pump chamber to seal the chamber. A pushing element, such as a plunger, pin, button, finger, or pusher, may be used to push and deflect the membrane into the pump chamber. The contact mechanics of the pushing element is an important consideration. A circular shaped pin for the pump geometry may be such that when the membrane bottoms out, the geometry is well defined, and so is the displaced volume. Stress concentrations at the contact point may be avoided by a thin layer of soft elastomeric material between the pusher and the membrane which gets loaded in a hydro-static stress state and helps distribute the pressure more evenly. This is described in FIGS. 9A-9E. FIGS. 9A-9E are diagrams showing membrane contact in a pump chamber 470. A circular shaped pin for the pump geometry such that when the membrane bottoms out, the geometry is well defined, and so is the displaced volume. Stress concentrations at the contact point can be avoided by a thin layer of soft elastomeric material 482 between the pusher 474 and the membrane 472, which gets loaded in a hydro-static stress state and helps distribute the pressure more evenly (FIG. 9E). The pushing element 476 may be of a conformal shape to match how the membrane 472 would deform under pressure (FIG. 9B). The pushing element may be a spherically shaped pin 480 with radius R (FIG. 9D). The pushing element 478 includes a radius R as well as flat surfaces 478' to provide a slightly more angle to make it contact deterministic, and match the cone angle of chamber (FIG. 9C).

ii. Valve Chamber

Described are also different embodiments of the membrane contacting the valve chamber. Typically, the membrane needs to make contact with the sealing lands and deforms locally at the contact point to seal. For this, it is preferred to have an even pressure from the other side of the membrane pushing towards the sealing lands. This may be achieved by placing a relatively thick layer of soft elastomer between the pusher and the membrane. In operation, the elastomer gets loaded in a hydro-static stress state and helps distribute the pressure evenly to cause sealing.

iii. Actuator Interfacing with Membrane

Another embodiment for membrane sealing is an actuator interfacing with the membrane. If the membrane is clamped, then the pushing pin needs to clear the thickness of the lower clamped layer. If the pushing pin becomes too long, it will be slender. The pusher may be made more rigid by giving it a conical shape. If the membrane is bonded to the fluidic side, it gives more flexibility for the actuators on the other side of the membrane. The diaphragm may connect to the top plate, the bottom plate or both using bonding, such as adhesive, solvent, thermal, anodic, and/or chemical bonding, or clamping, such as mechanical clamping, clamping using fluidic pressure, and/or clamping using vacuum.

It is important to achieve adequate sealing of membranes, especially in clamped membranes. A well-defined sealing line may be modeled and defined. Compression of the membrane may be geometrically determined and the sealing force from the deformation of the membrane may be determined by Hooke's law.

In another embodiment, membrane sealing may be achieved with gaskets. Gaskets take most of the compression, and may be used in case of rigid and stiff membranes. The total clamping force=deformation of gasket×gasket stiffness.

In some embodiments, an injection molded single-use platform, incorporating a top fluidic plate, a bonded membrane, and a bottom plate, includes conical pump chambers, and the mid-wall valve configuration described above.

The membrane sealing provided by the different embodiments of valves, pumps, and diaphragm actuation typically achieves a wall contact pressure between about 1 kPa and about 200 kPa, between about 10 kPa and about 200 kPa, between about 10 kPa and about 150 kPa, between about 10 kPa and about 100 kPa, such as about 1 kPa, about 10 kPa, about 25 kPa, about 50 kPa, about 75 kPa, about 100 kPa, about 125 kPa, about 150 kPa, about 175 kPa, or about 200 kPa.

The membrane sealing provided by the different embodiments of valves, pumps, and diaphragm actuation typically a force at wall contact between about 50 mN and about 800 mN, between about 100 mN and 700 mN, between about 125 mN and about 700 mN, between about 150 mN and about 550 mN, such as about 100 mN, about 125 mN, about 150 mN, about 200 mN, about 250 mN, about 300 mN, about 325 mN, about 350 mN, about 400 mN, about 450 mN, about 500 mN, about 525 mN, about 550 mN, about 600 mN, about 650 mN, about 700 mN, about 750 mN, or about 800 mN.

2. Actuation Means for Diaphragm Pumps

The actuation means for operating a diaphragm in pumps of the organ-on-chip platforms include actuating means with forces such as peristaltic (e.g., diaphragm, tube, surfaces on contact with fluid), rotary, piston (e.g., syringe, vacuum), gas boundary, phase-change, ferro-fluid, surface tension (e.g., electrowetting, capillary), surface acoustic wave, viscous (e.g. rotating disc, rotating screw), osmosis, gravity driven pumps, electrohydrodynamic, electroosmotic, electrokinetic, or magnetohydridynamic, electromagnetic, and centrifugal forces.

In preferred embodiments, the actuating means are electromagnetic (EM) actuators. The electromagnetic actuators may mechanically contact the membrane in valves and pumps. This may be achieved by the EM actuators moving mechanical pins, or push-buttons, which contact the membrane. The EM actuators may also switch pneumatic channels between pressure and vacuum. This may achieved by the EM actuators switching between pressure and vacuum in pneumatic ports connected to valve and pump chambers. The EM actuators may also compress/expand fluid to create pressure and vacuum. This may be achieved by the EM actuators compressing or expanding cylinders to generate pressure or vacuum in the pneumatic and/or hydraulic ports connected to pump and valve chambers.

The actuation means typically provide operating pressure between about 5 kPa(g) and about 400 kPa(g), between about 10 kPa(g) and about 375 kPa(g), between about 10 kPa(g) and about 350 kPa(g), between about 10 kPa(g) and about 300 kPa(g), between about 10 kPa(g) and about 250 kPa(g), between about 10 kPa(g) and about 200 kPa(g), between about 10 kPa(g) and about 150 kPa(g), between about 10 kPa(g) and about 100 kPa(g), such as about 5 kPa(g), about 10 kPa(g), about 25 kPa(g), about 40 kPa(g), about 50 kPa(g), about 75 kPa(g), about 100 kPa(g), about 125 kPa(g), about 150 kPa(g), about 175 kPa(g), about 200 kPa(g), about 225 kPa(g), about 250 kPa(g), about 275 kPa(g), about 300 kPa(g), about 325 kPa(g), about 350 kPa(g), about 375 kPa(g), or about 400 kPa(g).

C. Electromagnetically Actuated Micro-Pump

Described are electromagnetically actuated micro-pumps (EM micro-pumps) containing at least one electromagnetic actuator (EM actuator) and at least one pump formed of any one valve or pump embodiments, or any combination of the valve and pump embodiments, described above. The EM actuators in the EM micro-pumps provide sufficient force capability for a pre-determined membrane material and chamber geometry to deflect the membrane till it touches the chamber walls and seals the chamber preventing fluid flow.

1. EM Micro-Pump Structure

Provided are structure, elements, materials, and dimensions for a scaled-up version of an EM actuator for the EM micro-pump. The dimensions described for each of the elements of the scaled-up version of the EM actuator may be reduced by any scale down factor between 0.95 and 0.01, such as 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, or 0.01 to obtain operable EM micro-pumps. The dimensions described for each of the elements of the scaled-up version of the EM actuator may be increased by any scale up factor, such as a scale up factor between 1.5 and 10, such as 1.5, 2, 2.5, 3, 3.5, 4, 4.5, 5, 5.5, 6, 6.5, 7, 7.5, 8, 8.5, 9, 9.5, or 10 to obtain operable EM pumps. The Examples below present modeling which may be used to scale down or to scale up the elements of the disclosed EM actuators.

The scaling may be isometric, affecting all the elements of the EM actuators and pump similarly, or non-isometric. In non-isometric scaling, some elements change in dimensions and function, while others remain unchanged. For example, the size of the magnets may remain unchanged, while the winding may reduce or increase based on the force needed for actuation. Also, a change in diaphragm diameter requires a non-isometric scaling of EM pump elements. As the diaphragm diameter decreases, the tension in the diaphragm increases, and a greater force will be required from the EM actuators to deflect the smaller diaphragm.

a. EM Actuator Structure

The EM micro-pumps typically include an EM actuator containing a stator, at least one pair of permanent magnets, a rotor or a mover, winding, one or more flexures, contact spring, and a push button. In some embodiments, the EM actuators include at least one pair of push buttons. The push buttons are configured to contact a membrane. The actuation of the membrane with the EM actuator provides the actuation force for moving fluid in the fluidic plate of the OOC platforms.

i. Stator

Typically, the stator is a body with a three-dimensional shape and an axis of symmetry. The stator typically includes at least one set of two protruding portions in opposition to one another and symmetrical to one another along the axis of symmetry. The body may include more than one set of the two protruding portions, such as two sets, three sets, four sets, etc. The body may have a cross-sectional area in the shape of pyramid, an oblong, a square, a rectangle, a circle, or any other shape.

The stator may be a U-shaped body, having two legs and a connecting region. The stator may be a body having interconnected two or more U-shaped bodies. The cross-section of the legs may be square with a side length substantially similar to the diameter of the pump membrane. For example, a square of 3/16" (4.763 mm) side may be the cross-section for the stator as the pump diameters are 4-5 mm. To avoid crosstalk between the magnets, the legs may be spaced at a width at least between 2, 3, 4, 5, 6, 7, 8, 9, or 10 times, and up to 20, 21, 22, 23, 24, or 25 times, the leg width. For example, the legs may be spaced at a width between 2 and 25 times, between 2 and 24 times, between 2 and 23 times, between 2 and 22 times, between 2 and 21 times, between 2 and 20 times, the leg width, such as 2, 3, 4, 5, 6, 7, 8, 9, 10, 11, 12, 13, 14, 15, 16, 17, 18, 19, 20, 21, 22, 23, 24, or 25 times the leg width. The permanent magnet typically have most of the flux going through the stator and the rotor. This minimizes the closing of magnetic flux from the permanent magnet through air before reaching the stator leg on the other side (FIGS. 12A-12F). The length of the legs may be at least 2, 3, 4, 5, or 6 times, and up to 15, 16, 17, 18, 19, or 20 times, the width of the magnet so that the connecting segment of the "U" is far away from the permanent magnet (PM) compared to the rotor. For example, the length of the legs may be between 2 and 20 times, between 2 and 19 times, between 2 and 18 times, between 2 and 17 times, between 2 and 16 times, between 2 and 15 times, the width of the magnet, such as 2, 3, 4, 5, 6, 7, 8, 9, 10, 11, 12, 13, 14, 15, 16, 17, 18, 19, or 20 times the width of the magnet.

The stator may be formed of any magnetic material with relative permeability significantly greater than air. For example, the stator may be formed of low carbon steel, medium carbon steel, or high carbon steel. Low-carbon steel composition includes between about 0.05% and about 0.25% carbon and up to 0.4% manganese. Carburizing may be used to increase its surface hardness. Medium carbon steel has a composition of between about 0.29% and about 0.54% carbon, with between about 0.60% and about 1.65% manganese. Medium carbon steel is ductile and strong, with long-wearing properties. High carbon steel has a composition of between about 0.55% and about 0.95% carbon, with between about 0.30% and about 0.90% manganese. It is very strong and holds shape memory well.

ii. Permanent Magnets

Figure 13A:
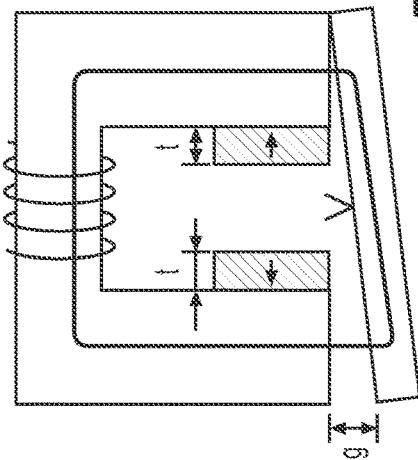
Figure 13B:
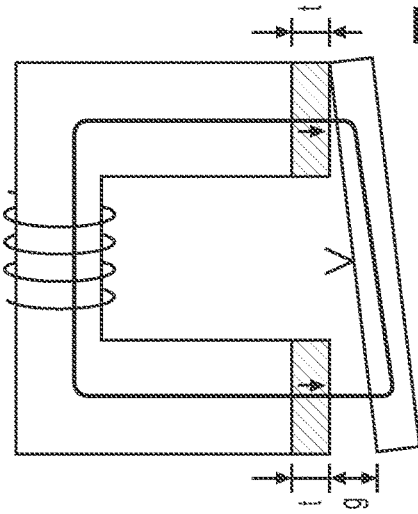
Figure 13H:
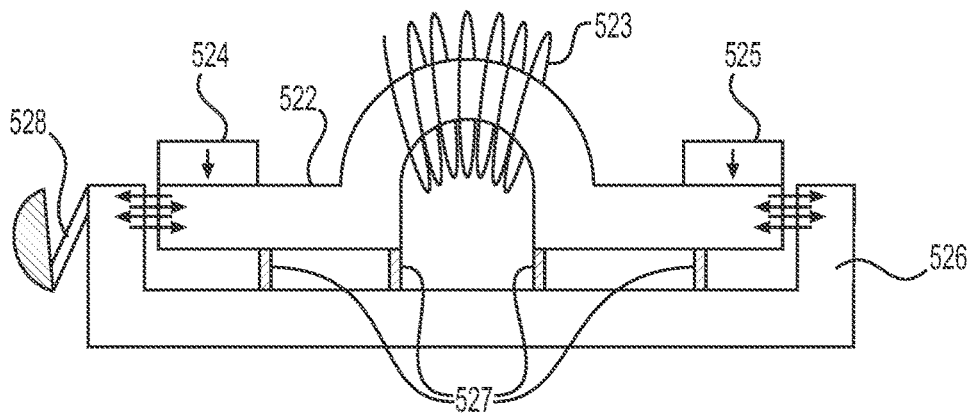
Figure 13I:
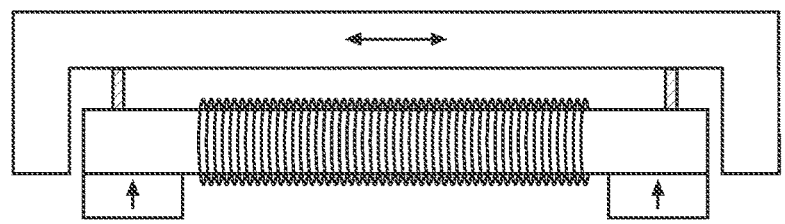
Figure 13J:
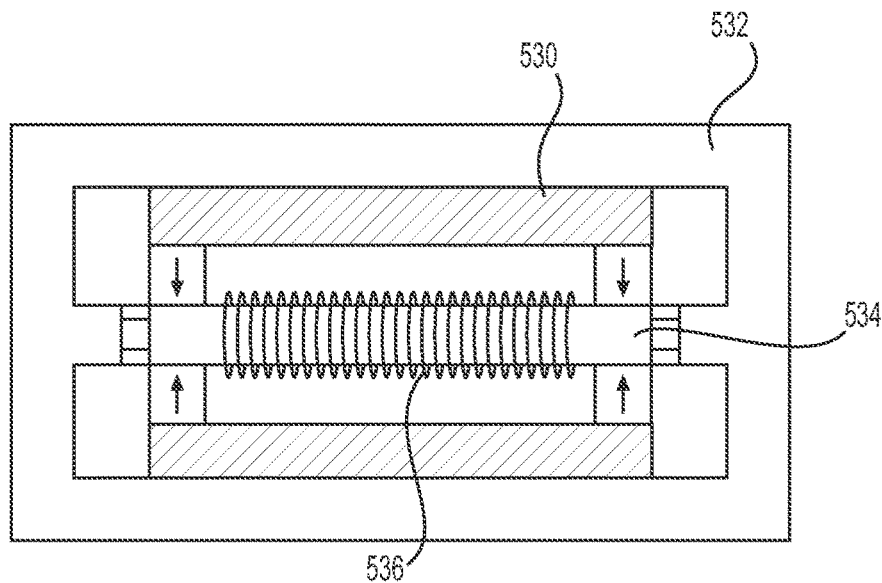

Typically, each of the stator protrusions, such as the stator legs, typically include a permanent magnet. The permanent magnet may be positioned on any of the surface of the stator leg, but is usually positioned at the end of the leg. Each of the permanent magnets on the leg of a stator forms a pole face. The permanent magnets provide the latching force at each pole face of the stator to hold the rotor in contact without any additional power input. The permanent magnets therefore, lead to bi-stability of the actuator. They may be bonded to the stator using cyanoacrylate (Henkel LOC-TITE® 408 (Henkel IP & Holding GMBH, Germany) adhesive. The permanent magnets are typically attached to the side of the stator legs so that the permanent magnets themselves do not become a part of the main magnetic circuit. Since the permanent magnet has an incremental permeability of $\mu_0$, it acts as an air-gap, which would increase the reluctance in the circuit. Most of the reluctance in the magnetic circuit typically comes from the working air-gap between one end of the rotor and the stator pole face. The different embodiments for the position of the permanent magnets on the stator and the different embodiments for stator and rotor geometries are presented in FIGS. 13A-13J and 14. FIGS. 13A-13J are diagrams showing a stator body with two protruding legs and the different embodiments of positioning the permanent magnets on the stator legs. The rotation of the rotor between the stator pole faces is also shown. Permanent magnets are inline in the magnetic circuit (FIGS. 13A and 13E), the permanent magnets are placed by the side of the legs facing the interior of the actuator (FIGS. 13B and 13C), the permanent magnets are placed by the side of the legs facing the exterior of the actuator (FIG. 13D). FIG. 13F shows an angled stator with a linear actuator. Bending the stator and bringing the pole faces further apart converts it into a linear actuator. FIGS. 13G-13I show different embodiments of stator and rotor arrangements to form a linear actuator. FIG. 13J shows an embodiment with a cylindrical form factor with bushing 530 between the outer rotor 532 and the internal stator 534, with the windings 536.

Figure 14:
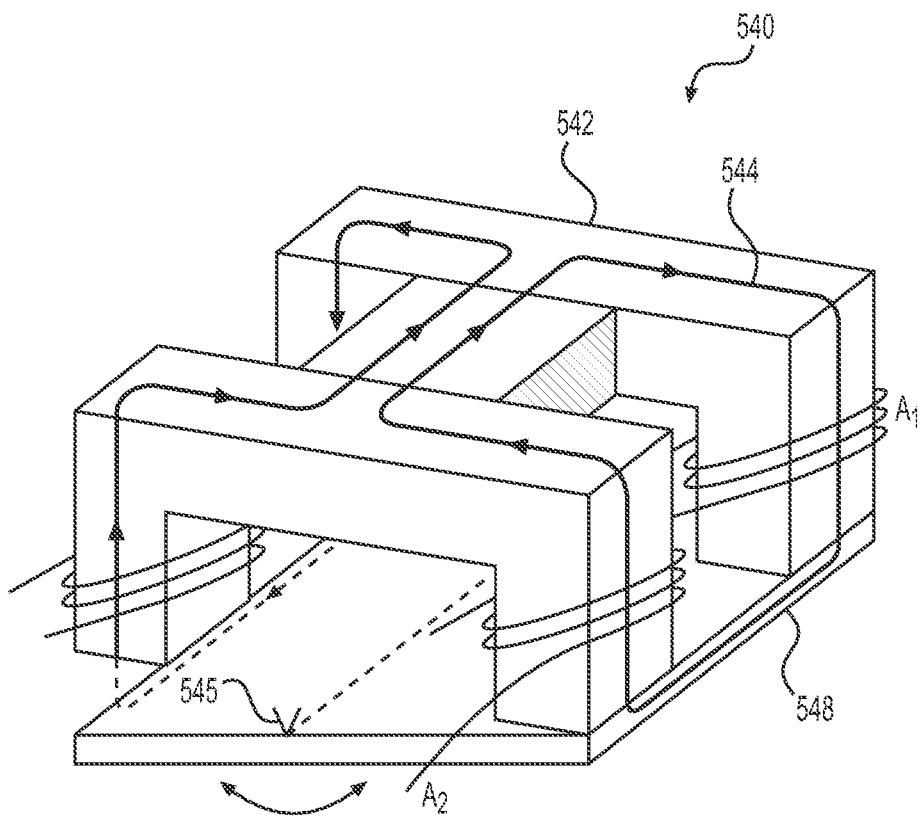
FIG. 14 is a diagram showing a different embodiment of an EM actuator. The actuator 540 includes a stator 542 with two sets of a pair of protruding legs and a quad-pole teeter-totter rotor 548. Poles $A_1$ and $A_2$, when energized, make most of the flux go through circuit 544, latching the rotor 548 rotating about the pivot point 545.

In FIG. 14, the actuator 540 includes a stator 542 with two sets of a pair of protruding legs and a quad-pole teeter-totter rotor 548. Poles $A_1$ and $A_2$, when energized, make most of the flux go through circuit 544, latching the rotor 548 rotating about the pivot point 545.

Examples of permanent magnets include any permanent magnet. These include alloys of rare-earth elements (lanthanide series, plus scandium and yttrium), as well as an alloy of neodymium, iron and boron. The permanent magnets may be uncoated. The permanent magnets may be plated or coated.

iii. Rotor or Mover

The rotor is typically an elongated body that rotates at its center, such as a pivot point, between at least two pole faces. The rotor typically contacts a notch flexure at its pivot point. In this configuration, the rotor may rotate about the notch flexure and switches by making contact with pole face on either leg of the stator.

The mover is typically an elongated body with at least two ends. The mover moves linearly along the horizontal axis when actuated. The mover typically contacts a flexure at a point on the mover. In some aspects, the mover contacts more than one flexure, each flexure positioned at intervals along the length of the mover. The mover may include one or more contact springs. Typically, the contact spring contacts the mover at the end of the mover. In some aspects, the contact spring may contact the mover at any location along the body of the mover. In some aspects, more than one contact spring contact the mover at both ends, along the length of the mover, or at both ends and along the length of the mover. The contact spring may include a pusher.

Generally, the rotor or mover incorporates features to locate the flexure, locate the contact spring as well as a pushing element for the contact spring. The rotor or mover typically has a thickness that prevents magnetic field saturation within the rotor or mover as a part of the magnetic circuit.

In an exemplary actuator, a thickness of 3 mm avoids magnetic field saturation within the rotor or the mover as a part of the magnetic circuit. When the rotor or the mover is latched to one of the legs (sides) of the stator, it creates an air gap between the other leg (side) of the stator and the rotor. The air gap may be any value, and is typically at least as deep as the chamber depth for deflecting the diaphragm to the full chamber depth. More preferably, the air gap is greater than the chamber depth and accommodates the deflection of the spring flexure, air gaps and manufacturing and assembly tolerances. Generally, the air gap is between about 2 and about 6 times the depth of the pump chamber, such as between about 3 and about 5 times, or at least about 2, about 2.5, about 3, about 3.5, about 4, about 4.5, about 5, about 5.5, or about 6 times the depth of the pump chamber.

In the example actuator, the air-gap is 0.4 mm on the other side when the rotor is latched to one of the sides. This is because the maximum required deflection of the diaphragm is 0.1 mm, i.e., the depth of the pump chambers. Having a deflection of 4 times that value accommodates the deflection of the spring flexure, air gaps and manufacturing and assembly tolerances.

The rotor or the mover may be formed of any magnetic material with relative permeability significantly greater than air. For example, the rotor or the mover may be formed of low carbon steel, medium carbon steel, or high carbon steel. The rotor may be formed of the same material used to form the stator.

iv. Winding

Typically, the connecting region of the stator, which connects the two legs, includes a coil wound around the region. The coil may be wound around the connecting region, around the legs, or both. The coil is the source of input magnetomotive force (MMF) into the actuator. Current through the winding creates a differential in the magnetic field between the pole faces at each side of the stator. This results in a net torque on the rotor causing it to flip. AWG30 insulated metal wires, such as copper wires, may be used for the winding.

However, other insulated or uninsulated wires may be used. Any gauge of winding wire capable of producing a sufficient number of Amp-turns to generate force sufficient to flip the rotor or move the mover may be used. Force to move the rotor or the mover can be scaled according to the requirement. The force is a function of air-gap, permanent magnet biasing, area at the pole faces, and the selected actuator topology. Any gauge of winding wire may be used to get a sufficient number of Amp-turns (as described in Example 7) to provide between 10 mA and 1000 mA, with a current density of up to 20 A/mm² in the winding. Exemplary wire gauge includes AWG between 0 and 40, such as between AWG5 and AWG40, between AWG8 and AWG40, between AWG10 and AWG40, or greater than AWG40. Exemplary wire gauge include AWG0, AWG1, AWG2, AWG3, AWG4, AWG5, AWG6, AWG7, AWG8, AWG9, AWG10, AWG11, AWG12, AWG13, AWG14, AWG15, AWG16, AWG17, AWG18, AWG19, AWG20, AWG21, AWG22, AWG23, AWG24, AWG25, AWG26, AWG27, AWG28, AWG29, AWG30, AWG31, AWG32, AWG33, AWG34, AWG35, AWG36, AWG37, AWG38, AWG39, and AWG40.

The number of turns used may be any number that provides the force sufficient to flip the rotor. For example, the number of turns may be between 100 and 50,000.

The number of turns in the presented embodiment varies from between 300 and 500. However, the number of turns may vary between 100 and 1000, between 150 and 900, between 200 and 800, between 250 and 700, and may be about 100, 150, 200, 250, 300, 350, 400, 450, 500, 550, 600, 650, 700, 750, 800, 850, 900, 950, or a 1000 turns.

v. Flexure

Flexures can be planar, non-planar, and may constrain in 5, 4, 3, 2, or 1 degree of freedom. Examples include blade flexures, notch flexures, wire flexures, torsion flexures, folded flexures, cross-flexures or bushings.

Figure 15:
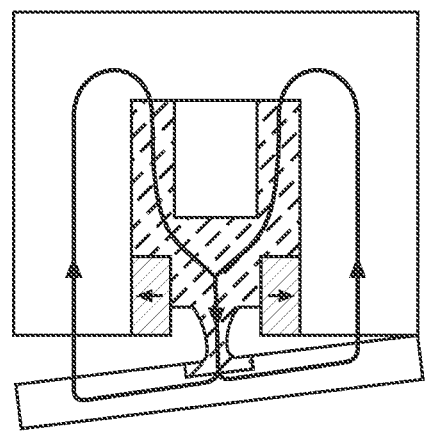
FIG. 15 is a diagram showing how the notch flexure allows for a shorter force loop. The forces travel internally and the whole loop is much stiffer compared to an external pivot.

The notch flexure typically provides mechanical support for the rotor and a pivot point around which the rotor rotates to make contact with a pole face of the stator. The notch flexure provides a relatively high-stiffness bearing in the vertical direction, and a short force-loop as shown in FIG. 15. Polycarbonates may be used as the polymer material as it has a high toughness and yield stress value and therefore can sustain a larger number of cycles of switching of the rotor. Metal notch flexures may also be used, but they are relatively more stiff and a large fraction of the actuation force would thus go into the deflection of the metal notch. Suitable materials for the notch flexure include any material with stiffness and strain range permitting rotor rotation. Suitable materials include materials with a Young's modulus less than that of aluminum, such as a Young's modulus between about 0.1 GPa and about 70 GPa, between about 0.1 GPa and about 50 GPa, between about 0.1 GPa and about 40 GPa, between about 0.1 GPa and about 20 GPa, or between about 0.1 GPa and about 10 GPa. These include metals, plastics, or composites.

Exemplary materials include polycarbonates, polystyrene, polyethylene, polyamide, polybenzoxazole, polymethylmethacrylate (PMMA), Polyimide aromatics, Polypropylene (PP), polyurethane, polyvinylchloride (PVC), and DELRIN® acetal (Polyoxymethylene POM, DuPont De Nemours and Company Corporation, Wilmington, Del.).

Figure 11A:
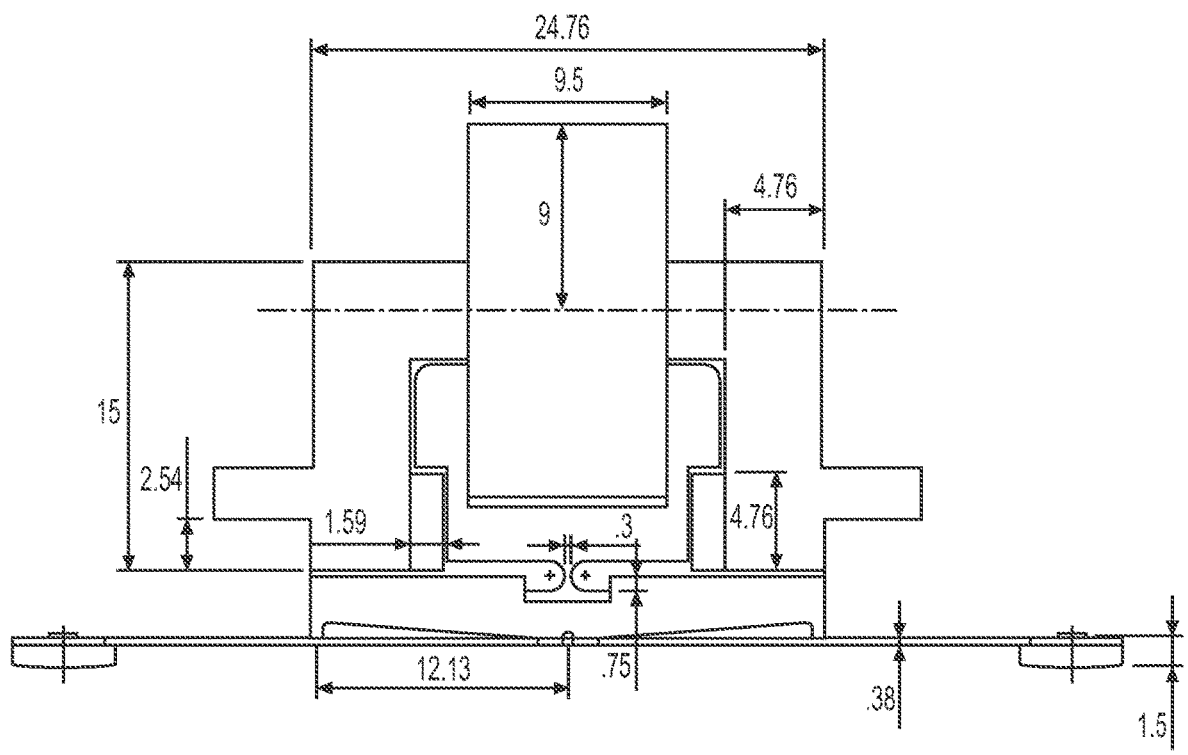
FIGS. 11A and 11B are diagrams showing detailed dimensions of the EM actuator elements presented in FIG. 10. All dimensions are in mm.
Figure 11B:
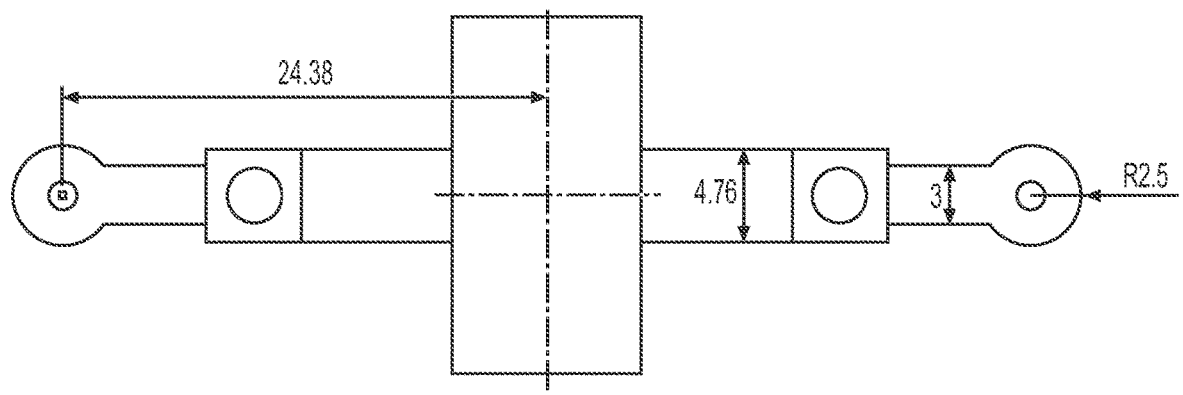

The notch may be designed such that the axis of rotation of the notch is fixed at the intersection of the plane parallel to the stator pole faces passing through the neutral position of the rotor and the vertical plane between the stator legs (FIGS. 11A and 11B). The notch flexure may include an air gap, such as the 0.2 mm air-gap, on each side.

vi. Contact Spring

A contact spring is an elongated or planar component operably linked with the rotor.

The contact spring ensures that independent of the diaphragm deflection, the rotor can always go into a latched state. It also helps bound the impact force with the diaphragm and fluidic platform, due to the relatively low inertia of the mass of the push buttons as compared to the rotor. After contact has been made, the force on the diaphragm is a result of the net deformation of the contact spring, as the rotor moves independently. The contact spring may also store energy from the actuation of the rotor, and may help reduce the acceleration of the rotor thereby reducing the impact force between the rotor and the stator pole face on the other side. This stored energy may then be used in the return stroke, providing a larger initial acceleration of the rotor compared to without the spring for the same Amp-turns of current through the winding. The magnetic force is weaker at a large air gap and the spring force assists in the initial acceleration of the rotor. At the contact location with the diaphragm, a conversion is needed from the deterministic and limited motion (0.4 mm) but undetermined and impulsive force (when rotor contacts stator pole face) of the rotor into undetermined and excessive motion (deflection of spring) and deterministic and limited force (limited maximum force) of the contact spring at the push-button—diaphragm interface.

The contact spring may be formed of the same materials as rotor and stator. The contact spring may be formed of any metal, plastic, or composite capable of providing the stiffness and the deflection ranges required to deflect the membranes. In order to have a long life (large number of switching cycles) of the springs, material with a high yield strength and fatigue resistance such as spring steel, may be used.

vii. Push Buttons

Stereolithography (SLA) 3D-printed push buttons may be attached to the contact spring and make contact with the diaphragm. These buttons may have a curved surface allowing the buttons to conform to the valve and pump chamber slopes. There may be some tolerance at the push-button—diaphragm contact interface to accommodate for geometrical and alignment errors. For valve sealing, the membrane may conformly deflect to the sealing lands. This is typically accomplished by using a layer of highly deformable elastomer such as sorbothane or natural rubber between the push button and the membrane. The elastomer acts to create a hydro-static stress state pushing onto the membrane and accommodates variations in depth in the deflection direction.

2. EM Micro-Pump Actuation a. Force Capability

The force capability of the EM actuator is typically enough to deflect a membrane by at least a stroke large enough to include the depth of the chamber, and deflect the membrane against a set back-pressure. In preferred embodiments, the force capability of the EM actuator is enough to deflect a membrane by at least a stroke large enough to include the depth of the chamber, the depth of any gaps and spring deflection, and deflect the membrane against a set back-pressure. For example, the EM actuator may have a force capability between about 0.5 N and about 5 N and a stroke between about 0.01 mm and about 5 mm to deflect the membrane by at least the depth of the chamber and against a set back-pressure.

The force capability of the EM pump actuators may be between about 0.5 N and about 5 N, between about 0.5 N and about 4 N, between about 0.5 N and about 3 N, between about 0.5 N and about 2 N, such as about 0.5 N, about 1 N, about 1.5 N, about 2 N, about 2.5 N, about 3 N, about 3.5 N, about 4 N, about 4.5 N, or about 5 N.

In some embodiments, the force capability of the EM actuators is 1N for a stroke of 0.4 mm.

b. Stroke Distance

Typical stroke values are at least about 0.01 mm, and vary between about 0.01 mm and 5 mm, such as between about 0.1 mm and about 5 mm, between about 0.1 mm and about 4 mm, between about 0.1 mm and about 3 mm, between about 0.1 mm and about 2 mm, between about 0.1 mm and about 1 mm, between about 0.1 mm and about 0.8 mm, such as about 0.1 mm, about 0.2 mm, about 0.3 mm, about 0.4 mm, about 0.5 mm, about 0.6 mm, about 0.7 mm, and about 0.8 mm. The values for back-pressure may vary, and may be between about 5 kPa and about 100 kPa, and may be between about 8 kPa and about 50 kPa, between about 10 kPa and about 40 kPa, between about 15 kPa and about 30 kPa, or about 20 kPa.

In exemplary pump and valve chambers with a geometry that requires the membrane to deflects by 0.1 mm, against a back-pressure of 20 kPa, the EM actuator typically has a force of about 1 N and stroke availability of about 0.4 mm to deflect the membrane till it touches the chamber walls.

3. EM Micro-Pump Blocks

EM micro-pump blocks may include any suitable number of EM micro-pumps, such as between one and 100, between one and 75, between 1 and 50, or between one and 25 EM micro-pumps, each of which includes one EM actuator. For example, the EM micro-pump block may include one, two, three, four, five, six, seven, eight, nine, ten, 11, 12, 13, 14, 15, 16, 17, 18, 19, 20, 21, 22, 23, 24, or 25 EM micro-pumps. Each EM micro-pump in the EM micro-pump block includes at least one EM actuator, and is typically coupled to an at least one valve chamber or to an at least one pump chamber. For example, an EM micro-pump block may include three EM actuators, EM actuator-1, EM actuator-2, and EM-actuator-3, where EM actuator-1 is coupled to between one and 12 valves preceding 12 pumps, EM actuator-2 is coupled to between one and 12 pumps, and EM-actuator-3 is coupled to between one and 12 valves succeeding the 12 pumps. In some embodiments providing only one point of contact of the push-button with the membrane, one pump, i.e. a sequence of valve-pump-valve, may need 3 EM actuators. In other embodiments, one EM actuator may be used to operate passive valves and/or pump in one EM micro-pump.

The EM micro-pumps typically have a minimal energy consumption, such that they may be operated by a set of standard batteries. A set includes one, two, three, four, five, six, seven, eight, nine, ten, 11, 12, 13, 14, 15, 16, 17, 18, 19, or 20 batteries. The batteries may be standard batteries capable of providing the actuation voltages.

During operation, the EM micro-pumps typically do not generate heat, and typically do not raise the fluid temperature more than by about 1° C. above the ambient temperature. For example, during operation at 37° C., the EM micro-pumps do not raise the fluid temperature above about 38° C. During operation at a 37° C. temperature, the fluid temperature typically remains below 38° C., and may be between about 37° C. and 37.9° C., between about 37.2° C. and 37.8° C., between about 37.4° C. and 37.6° C., or about 37.5° C.

The micro-pumps are generally compatible with and are able to operate in a standard tissue culture incubator for up to 4 weeks of non-stop operation for a given experiment. The diaphragm life and the life of the actuator elements determine the life of the micro-pump. For an actuation frequency of 4 Hz, running for 4 weeks, provides for 10 million ($1 \times 10^7$ strokes) strokes. The EM micro-pumps are suitable for repeat and numerous uses, and have a lifetime of years, the actuators typically operate successfully over about $1 \times 10^9$ strokes.

4. EM Micro-Pumps Provide Constant Stroke-Volume with Varying Back-Pressure

At the micro-scale, there has been lot of interest to develop electromagnetic pumps. The major categories of pumping systems using electromagnetic conversion of electricity into forces and motion are:

1. rotary micro-pumps with a rotating rotor which transfers momentum to the fluid;
2. diaphragm micro-pumps in which an electromagnetic actuator pushes a diaphragm, increasing the fluid pressure; and
3. electro- and magneto-kinetic pumps which continuously transfer energy to the fluid directly. These require special fluid or substrate properties for their operation (Au, et al., *Micromachines*, 2(4):179-220 (2011)).

Of these, at the micro-scale, only the diaphragm micro-pumps with active valves have been shown to have a deterministic flow-rate against a range of back-pressures. The available electromagnetically actuated diaphragm micro-pumps suffer from thermal problems due to the large electric currents (Nguyen, et al., *Journal of Fluids Engineering*, 124(2):384 (2002)). Tandon et al. describe an electromagnetic microdiaphragm pump with active valves (Tandon, et al., *Biomedical Microdevices*, 17(2) (2015); Tandon, et al., *Lab Chip*, 16(5):829-846 (2016)) although they do not report the energy consumption and show a varying stroke volume with back-pressure.

The EM micro-pumps typically operate with a low energy consumption, provide constant stroke volume with varying back-pressure, prevent substantial increase in actuator temperature during operation, and can be packaged into a portable pump block to be used with meso- and microfluidic plates of OOC platforms.

The EM actuator's low energy consumption is achieved by a latching design which requires only a short pulse of energy to switch its state and where springs store some of the actuator kinetic energy, which is then recovered in the reverse stroke. This results in a further reduction of the energy consumption of the actuator.

5. Exemplary EM Actuator and an EM Micro-Pump

Figure 10:
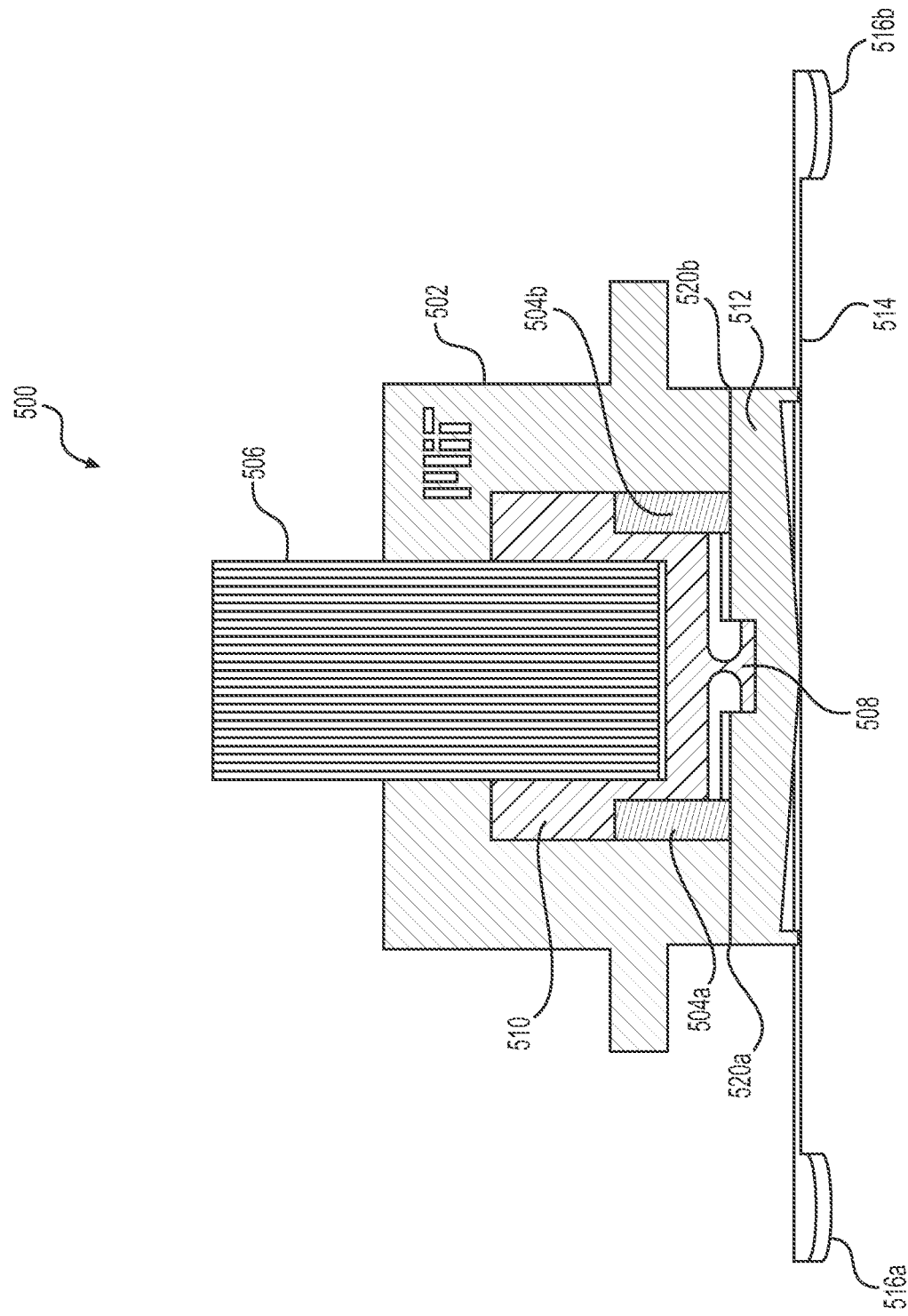
FIG. 10 is a diagram of an EM actuator module 500 showing the stator 502, permanent magnets 504a and 504b, winding 506, notch flexure 508, notch flexure frame 510, rotor 512, contact spring 514, and push buttons 516a and 516b. The teeter-totter rotor 512 rotates about the notch flexure 508 making contact with either side of the stator pole face 520a or 520b. The push-buttons 516a and 516b make contact with the membrane through an elastomer layer (not shown). The contact spring 514 help bound the force of contact of the push-buttons 516a and 516b with the membrane and store some of the actuator kinetic energy, which is recovered in the opposite stroke.

FIG. 10 shows an exemplary scaled-up version of an EM micro-pump with an EM actuator. The EM actuator includes a low-carbon steel stator, with neodymium permanent magnets attached on each side to provide the magnetic latching force for the rotor, which is also referred to as a teeter-totter. The rotor is made out of low-carbon steel. In operation, the rotor flips contact with the pole face on either side of the stator leg. It switches between the two stable equilibria, switching between left and right side contact like a playground teeter-totter. Current through copper winding of AWG-30 wire with between 300 and 500 turns is the actuation input signal. This current generates a magnetic field though the magnetic circuit creating a net differential of magnetic flux between the two ends of the rotor causing the rotor to flip.

Figure 12A:
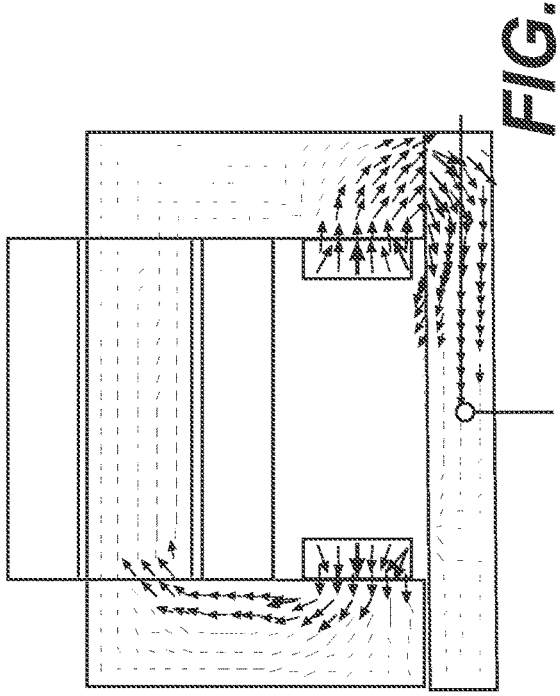
FIGS. 12A-12F are vector diagrams showing magnitude and direction of the B-field of the actuator module (stator, permanent magnets (PM), winding, and rotor only are shown).
Figure 12B:
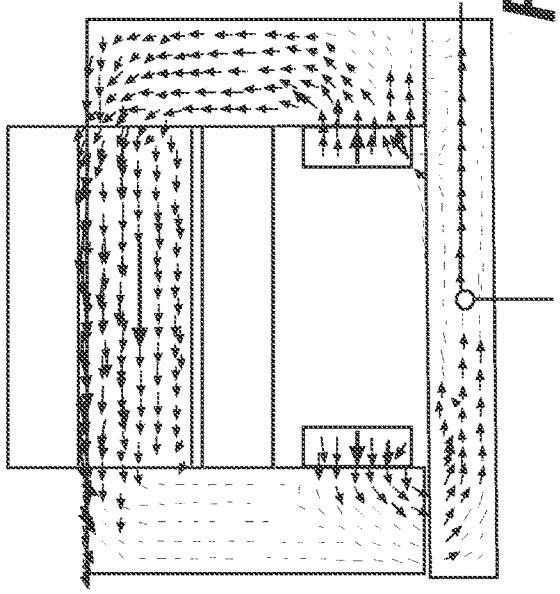
Figure 12C:
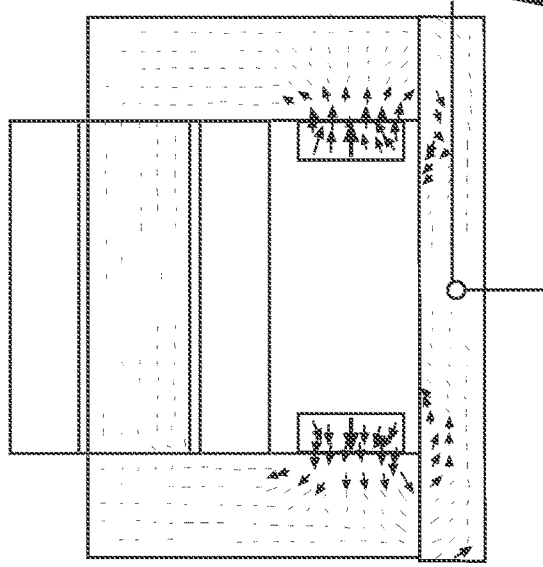
Figure 12D:
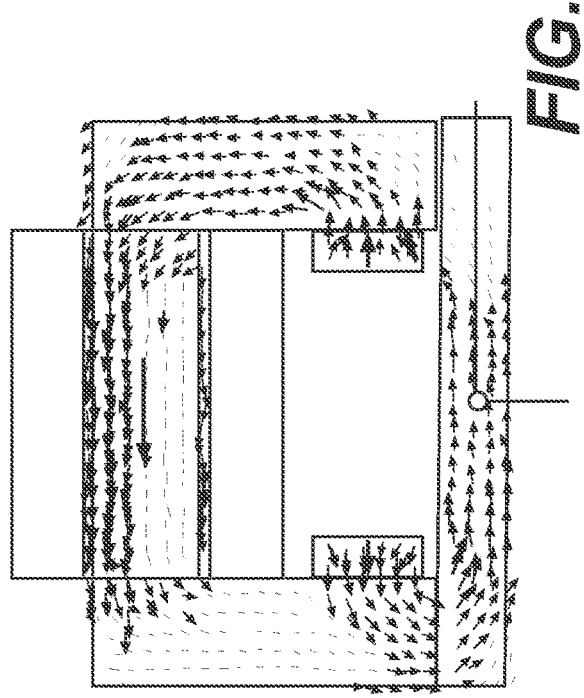
Figure 12E:
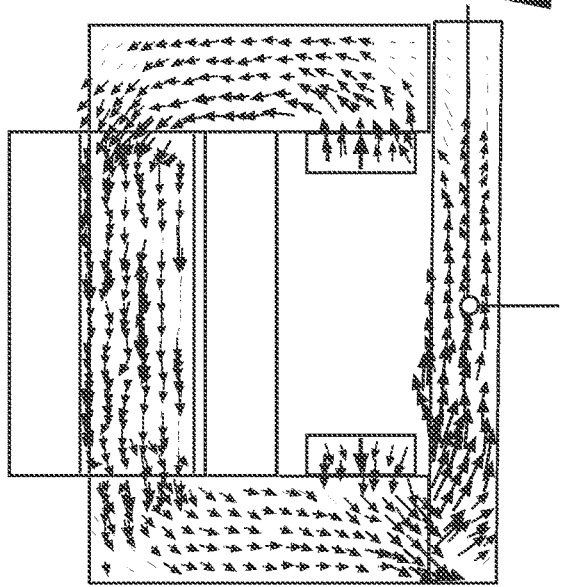
Figure 12F:
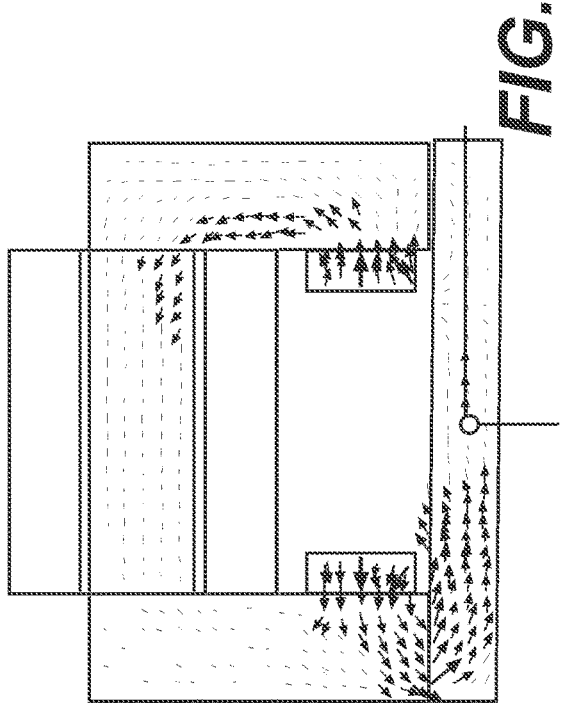

The magnetic fields of the actuator are shown in FIGS. 12A-12F. FIGS. 12A-12F are vector diagrams of the actuator module (stator, permanent magnets (PM), winding, and rotor only are shown) showing magnitude and direction of the B-field. FIGS. 12A and 12B represent the vector diagrams at right latch of the rotor. FIGS. 12C and 12D represent vector diagrams at neutral position of the rotor. FIGS. 12E and 12F represent vector diagrams at left latch of the rotor. The plots in FIGS. 12A, 12C and 12E represent no current through the winding and the plots in FIGS. 12B, 12D, and 12F represent 150 Amp-turns of current through the winding. When latched with no current (FIGS. 12A and 12E), the field from permanent magnet makes a short loop through the contacting pole face, thence into the rotor and then closes back to the permanent magnet by travelling through air. With 150 AT of current, the total B-field on the right stator pole face is reduced and the field on the left side of the stator increases to flip the rotor from the right to the left (left latch, FIGS. 12E and 12F). The bearing and pivot for rotation of the rotor is provided by a polycarbonate notch flexure. Polycarbonate is used due to its low modulus and high strain limits as compared with metal. A spring steel flexure with push-buttons makes contact with the diaphragm to deflect the diaphragm. Its low stiffness and mass help to bound the contact force with the diaphragm. The push-buttons have a geometry matching the pump and valve geometries and are stereolithography (SLA) 3D-printed.

The dimensions of the EM actuator elements are given in FIGS. 11A and 11B.

Materials and methods of making the separate elements for the EM pumps are presented in Table 10 below.

The exemplary scaled-up version of an EM micro-pump uses electrical energy, which can be supplied by a battery and is therefore portable. The EM pump uses a teeter-totter EM actuator having a low energy consumption of about 1 mJ/stroke. Running at 1 Hz pumping frequency that translates to a power consumption of 6 mW (total) for 3 actuators, one each in a set of valve-pump-valve. The steady-state actuator coil temperature rise is typically less than 0.1° C., confirming negligible heating in the winding due to this low power consumption. This makes the actuator suitable for use within a cell-culture incubator with very small effects on the nominal 37° C. temperature of the cell-culture medium, even for a platform using multiple actuators. The actuator's low energy consumption is achieved by a latching design which requires only a short pulse of energy to switch its state and where springs store some of the actuator kinetic energy, which is then recovered in the reverse stroke. FIGS. 12A-12F show the EM actuator in operation.

Figure 16:
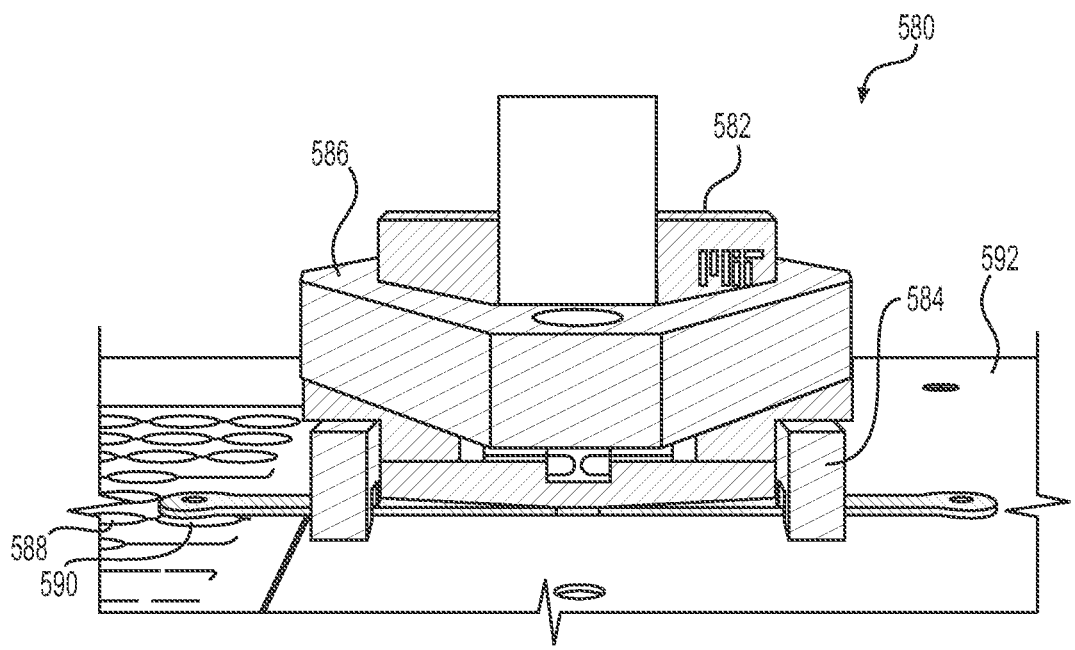
FIG. 16 is a diagram showing front view of an assembled EM actuator module integrated into an EM pump 580. The stator 582 is resting on aluminum standoffs 584 to adjust the height of the actuator and position the push-button 590 above the surface of membrane 588. An aluminum clamp 586 secures the actuator to the plate holder 592 using two bolts (not shown).

The EM actuators may be integrated with the injection-molded platforms. In one embodiment, the EM actuators integrated with an injection-molded platform, demonstrated pumping at a flowrate of 0.45 µL/stroke, temperature rise of less than 0.1° C., valve sealing up to 60 kPa, and a pumping frequency of 1 Hz, limited by diaphragm behavior. The assembly of the EM actuators into an EM pump is shown in FIG. 16.

III. Methods of Making the Pumps and Platforms

A. Methods of Making

The platforms may be fabricated through molding, machining, 3D-printing, milling, and sterilization processes. A monolithic surface micromachined fluidic plate is preferred. It provides reliable performance and it is easy to clean. All fluid contacting surfaces are accessible for cleaning. All components have relatively long lifetime, and no delamination occurs in sterilization processes such as autoclave. Pneumatics can be easily cleared of condensation. Generally, the platform uses only two plate components bonded together, such that all pneumatic channels occupy the same plane within the plate. Inlets may be stacked by interleaving their channels and using drilled features to connect the inlets at different vertical positions to the channel layer, thus packing them more densely on the side face of the manifold.

The turnaround cycle for modularized computer-aided design (CAD) and machining is relatively quick. It is easy and rapidly customizable according to user's individual needs. Computer numerical controlled (CNC) machines, such as lathes and mills, may be used to manufacture the components of the platforms.

B. Techniques for Assembly and Bonding

The fluidic plate, pneumatic plate, or EM actuator module, and membrane (if used) are generally assembled in a biosafety cabinet. Alternatively, fully assembled platforms may be provided ready to use.

A membrane diaphragm (optionally containing elastomer in regions corresponding to the pump and valve of the pneumatics) can be stretched between the pneumatics plate and the plate for the fluidic culture, and pressed to adhere to the pneumatic plate. In some embodiments, automation is used to attach the membrane to the fluidic plate.

Alternatively, elastomer patches may be used on the membrane layer to create seals and hermetic pathways in fluidic plates. Elastomer material may be used only at regions of a membrane or a patch corresponding to pneumatic pump and valves. Membranes containing elastomer patches can be prepared ahead of time and kept sterile for assembly of the chip. This would facilitate the assembly and operation of organ-on-chip plates where an elastomer is deflected to create a pumping action only in localized regions of the plate. A wide range of elastomer types and thicknesses may be applicable.

C. Sterilization

One or more sterilization procedures may be performed on the cell-culturing fluidic plate, the actuation membrane, and optionally the pneumatic plate. Sterilization techniques include gas treatment (e.g., ethylene oxide), ionizing radiation, sonication, surface treatment (e.g., surfactant), and autoclave.

Generally, the pneumatic plates do not require formal sterilization, but prior to assembly they may be wiped thoroughly with a wipe sprayed with 70% ethanol to remove any dust or particles from the sealing areas that contact the membrane.

Pneumatic actuator membranes may be rinsed in about 10% 7× solution and with excess deionized water. Generally, an ethylene oxide gas sterilization step follows after the membranes are air dried, and the membrane is allowed 24 hours to degas in a chemical fume hood.

IV. Methods of Using the System

In vitro to in vivo translation (IVIVT) is an interpretive step that compares and validates MPS results to clinically-relevant outcomes. The apparatus may be applied with the IVIVT method in assessing additional factors such as endogenous growth factor, inflammatory and hormone signals in the prediction of pharmacokinetics and pharmacodynamics (PK and PD). Compared with in vivo to in vitro correlation (IVIVC) and in vivo to in vitro extrapolation (IVIVE) methods in the prediction of PK, IVIVT goes a step further to include analysis of these additional factors and thus additionally predict PD, clinical toxicology, biomarkers, and patient stratification using information from MPS technologies. Combined with physiologically-based PK (PBPK) models for IVIVT, the platforms provide an improved quantitative forecast on human responses to test agents, taking into accounts missing organs, organ and media size mismatches, and drug exposure.

A. Preclinical Drug Discovery

The EM actuators and MPS platforms may be suitable for preclinical drug discovery. The platforms typically support survival and functional culture of one or more organs on the chip for an extended period of time such as days, two, three, four, five weeks, two months, three months, or longer. Long-term multi-organ cultures are particularly advantageous for studying the pharmacology of low-clearance drugs, supporting repeated drug exposures, analyzing drug-drug interactions, and modeling chronic diseases.

The platform can be used for target identification and validation, target-based screening, phenotypic screening, and other biotechnological applications.

Cell and media volumes provide enough signal for commercial assays such as ELISAs and high-content, multiplexed assays.

Multiple—omics measurements across the scales of information flow in cells, from DNA to RNA to protein, protein activity states, and metabolites, as well as similar types of analysis of patient-derived immune cell function.

Although standard culture systems are reasonably effective for most small molecule drug PK assays, a vast number of diseases lacking adequate therapies have inflammation implications and are not well represented or modeled in standard culture systems. The platforms may be particularly suitable for later stages of drug development that generally involves the immune system. The platforms may recapitulate a complex immunologically-based drug-drug interaction between the anti-IL6 receptor antibody, tocilizumab, and the metabolism of simvastatin—a phenomenon that could not be reproduced in standard cultures (Long T, et al., *Drug Metab Dispos* 44, 1940-1948 (2016)).

A wide range of drug agents (small molecules, peptide, proteins, nucleic acid, etc.) may be tested in the apparatus for medicinal, cosmetic, or scientific applications.

Agents are selected based on the disease or disorder to be treated or prevented.

B. Cells and Tissues

Differentiated cell types and specialized cell types such as stem cells and paneth cells, as well as microbiome for some embodiments such as gut MPS, may be added to the platform.

The microphysiological systems (MPSs) supported by the platform may comprise primary cells, cell lines, pluripotent stem cells, progenitor cells, organoids, or any combination of mammalian or non-mammalian cells seeded on the scaffolds.

Three-dimensional tissues comprising multiple cell types on a scaffold designed to distribute flow through the tissue may also be used. Cells and tissues with high oxygen demand include hepatocytes and liver tissues, muscle cells and tissues including cardiomyocytes and cardiac tissue, neuronal cells and tissues, and blood cells and tissues, such as lymphocytes.

C. Disease and Disorder to be Modeled

The organ-on-chip platforms are a useful tool for disease modeling and drug development, especially in identifying and defining the appropriate "minimal set" of interacting organ systems to represent a disease state.

Drug development for a variety of diseases and/or disorders may be improved utilizing the platforms by culturing relevant tissues or cell types for systemic studies. Complex individual organs-on-chips that capture the local features of disease, especially inflammation, are preferably applicable for modeling systemic diseases or diseases that are associated with multiple organs or involve multiple types of cells. The diseases and/or disorders that may be modeled in the bioreactor include, but are not limited to, cancers/tumors (e.g., tumors in the breast, bones, liver, lungs, and brain), chronic inflammatory diseases (e.g. diabetes, arthritis, endometriosis, and Alzheimer's), non-malignant growth of endometrium outside the uterus (endometriosis) or displaced into the uterine muscle (adenomyosis), abnormal liver functions such as those caused by non-alcoholic fatty liver disease, The system provides a means for exposing the cells to an agent to determine its effect on the cells administering the agent in different dosages, in a different dosing regimen, or in combination with one or more other agents and determining its effect on the cells, as well as wherein the agent is administered to different cell types or cell types associated with one or more diseases or disorders. This allows one to test agents in vitro with human cells under conditions mimicking a human, at least in part, under controlled conditions, looking for effects on other cell types, as well as on the cells one wants to monitor for an effect. This is more rapid, more controlled, and yet not restricted to a single class of cells or tissues.

V. Kits

Kits containing any one or a combination of pre-assembled platforms, sterile lids, pneumatic connectors, tubing, cell culture media, and additives to the cell culture media, are provided. Kits may also include disassembled platforms, membranes, EM pumps, hydraulic stage, and/or hydraulic plates, wherein the end user assembles the MPS well components provided in the kit. The components include MPS well scaffolds, filters, scaffold support, attachment means, membranes, fluidic plates, pneumatic plates, EM actuators, cell culture fluids, and instructions for assembly.

In some embodiments, the kits provide single-use platforms, which arrive sterile, in a sealed package. The end user may simply remove the platform from the package, plug in the connections and use the platforms. No prior sterilization or assembly steps may be required. The EM actuators, which may be moving mechanical pins, may be in mechanical contact with the membrane, which deflects into the fluidic side. Power is provided through power line, and signal may be acquired through signal port. The EM actuators typically switch the pneumatic channels between pressure and vacuum in pneumatic ports, which interface pump/valve chambers of the bottom plate, and deflect the membrane into the fluidic side. The EM actuators may be connected to pressure port, vacuum port, power line, and signal port. This pressure switching changes the pressure under the membrane and actuates the pump and valve chambers. This is the existing mode of operation in the tested platforms. The EM actuators may be physically close to or separated from the platform. In another aspect, the EM actuators may compress/expand an intermediate fluid to move cylinders and create pressure and vacuum. The fluid can be air or hydraulic fluid, which, via pneumatic or hydraulic ports interface with pump/valve chambers of the bottom plate, and deflect the membrane into the fluidic side. Power is provided through power line, and signal may be acquired through signal port. The EM actuators may be physically close to or separated from the platform.

The present invention will be further understood by reference to the following non-limiting examples.

EXAMPLES

Example 1. Diaphragm Polymer Materials and Chamber Geometries for Forming a Micro-Pump Generally, polymer manufacturing is a variable process in which it is challenging to achieve tight consistency in the composition at reasonable prices, especially for low volume manufacturing. In the existing pumps, polyurethane (PU) diaphragms were used, the physical properties of which were found to be varying stock to stock for the same specification, from the same manufacturer.

Therefore, based on the recommendation by the supplier, a larger lot quantity was purchased and was used to cut the diaphragms for the platforms to maintain assembly to assembly consistency.

It is important to limit the working range to within the linear elastic regime of the diaphragm material so that the diaphragm returns back to its initial position every actuation. Otherwise, if the material yields, it will have some permanent deformation set into the diaphragm which will cause it to slack leading to non-deterministic volumes. This means, the strain in the diaphragm should be limited to below the yield strain in normal operation.

For pneumatically actuated diaphragms, the ideal would be a diaphragm which requires almost zero force for deflection. This means that all the pressure at the input on the pneumatic side is seen by the fluid and the pressure required to maintain a certain deflection state on the membrane is negligible. All the applied pressure then, is used to oppose the fluidic back-pressure.

Figure 17A:
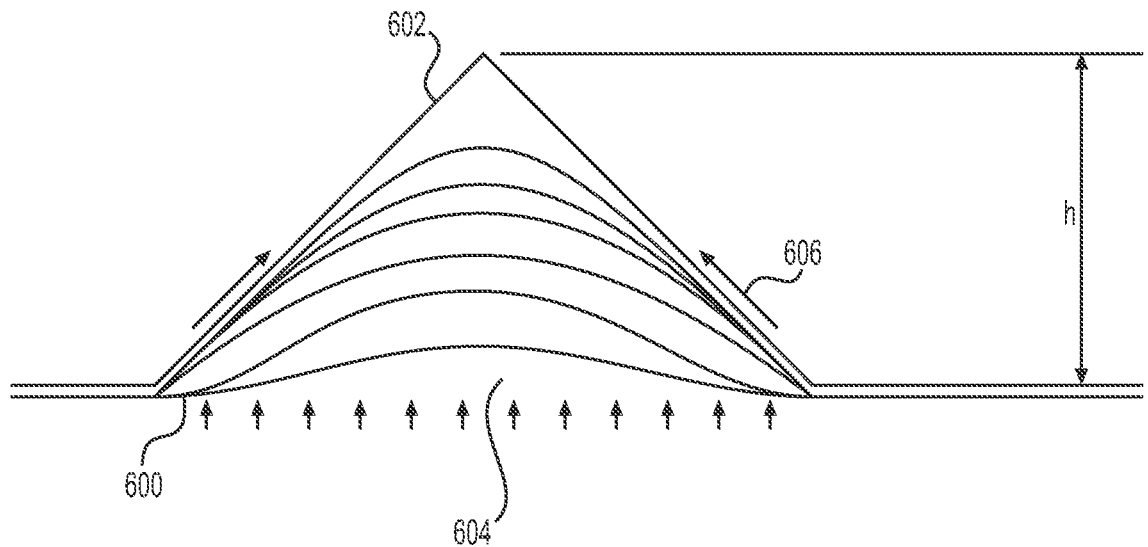
FIGS. 17A and 17B are diagrams showing propagation of diaphragm 600 deflection in a conical chamber 602. The contact with the wall linearly propagates upwards with increasing pressure 604. As that happens, the effective diameter of the diaphragm reduces and the diaphragm stiffness increases approximately quadratically. The membrane deflection follows contact propagation 606 (FIG. 17A).

For the disposable platforms described below, conical pump and valve chambers were used to have a well-defined propagation front of the diaphragm when it comes in contact with the chamber walls, as shown in FIG. 17A. To decide the diameter and depth of the pump and valve chambers, there are two modes of pneumatic actuation commonly used for diaphragm micro-pumps—(i) symmetric bidirectional actuation which uses both pressure and vacuum and (ii) unidirectional actuation which uses pressure only. The maximum operating pressure using symmetric bi-directional actuation mode is limited to around ±80 kPa(g), mostly limited by the line vacuum which cannot be lower than −15 psi(g) (−103.4 kPa(g)). Here "(g)" denotes that the pressure values are in gauge pressure, i.e. gauge pressure=absolute pressure−atmospheric pressure (absolute). An alternative would be to use only pressure to compress the fluidic chambers and use the stiffness of the diaphragm to retract and create the suction necessary to fill the pump chambers and open the valves. This would enable to use much larger pressures as the line pressures are generally higher, up to +300-400 kPa(g), which is a common mode of operation with very stiff diaphragms due to the larger pressure and hence larger force available for actuation.

The diaphragm stiffness varies non-linearly with deflection, having very low stiffness when the deflection is small and the stiffness increases at a faster rate (approximately as the square of the deflection, as the deflection varies as the cube root of pressure for large deflections) (Small, et al., *J. Mater. Res*, 7:1553 (1992)) as the deflections become larger. Therefore, to increase the stiffness at zero deflection, one solution is to have some initial tension in the diaphragm before bonding. The diaphragm would need to retain this tension stress in operation and not creep with time and with actuation stresses. Another solution would be to modify the membrane shape to have wavy undulations which make the membrane response more linear with pressure and increase the stiffness around zero deflection point. Although the manufacturing process becomes more complicated.

The symmetric bi-directional mode of actuation switches between pressure and vacuum. The pump chambers are of similar conical geometry on both sides of the diaphragm. For the valves, on the pneumatic side chambers are of a conical geometry with a pneumatic port connection of 0.5 mm diameter connecting to the pneumatic channels. On the fluidic side, 3 geometries are described—the doormat, mid-wall and rounded valves also. It is important to have a depth of at-least 1, 1.5, or 2 times larger than the thickness of the diaphragm to provide enough gap during bonding of the diaphragm. Otherwise, the diaphragm can touch the valve and pump chamber walls and get bonded to them which are called "bonding touchdowns". Based on the thickness of the diaphragm, a chamber depth of 0.075-0.150 mm was used. Another consideration is that there is typically a ±2% geometrical error in most micro-manufacturing processes for microfluidics (Becker, *Lab on a Chip*, 10(15):1894-1897 (2010)). Therefore, the deeper the pump chambers, the smaller the contribution of these random errors on the total stroke-volume variance. Deeper pump chamber also increases the pressure requirement for deflection and increases the strain in the diaphragm, which can cause yield.

Once the diaphragm comes in contact with the chamber walls, the diaphragm deflection behavior changes, and that needs to be taken into account. After contact, the diaphragm acts much stiffer and there is a smaller increase in deflection for large increases in pressure beyond that point, thereby saturating the displaced chamber volume beyond a certain pressure. The deflection of the diaphragm in the pump chamber should be limited at around 10-15 kPa(g) below the actuation pressure so that a constant stroke-volume up to 10-15 kPa of back-pressure capability, i.e. the pressure head against which the pump can pump at the same volume flowrate is maintained. For example, if the membrane touches the chamber wall at 20 kPa(g) and the actuation is at 40 kPa(g), then the additional 20 kPa is the back-pressure capability of the pump within which it will still pump out a deterministic stroke volume for a back-pressure between 0-20 kPa(g).

Example 2. Modeling and Testing the Deflection Behavior of Diaphragms

Materials and Methods

A model may be used to predict the diaphragm deflection for a given pressure difference across it, with a bonded (fully clamped) boundary condition at the edges. Then the pressure at which the diaphragm makes contact with the wall for the pumps and valves can be predicted. Diaphragm deflections can be categorized into three categories.

The thickness of the diaphragm is fixed (0.065-0.075 mm), the range of deflection depths (0.075-0.150 mm) is fixed and the range of pressures is also fixed (±20-±100 kPa(g)). Therefore, the problem is to find the feasible range of diameters which will work for these parameters. The diaphragm parameters used for modeling are given in Table 6.

TABLE 6

Diaphragm physical parameters used for modeling. Details of measurement of measured values are given in Example 3.

| Parameter | Symbol | Value | Units |
|---|---|---|---|
| Young's modulus (measured) | E | 1300-1500 | MPa |
| Density | P | 940 | kg/m$^3$ |
| Poisson's ratio | v | 0.41 | — |
| Yield strength (measured) | Y | 24 | MPa |

Modeling the Diaphragm Deflection
Assumptions and Considerations were as follows.
  The assumptions were:
  1. The diaphragm thickness is much smaller than the chamber diameter.
  2. The diaphragm is always within the linear proportionality limit of the material, i.e., below the yield stress, and
  3. The diaphragm material is isotropic.

For the diaphragm design, an analytical model helps to identify feasible designs. FEA may be used over these feasible designs to further refine the design.

Analytical expressions to predict the diaphragm deflection profile and the volume displaced in the pump chamber were developed and then verified using FEA and experiments.

For FEA, a non-linear FEA solver was used.

Boundary Conditions for the Diaphragm Deflection

The boundary conditions at the edge of the chambers are an important consideration to model the deflection of the diaphragm. In the available platforms, the polyurethane diaphragm is clamped between the fluidic and the pneumatic plates. This clamping by vertical compression generates horizontal compressive stresses at the edge of the diaphragm. For thin diaphragms with diameters an order of magnitude greater than the thickness, the buckling stiffness is very small and the diaphragm buckles (Small, et al., *J. Mater. Res*, 7:1553 (1992)). This makes the analysis of deflection of such diaphragms challenging as it is difficult to know the exact state of the diaphragm before actuation. In currently used designs, the membrane is pre-tensioned before clamping, to guarantee net tension after clamping. This was implemented by mounting the membrane on grip rings (Ultron Systems 10 UGR-12) to provide uniform tension.

The diaphragm was bonded and therefore, the compressive stresses were negligible. The initial stress state in the diaphragm was assumed to be constant with a value $\sigma_0$ (symmetric and equal in radial and tangential directions) with the corresponding in-plane strain of $\epsilon_0$ related by, $$\epsilon_0 = \frac{1-v}{E}\sigma_0 \qquad \text{Equation 2.1}$$

where, E is the Young's modulus and v is the Poisson's ratio for the diaphragm.

Approximate Solutions for the Deflection Shape

Figure 17B:
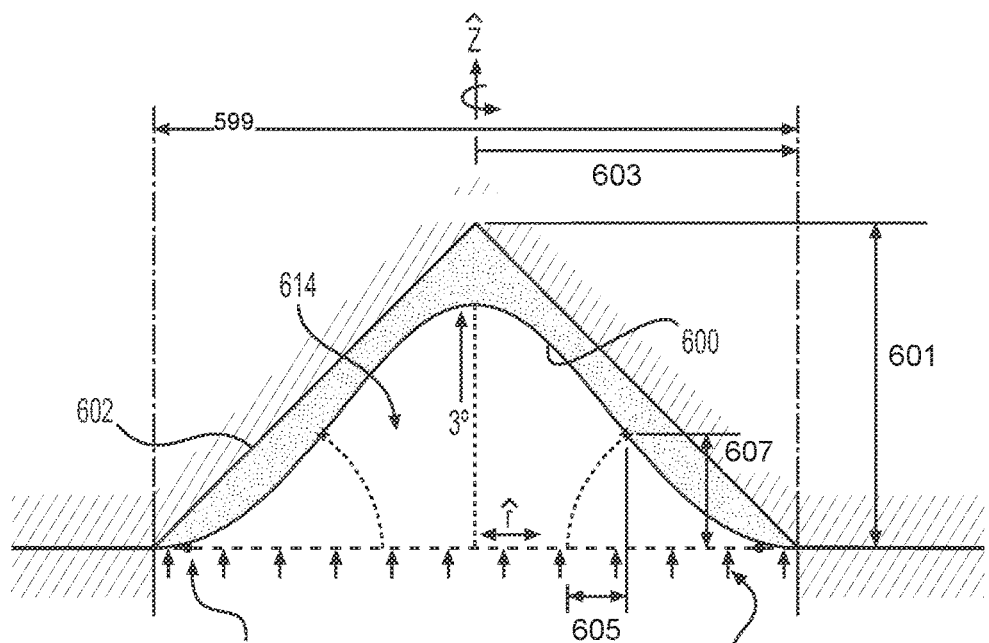

The diaphragm parameters used for modeling are listed in Table 7 and also shown in FIG. 17B. From the boundary conditions, the state of stress and strain in the diaphragm can be ascertained, which is also described in (Small, et al., *J. Mater. Res*, 7:1553 (1992)). At the boundary, due to the clamped condition, the tangential strain ($\epsilon\theta$) should be zero, and at the center, the tangential and the radial components of stress and strain should be equal due to axisymmetry.

The radial displacement (u(r)) and the vertical displacement (w(r)) vary with changing pressure and give rise to the deformed profile of the diaphragm and corresponding stresses. Due to the axisymmetric nature of the displacements, the radial and the vertical displacements uniquely define the displacement of any point on the diaphragm as a function of the radius, as shown in FIG. 17B. The boundary conditions are given below. Here, r is the radial coordinate and a is the radius, a=d/2, of the diaphragm.

TABLE 7

Parameters used for modeling the diaphragm deflection

| Parameter | Symbol | Units | Value |
|---|---|---|---|
| diaphragm diameter | d | mm | <to be found> |
| diaphragm radius | a | mm | d/2 |
| diaphragm thickness | t | mm | 0.065-0.075 |
| Height of chamber | h | mm | 0.075-0.150 |
| Actuation pressure | P | kPa | ±20-±80 |

$$u = 0 \qquad \frac{dw}{dr} = 0 \text{ at } r = 0 \qquad \text{Equation 2.2}$$

$$u = 0 \quad w = 0 \quad \frac{dw}{dr} = 0 \text{ at } r = a \qquad \text{Equation 2.3}$$

To get an exact solution using plate theory for these deflections which are of the order of diaphragm thickness, use numerical methods can be used (Timoshenko et al., 2nd ed. McGraw-Hill, New York, 1959). The difficulty comes from the complexity of solving the von-Kármán equations with the boundary conditions. To get an approximate solution for the deflection shape energy methods (Principal of virtual work) may be used. Timoshenko and Woinowsky-Krieger (Timoshenko et al., 2nd ed. McGraw-Hill, New York, 1959) assume the following deflection shapes for the radial, u and vertical, w displacements. They assume that the shape of the deflected surface for deflections of the order of the diaphragm thickness can be represented by the same equation as in the case of small plate deflections. Thus, for the vertical deflections, $$w = w_0\left(1 - \left(\frac{r}{a}\right)^2\right)^2 \qquad \text{Equation 2.4}$$

where w0 represents the maximum deflection at the center point of the diaphragm.

For the radial deflection, $$u = r(a-r)(C_1 + C_2 r + C_3 r^2 + \dots) \qquad \text{Equation 2.5}$$

Both these equations satisfy the radial and vertical boundary conditions. It is very difficult to take all the terms for the radial deflection into account and for the approximation, the first two terms in the series are taken. Therefore, u becomes, $$u = r(a-r)(C_1 + C_2 r) \qquad \text{Equation 2.6}$$

The unknown variables, w0, C1, C2 are constants which are found by minimizing the total strain energy, which is the sum of strain energy due to bending and tensile stretching, with respect to each of these variables. This gives 3 equations for three unknowns. Zhang (Zhang, *SCIENCE CHINA Physics, Mechanics & Astronomy China-Phys. Mech. Astron*, 59(59): 602-624 (2016)) solves the Timoshenko equations including the term for the initial stretching and expresses the equations in terms of the Poisson's ratio, v while Timoshenko use v as 0.25 or 0.3 for their derivation. Therefore, from Zhang, $$w_0 + \left\{\frac{3}{4}\left(\frac{a}{t}\right)^2(1+v)\epsilon_0\right\}w_0 + \qquad \text{Equation 2.7}$$

$$(0.4319 + 0.2411v - 0.188v^2)\frac{w_0^3}{t^2} = \frac{pa^4}{64D}$$

where D is the flexural rigidity of the diaphragm, given by, $$D = \frac{Eh^3}{12(1-v^2)} \qquad \text{Equation 2.8}$$

The first term in the left-hand side of Eq. 2.7 is due to bending, the second term is due to the initial stretching of the diaphragm and the third term is due to the further stretching from the tensile stress due to the pressure. Finding the real root to this equation, the value of w0 is obtained. The value of C1 and C2 can be found from the following equations, again from Zhang:

$$C_1 = [8.75(0.146 - 0.2603v) + 11.25(0.0127 + 0.13968\,v)]\frac{w_0^2}{a^3}$$

Equation 2.9 and, $$C_2 = [-11.25(0.146 - 0.2603v) - 18.75(0.0127 + 0.13968\,v)]\frac{w_0^2}{a^4}$$

Equation 2.10

All the terms required to evaluate u and w for the diaphragm are therefore obtained. The diaphragm stress and strain from this equation cannot be estimated, as they require second order derivatives of the displacements and from the assumed shape.

This analysis was used to find the diameters which satisfy the deflection requirements within the actuation pressure range and then FEA was use to verify that the stresses are within the yield limit. For long life of the diaphragms, it is recommended that the stresses be within ⅓ times the yield strength.

Results

Figure 18A:
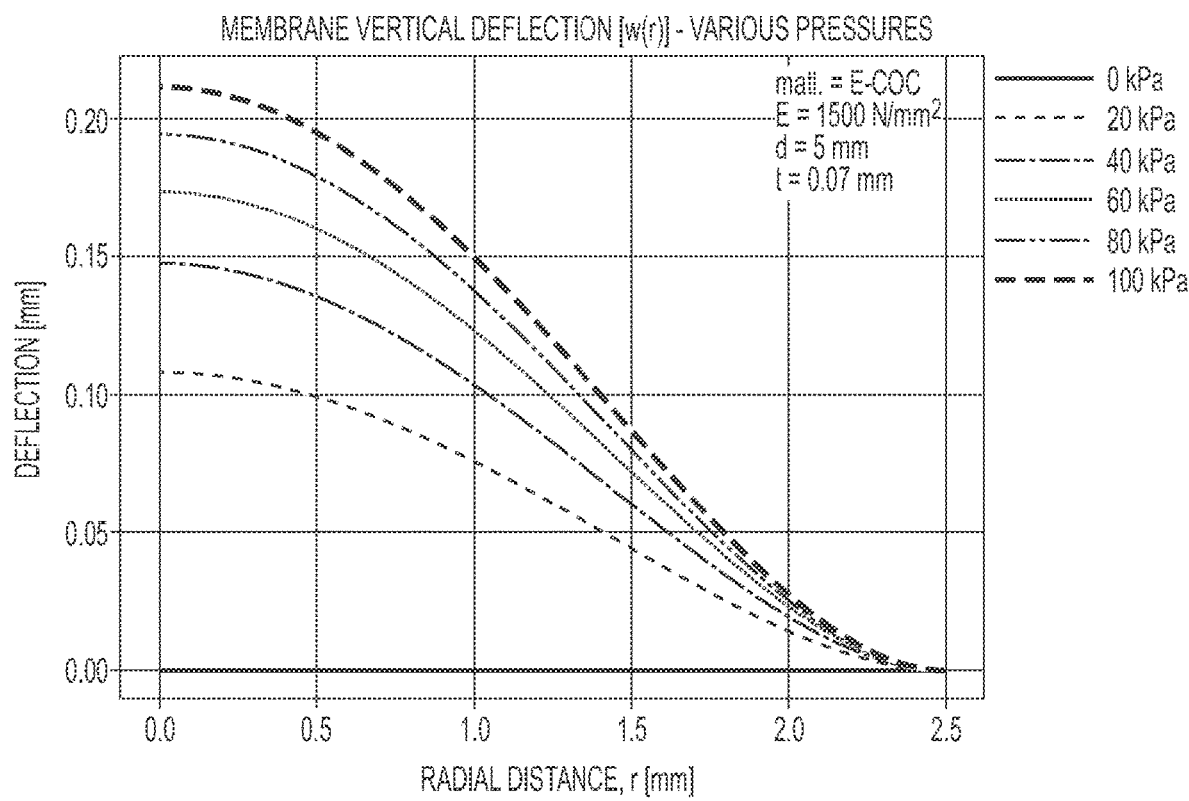
FIGS. 18A-18D are graphs and FIG. 18E is a diagram showing modeled and measured diaphragm deflection behavior.
Figure 18B:
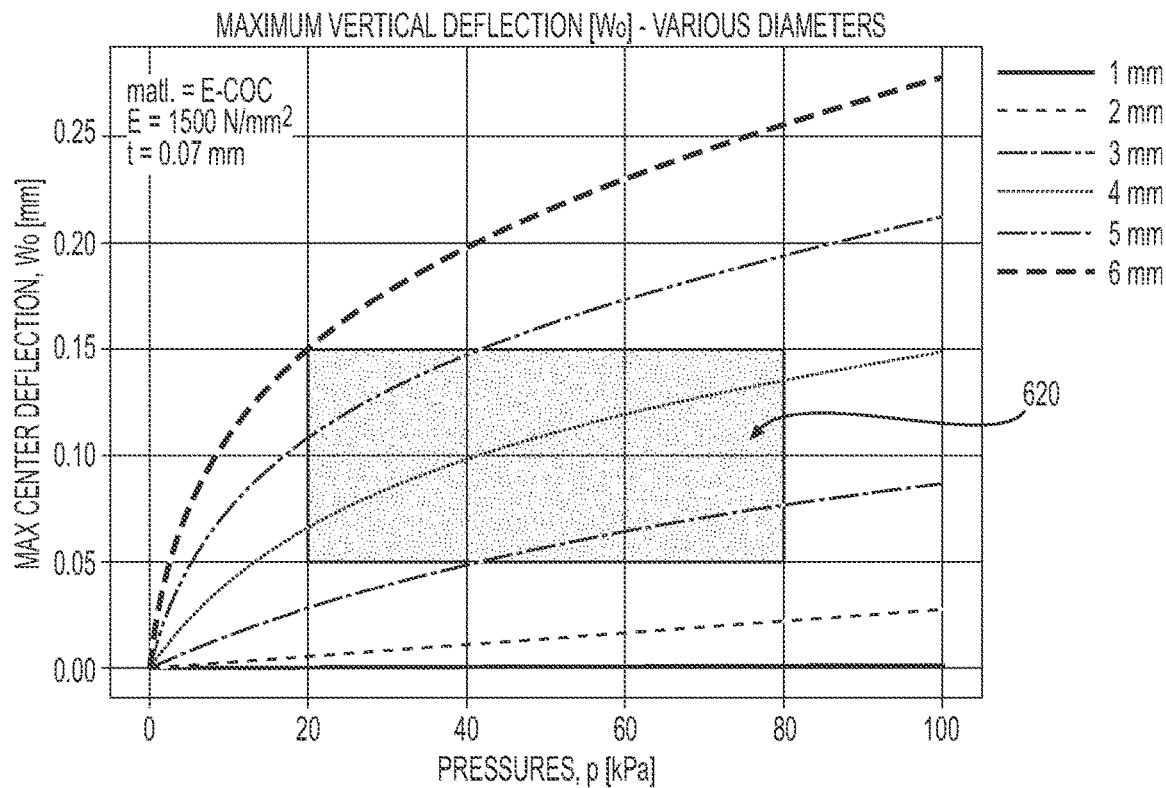

Using the analysis described above, the deflection profiles for the Timoshenko solution were calculated. The modeled vertical deflection (w(r)) profiles of the diaphragm for a diameter of 5 mm is shown in FIG. 18A. The deflection profile satisfied the boundary conditions of zero slope at the center and at the edge as well as zero deflection at the edge. FIG. 18B shows the variation of the mid-point vertical deflection vs. pressure for various diameters. From this, the range of chamber diameters can be obtained that would be feasible for the purpose based on the chamber height and actuation pressures. The diameters within 3-5 mm were feasible. The maximum deflection of the diaphragm showed a variation approximately as pressure to the power ⅓ for larger diameters (d≥4 mm) and linearly with pressure for smaller diameters (d≤2 mm).

Figure 18C:
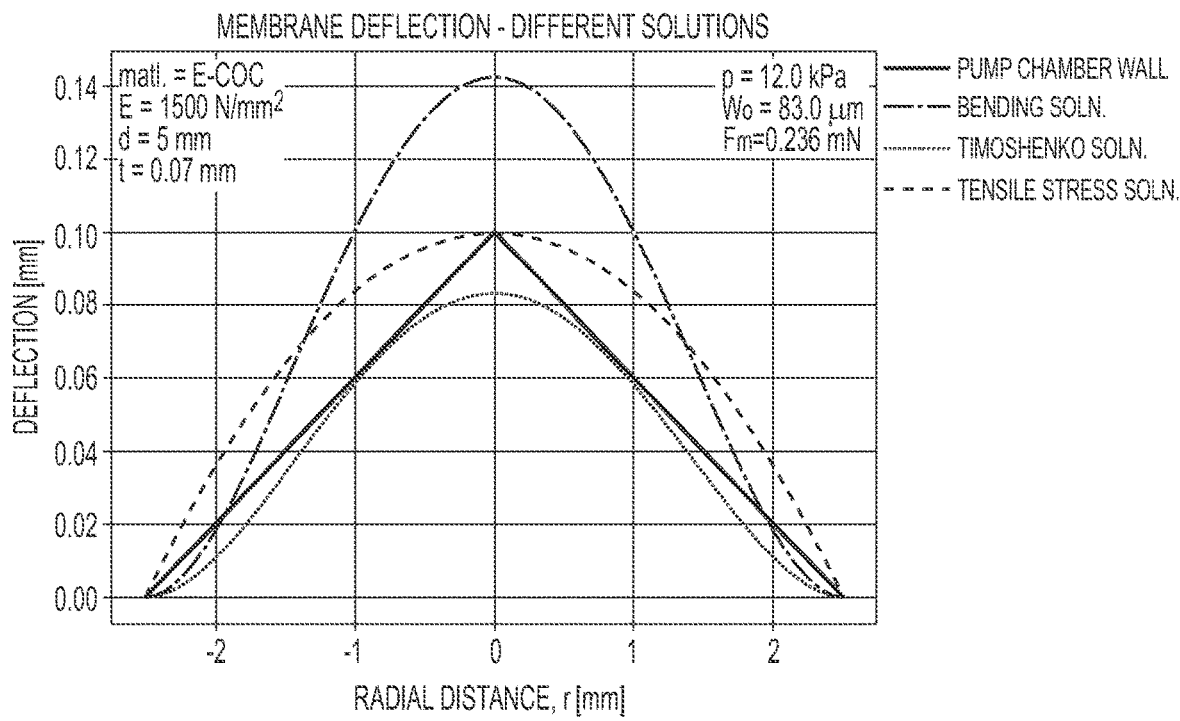

The chamber profile was also modeled and the pressure varied to see at what value the diaphragm make contact with the chamber walls, as shown in FIG. 18C. In addition, other solutions were modeled for comparison: (1) a bending solution which only considers the bending stresses and therefore overestimates the deflection, and (2) a tensile stress solution which only considers the tensile stresses and ignores bending and it also overestimates the deflection for small values of pressure. Timoshenko solution incorporates both the tensile and bending stresses and is thus most representative of the actual deflection over a wide range of deflections of the diaphragm. For a diaphragm diameter of 5 mm, it was predicted that the contact with the chamber walls occurs at a pressure of 12 kPa. Beyond this pressure, the diaphragm becomes much stiffer and there will be a much smaller change in deflection with increasing pressure.

The displacement profiles were verified by FEA. The displacement profile shows good agreement with the analytical data presented in FIG. 18A for 5 mm diameter, 40 kPa actuation. The maximum stress in the case of the 5 mm diaphragm diameter was 16.86 MPa, which was less than the yield stress of 24 kPa, reported in Table 6.

For a chamber depth of 0.1 mm, the diaphragm makes contact with the walls at 12 kPa, when the stresses would be smaller, including the edge. Beyond that, the net force due to increase in pressure is balanced by the reaction forces from the chamber walls. Therefore, the stress state should not increase much greater beyond that point. Therefore, the diaphragm was expected to have a long life over a large number of cycles in operation, which should be tested in the final injection molded platforms containing these pump features.

Figure 18D:
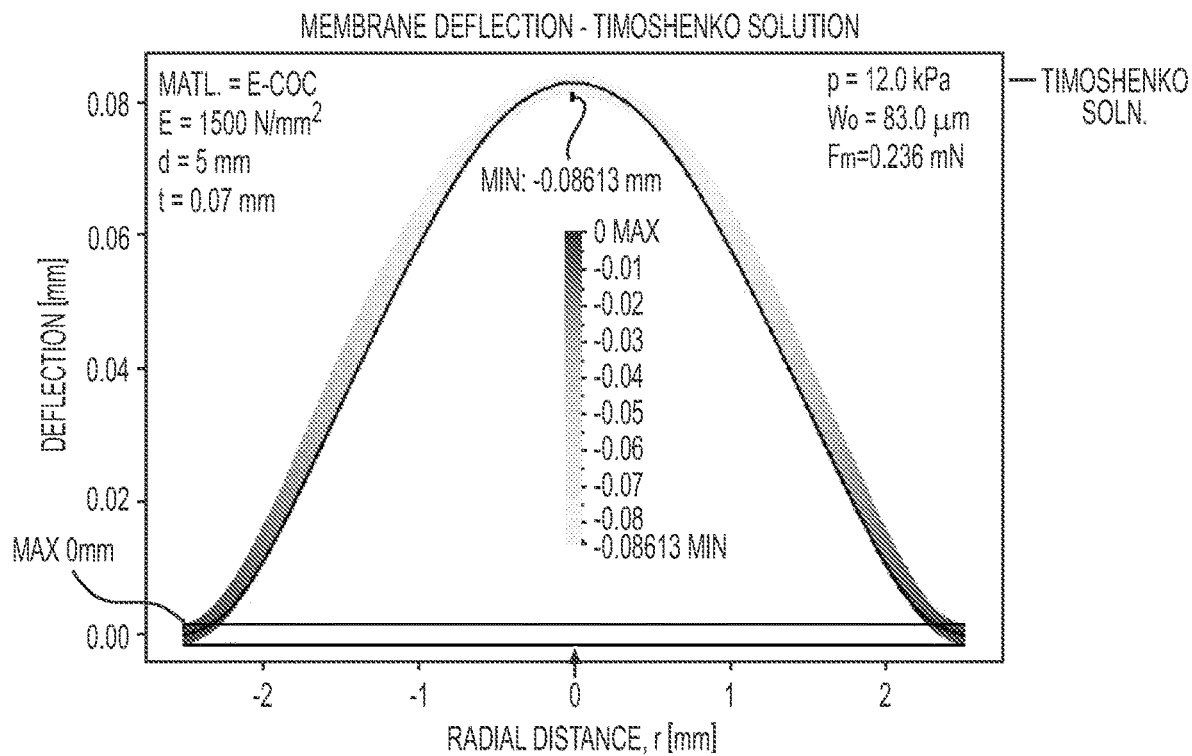

The model and FEA profiles for 5 mm diameter diaphragm with 12 kPa actuation as shown in FIG. 18D. The Timoshenko solutions matches quite well with the FEA results and the maximum stress in the diaphragm is found to be 7 MPa, which is less than ⅓ times the diaphragm yield stress.

Figure 18E:
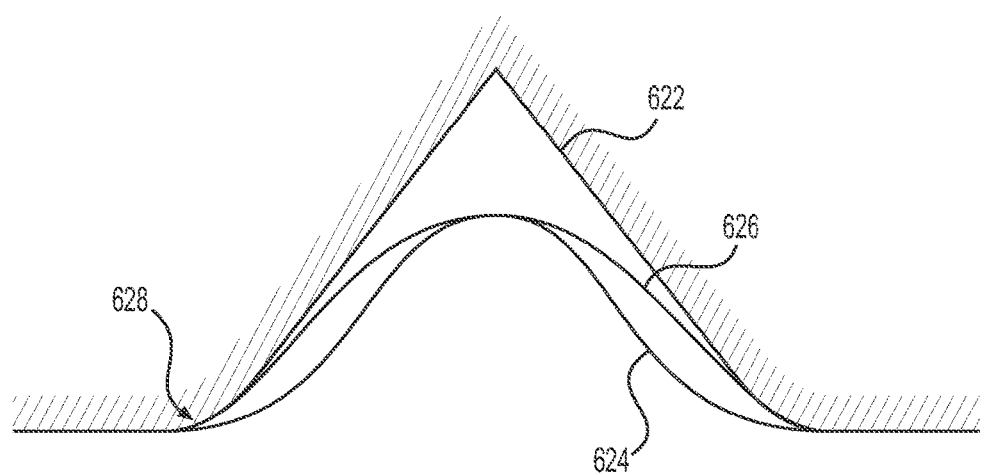

In the analysis, it was assumed that the diaphragm is free to deflect at the edges as long as it satisfies the zero vertical deflection and zero slope boundary condition. In practice, the manufactured pump chamber profile will have some radius at the base, which would modify the end boundary conditions as shown in FIG. 18E. There will be a higher stress concentration at the radius which will modify the slope at other end of the edge radius to a non-zero value. The maximum deflection would still be close to the Timoshenko solution as both bending and tensile stresses are significant. Therefore, the diaphragm deflection profile will be of an intermediate shape between the Timoshenko solution and the tensile stress solution shape with nearly the same maximum deflection as shown in FIG. 18E. Thus, the volume displaced by the diaphragm deflection when the diaphragm has not touched the chamber walls would lie between the volume given by under the Timoshenko displacement curve and under the tensile stress displacement curve with the same maximum deflection. In the manufacturing of the mold, the tip of the cone will also have a radius and that will also modify the actual volume displaced for large deflections of the diaphragm. The volume of a conical pump chamber of diameter d and depth h is given by the equation for volume of a cone, $$V_{cone} = \frac{\pi}{12}d^2 h.$$

Equation 2.11

The volume displaced under the Timoshenko profile is given by, $$V_{timoshenko} = \int_0^a 2\pi w_0 r\left(1 - \left(\frac{r}{a}\right)^2\right)^2 dr = \frac{\pi}{3}a^2 w_0.$$

Equation 2.12

The volume displaced by the diaphragm tensile stress solution, which is a spherical cap as given in, $$V_{tensile} = \frac{\pi}{6}w_0(3a^2 + w_0^2).$$

Equation 2.13

These give the bounds for the fluid volumes when the diaphragm is not in contact with the chamber walls. Vtimoshenko is the lower bound while Vtensile is the upper bound for the displaced volume.

Figure 19A:
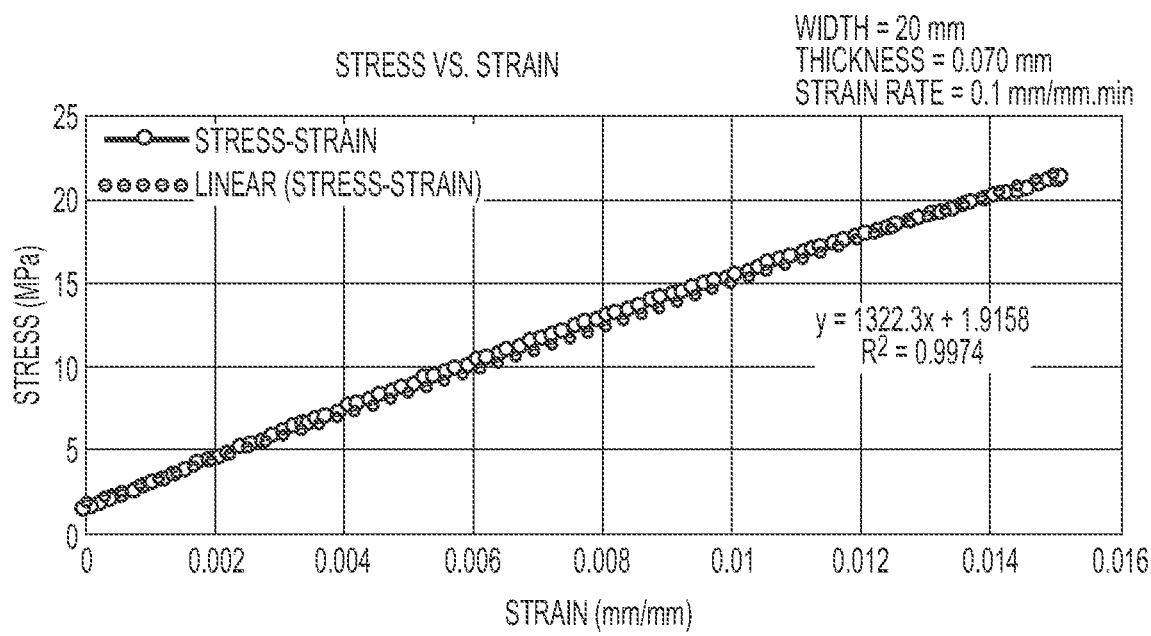
FIGS. 19A and 19B are graphs showing stress-strain curve obtained for the COC diaphragm with Young's modulus measurement.
Figure 19B:
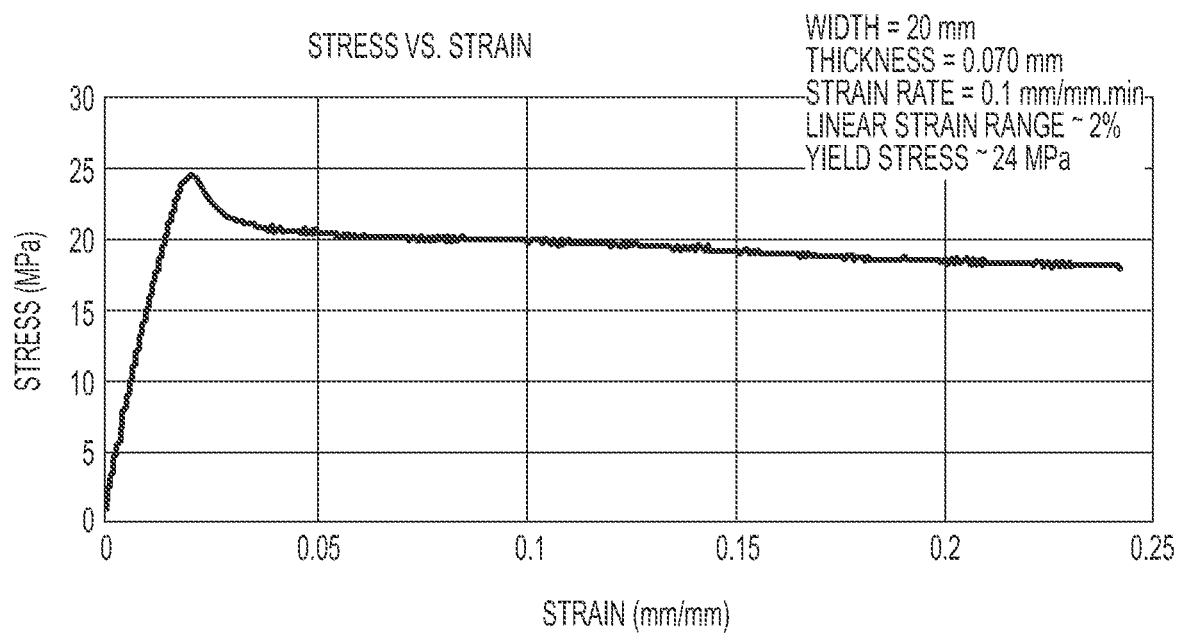

Example 3. Measurement of Uni-Axial Young's
Modulus of the COC Diaphragm and the Volume
Displaced Vs. Actuation Pressure Materials and Methods The physical parameters of the diaphragm were acquired. Since the physical properties such as Young's modulus and the yield stress can have a large variation manufacturing lot-to-lot, these properties were measured. The Young's modulus of the diaphragm was measured as per the ASTM D882-12 standard (ASTM International, "ASTM D882: Standard Test Method for Tensile Properties of Thin Plastic Sheeting," p. 12, 2012). The Young's modulus was measured for multiple trials and found to be in the range of 1300-1500 MPa. FIGS. 19A and 19B show the plots of data obtained for one of the tests. FIG. 19A shows calculation of Young's modulus with a linear fit line for the linear regime. The slope is the Young's modulus and the value is found to be 1322 MPa. In the regions of lower strain, the slope is slightly higher with a maximum value of 1500 MPa. Thus, the Young's modulus is 1300-1500 MPa. FIG. 19B shows stress-strain curve much beyond the yield stress. The yield stress is 24 MPa and the corresponding strain at yield is about 2%. The measurements were conducted on an INSTRON® 5960 series material tester (Instron Corporation, Canton, Mass.) as per ASTM D882-12 standard.

Figure 20A:
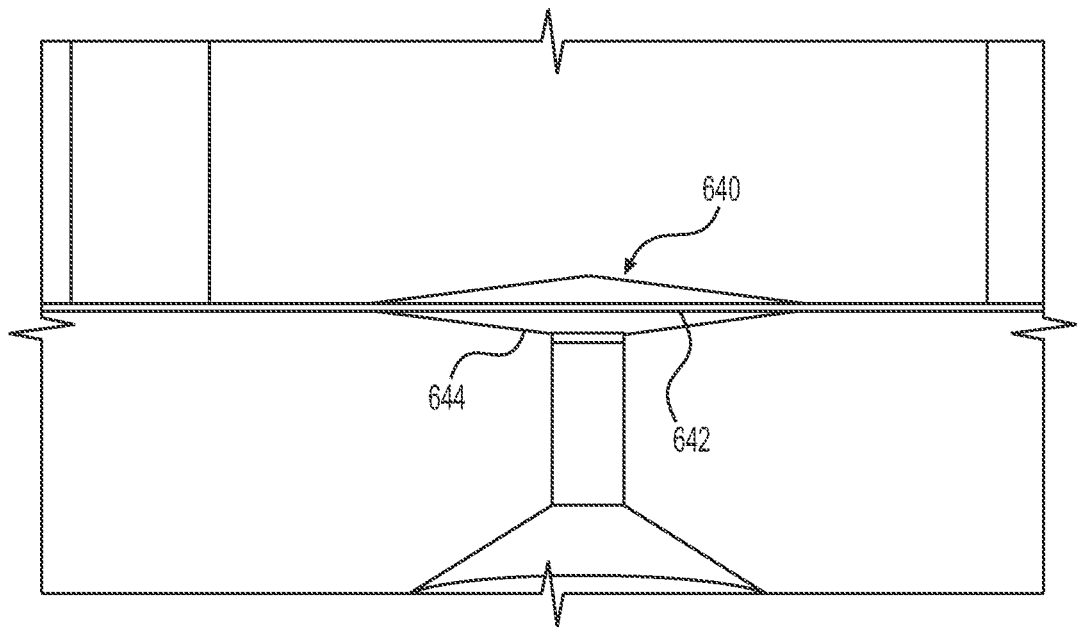
FIGS. 20A and 20B are diagrams showing manufactured pump chamber test block 630.
Figure 20B:
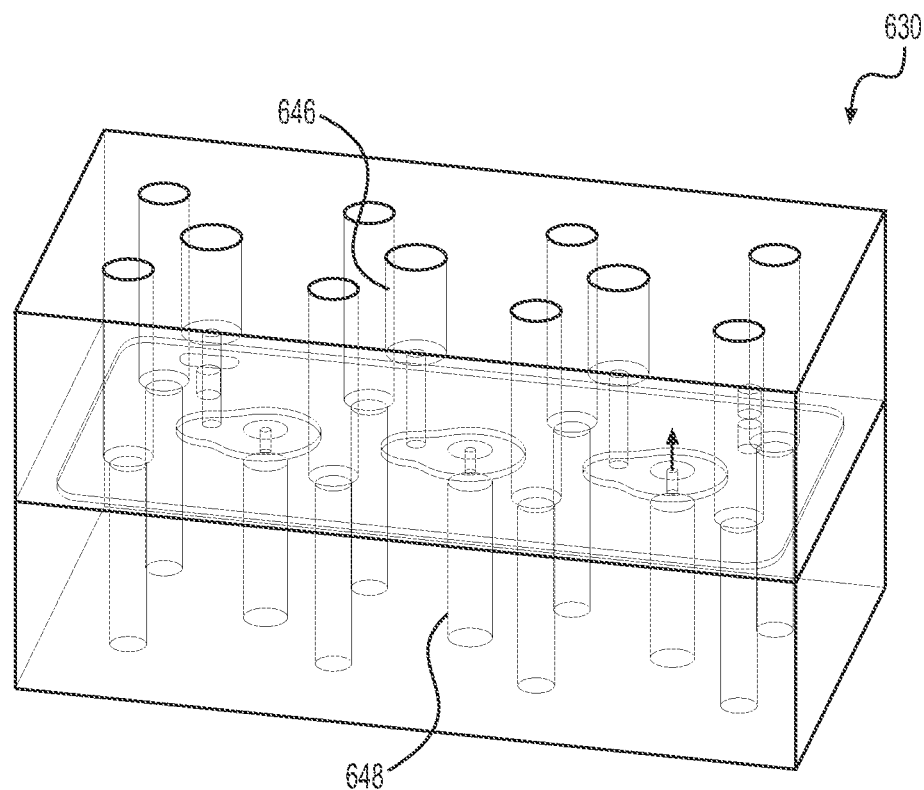

To verify the model and to roughly evaluate the pump chambers before finalizing the design for molding, an acrylic test block of the pump chamber was machined as shown in FIGS. 20A and 20B. FIGS. 20A and 20B are diagrams showing manufactured pump chamber test block 630 to evaluate the volume displaced vs. actuation pressure. Diagrams show the fluidic port 646, the upper fluidic chamber 640, COC diaphragm 642, lower pneumatic chamber 644, and pneumatic port 648. The diaphragm was pneumatically actuated from the port below and fluid was filled in the chamber above the diaphragm. The displaced fluid volume was measured from the displacement of the meniscus in a tube from a port connected to the upper chamber as shown in FIGS. 20A and 20B. The tested chamber diameters and chamber depths on the fluidic side are—(3 mm, 150 um), and (5 mm, 250 um) for pressures ranging from 20 kPa(g) to 80 kPa(g).

Figure 21A:
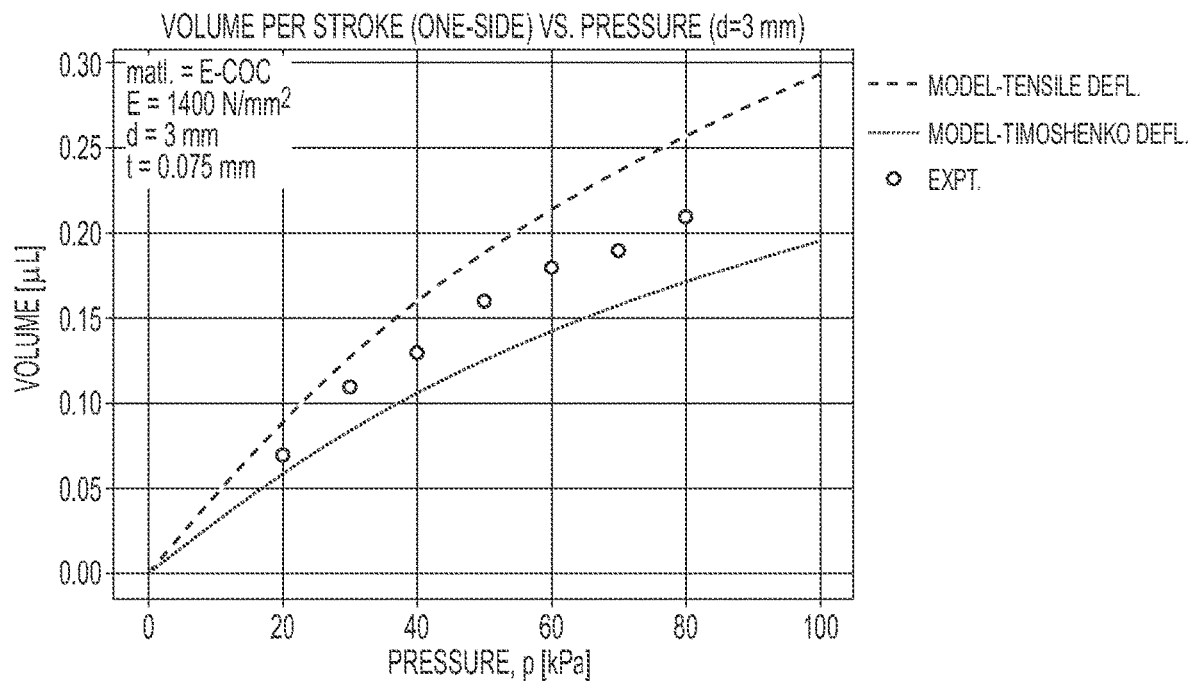
FIGS. 21A and 21B are graphs showing comparison of experimental data and model for the volume (μl) displaced per stroke vs. pressure, p (kPa).
Figure 21B:
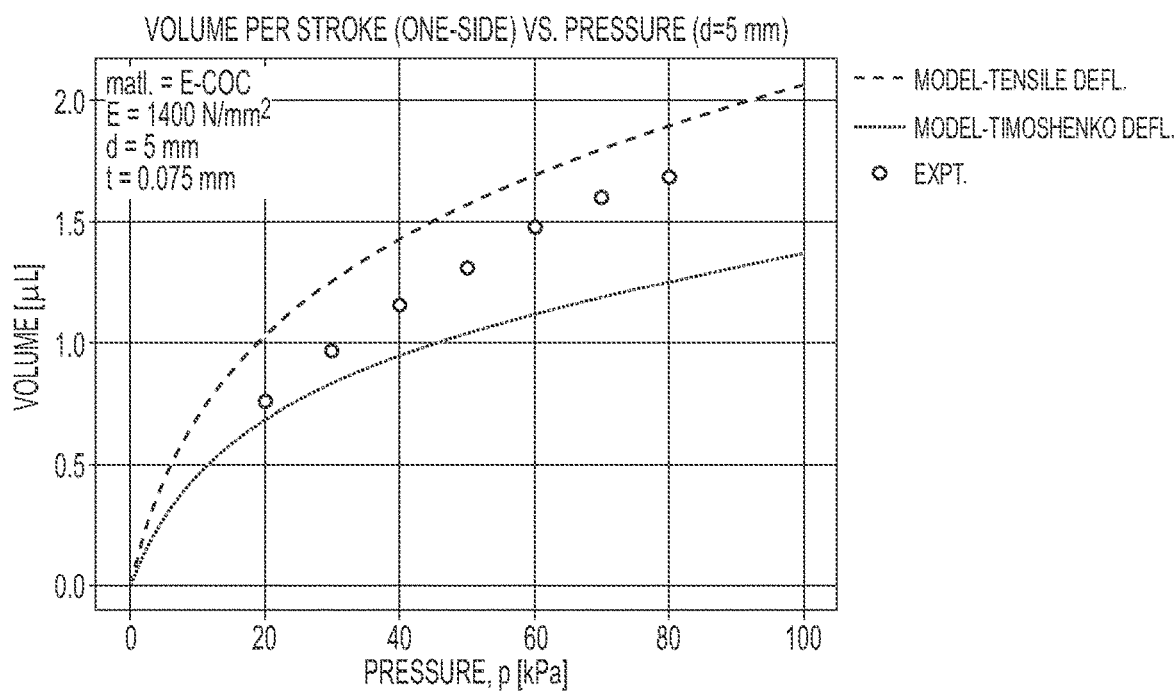

Modeling predicts that for the pressures actuated, the maximum deflection for the 3 mm diameter is 0.08 mm and for 5 mm diameter is 0.2 mm. Thus, the diaphragm should not touch the chamber walls. Hence, the volume upper and lower bounds as described in Example 2 can be used to compare the model with the experiments. FIGS. 21A and 21B show the stroke volume vs. pressure for the 3 mm and 5 mm diameter pump chambers. Considering the manufacturing tolerances (±20 μm) and the modeling uncertainties as described above, this shows that the model reasonably bounds the displaced volume.

Results

Based on the above analysis, and manufacturing considerations, 3 mm, 4 mm, and 5 mm chamber diameters were chosen with a chamber depth of 0.1 mm. The selected configuration is summarized in Table 8.

TABLE 8

Parameters of the pump chamber geometries selected for manufacturing.
Diaphragm material is COC, of thickness 0.065-0.075 mm.

| Dia. (mm) | Height (mm) | Stroke vol. (one-sided) μL | Stroke vol. (two-sided) μL | $P_{wall-contact}$ (kPa) | $F_{diaphragm}$ (mN) |
|---|---|---|---|---|---|
| 5 | 0.1 | 0.65 | 1.30 | 10 | 200 |
| 4 | 0.1 | 0.42 | 0.84 | 25 | 325 |
| 3 | 0.1 | 0.24 | 0.42 | 75 | 525 |

The details of the pumps and valves with these diameters, designed for manufacturing, are described above and Tables 1 and 2. In operation, as the pressure is increased, the diaphragm deflects and then makes contact with the chamber walls. Further increase in pressure only slightly increases the deflection and consequently, the displaced volume. Therefore, the volume displaced per stroke is almost constant beyond that pressure. The additional pressure gives rise to the back-pressure capability of the pump. A depth of 0.1 mm was chosen as it is almost 1.5 times the diaphragm thickness, within the linear deflection range of the diaphragm and feasible for bonding. Larger depths would require a larger actuation pressure for the diaphragm to make contact with the chamber walls while with shallower chambers the chances for bonding touchdowns increase.

Being able to predict the diaphragm deflection behavior helps with the design of pneumatic diaphragm micro-pumps. A model for the diaphragm deflection profile and displaced volumes was developed and the methodology of how to approach such problems was described. It was found that the Timoshenko deflection solution, which incorporates the contributions due to bending and the tensile stresses, approximates the deflection profile reasonably well. The model was verified using FEA and experiments measuring the displaced volume. The performance considerations of diaphragms for pumping were described. The model permitted to quickly ascertain the feasible geometry of the diaphragm and gave a bounding for the displaced volume per stroke. Though not discussed, it was found that the Timoshenko solutions also reasonably predicted large deflections for the 0.050 mm polyurethane membrane (Inman, et al., Journal of Micromechanics and Microengineering, 17(5):891-899 (2007)). Similar approach can be used to model a wide range of pneumatically actuated diaphragm deflection scenarios—from small to large deflections.

Example 4. Injection-Molded, Single-Use Pump
Test Block

Figure 22:
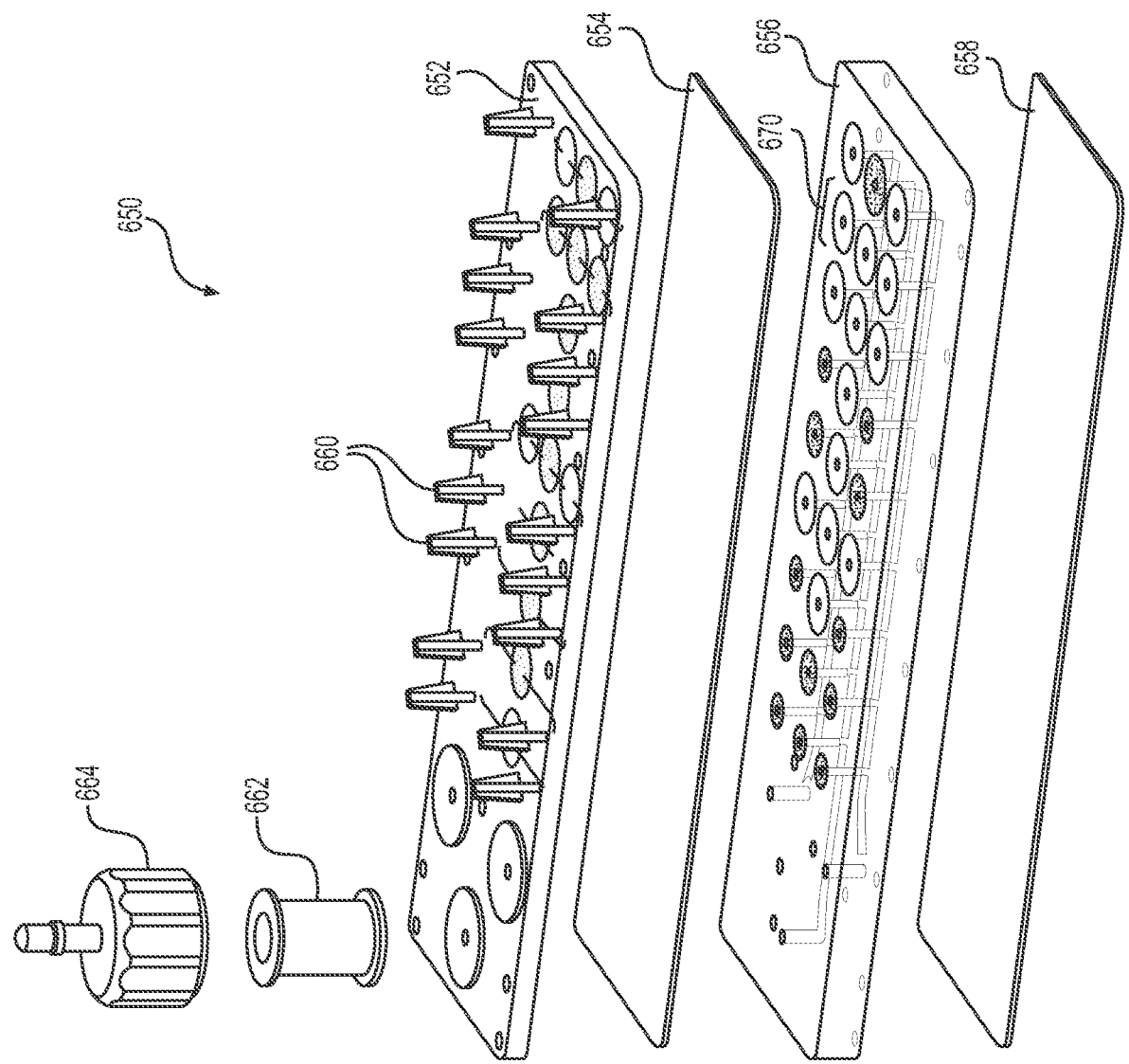
FIG. 22 is a diagram showing a perspective exploded view of the disposable injection molded pump test-block 650. The top (fluid) plate 652, membrane 654, bottom (pneumatic) plate 656 and the thick bottom cap 658 are made of Cyclic Olefin Copolymer (COC). There are 9 lanes of pneumatic diaphragm micro-pumps 670 (valve-pump-valve chambers) with different pump and valve geometries. This pump test-block is designed to demonstrate on-platform pumping and to evaluate feasible pump and valve geometries for integration with injection-molded MPS platforms. Shown are also olive connectors 660 for fluidic tubing, luer connector 662 bonded to the top plate 652, and connector 664 with luer lock and barbed end for pneumatic tubing.

A prototype pump test block was built to evaluate the feasibility of injection molded platforms with on-board pumps. The pump test block included 9 lanes of pump and valve variants (FIG. 22). Two versions were manufactured: (1) fully integrated platform with pneumatic actuation, and (2) just the membrane bonded to the fluidic top plate for actuation with the electromagnetic (EM) actuator.

Materials and Methods

On-platform pumping makes these platforms versatile, but also adds complexity in design and usage. The available platforms require careful assembly of the polyurethane membrane sandwiched between the fluidic top-plates and the pneumatic bottom plates. These platforms require significant effort in setup, which is especially challenging given the sterility requirements during and after assembly. Each pump degree of freedom requires 3 pneumatic connections (1 each for valve, pump and valve). The 7-way platform, which has 7 MPSs on-board, has 12 pump degrees-of-freedom and therefore 36 tubing connections. In addition, the top and bottom plates are clamped together with 72 screws. For wider adoption of these platforms, it is important to reduce the setup and assembly overhead, and also implement reliable sterility.

One solution is the use of injection-molded platforms in which the different layers including the membrane are bonded together, and which are used only once. Injection molding presents a one-time cost of making the mold, which is relatively expensive. After the upfront investment, the additional cost per part is small, provided there are larger numbers of parts used, so as to amortize the mold investment cost. This low cost per part makes these platforms amenable for one-time use. In a typical usage scenario, the single-use platforms arrives sterile, in a sealed package, and the user just needs to remove the platform from the package, plug in the connections and run the platforms. No prior sterilization or assembly steps, which consume significant time and effort, would be required. In addition, with bonded platforms, better bio-compatible materials may be used. For example, the available platforms use a polyurethane membrane as the diaphragm material. Polyurethane is an elastomer and absorbs small molecule, high log-D drugs and is therefore not an ideal material for drug studies with such classes of drugs. Commonly used thermoplastic materials for injection molding such as Cyclic Olefin Co-polymer (COC) are stable and do not significantly interact with such drugs. It is also optically transparent, which allows for easy imaging for biology experiments and for inspection. Therefore, COC was chosen as the material for the injection molded platforms described below.

Another benefit of a new design is to achieve improved repeatability of the pumping volume per stroke. The available pumps have a variance of about ±10% in the pumped volume per stroke. One of the major reasons for the variance in pumped volume per stroke is the manufacturing tolerances of the milling operations, which are on the order of 25-50 µm. This leads to variation in pump chamber geometry and hence to a variance in the stroke volumes, pump to pump on the same platform as well as between platforms. The dimensional tolerances of features in precision injection molding can be as low as 2-5 µm part to part. Therefore, with injection molding, the variation in volume per stroke can potentially be brought down to the order of ±2-5%.

Injection-Molded, Single-Use Platforms

There are significant differences in the design and manufacturing considerations of injection-molded vs. machined platforms. For injection-molded platforms, multiple injection-molded layers are bonded together as opposed to the assembled layers in the available platforms. The simplest system for diaphragm micro-pumps consists for 4 layers as shown in FIG. 22—a fluidic top-plate, a membrane (diaphragm for pumps and valves), a pneumatic bottom plate and a thick bottom cap plate to seal the pneumatic channels. In this configuration, the fluid and pneumatic plates can be molded with relatively simple mold geometries.

The COC membrane material has a Young's modulus of 1500 MPa, which is 2 orders of magnitude greater than the 4 MPa modulus of the polyurethane membrane. This much larger stiffness requires changes to the diaphragm diameter and deflection ranges to stay within a reasonable actuation pressure range below 100 kPa(g). The diaphragm deflections may be predicted using the model described in Example 2. Larger diaphragm diameters and shallower depths for the pump and valve geometries were required with the use of COC diaphragms.

For the first prototype, the designs were limited to a single layer each of fluidic and pneumatic plate. An additional fluidic layer, for example, would enable vertical fluid ports for the valves which would then have a more deterministic sealing contour. ChipShop GmbH was used to manufacture the platforms. ChipShop GmbH produced a fluidic devices with a footprint of the standard microscopy slide, i.e., 75×25 mm. The length of the fluid channels were adjusted to create a valve-pump-valve triplet within the footprint (FIG. 22).

For fluid connections, "olives", or olive connectors ("Microfluidic ChipShop Catalog" 2016), were used, which were molded in with the rest of the plates. They have a forward taper which is amenable to in-molding. For the pneumatic connectors, luer connectors were bonded onto the top-plates after molding (FIG. 22). A barbed luer-lock connector was attached onto the luer connector and connected to the pneumatic tubing for actuation.

Results

Figure 23:
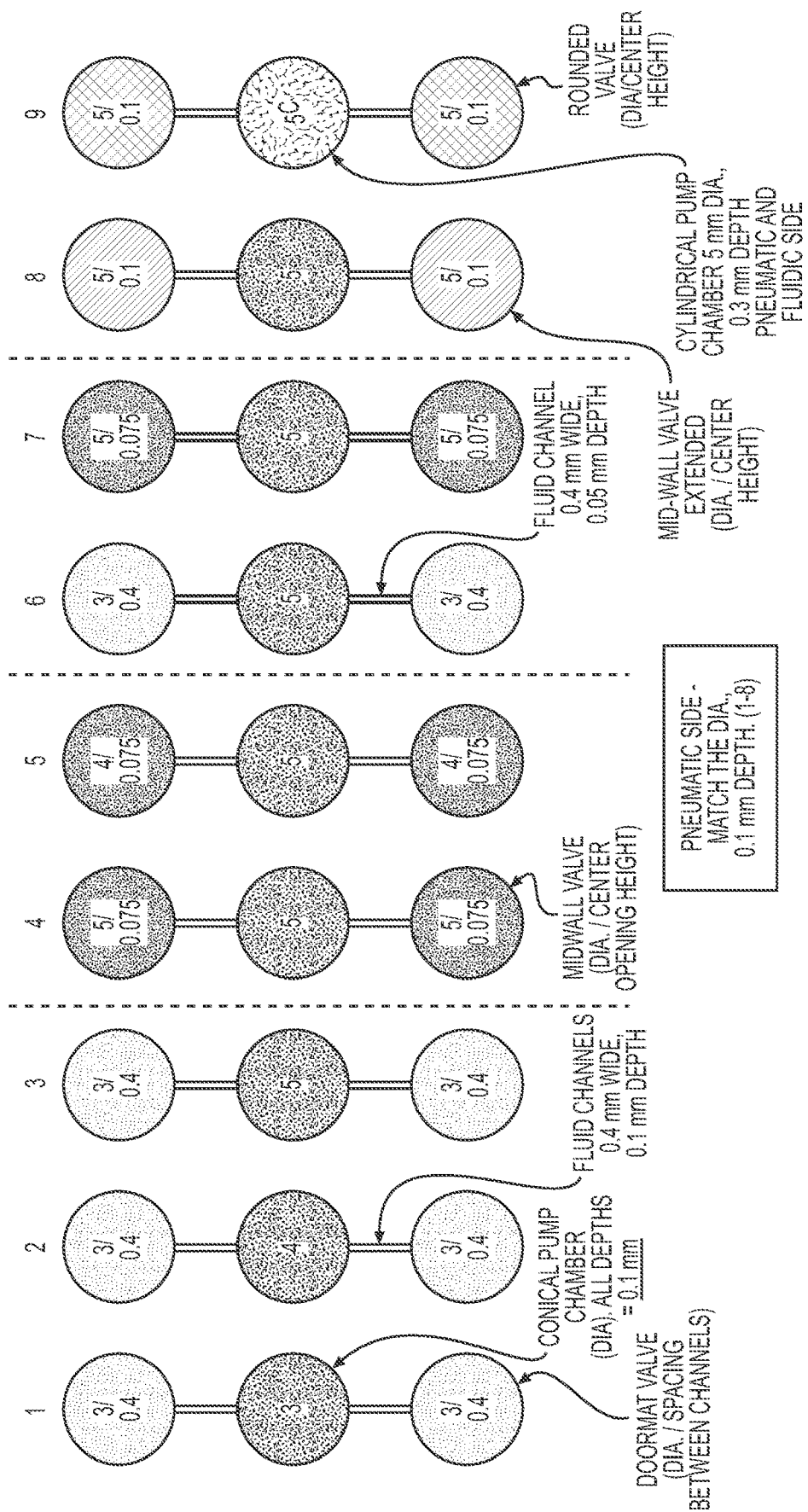
FIG. 23 is a diagram showing variants of pumps and valves geometries. Each pump lane consists of a sequence of valve-pump-valve.

FIG. 23 shows the variants tested for manufacturing feasibility and pumping performance. Lanes-1 to 3 test the doormat valves with 3 mm diameter and different pump chamber diameters. Lanes-4, 5 test the mid-wall valves. Lane 6 tests the same configuration as in Lane-3 but with shallower fluid channels connecting them. Lane-7 tests the same configuration as in Lane-4 with shallower fluid channels. Lane-8 tests a slightly modified mid-wall valve in which there is a region with zero slope at the edge of the circle to provide a better stress state to the deflecting diaphragm (Midwall-extended valve). Lane-9 tests a rounded valve geometry with a cylindrical pump chamber which would help visualize the deflection state of the membrane.

All pump chambers except in Lane-9 were conical with a depth of 0.1 mm and the variants designed to be tested for manufacturing feasibility and pumping performance.

All pump chambers, except in Lane-9 are conical with a depth of 0.1 mm and respective diameters. The shallower fluidic channels in Lane-6, 7 help evaluate if self-locking would be a concern even with stiff diaphragms.

A few samples of the pump test block were manufactured and demonstrated the presence of bonding touchdowns in the shallow pump and valve geometries. These either seal off the valve or pump completely or are bonded at a few points on the pump and valve chambers. Even if the membrane is only bonded at a few points, the diaphragm at the pump and valve chambers do not deflect when actuated with pressure and vacuum. Sealing of pneumatic channels around with the bottom cap was also present. For the pneumatic channels to seal well, the bond around the channels have to be sealed through their length, from the luer connectors to each of the valve and pump chambers.

A few plates were manufactured with the membrane bonded to the fluidic top plate to evaluate pumping and valve sealing with electromagnetic actuators (Example 6). Preliminary valve sealing and pumping tests have been successful.

Example 5. Design and Modeling of the EM Micro-Pump Elements

1. Electromagnetic Design and Modeling

The magnetic analysis is done using ANSYS Maxwell software package. Finite Element Analysis (FEA) was used to analyze this system with experiments to verify its validity.

3D FEA was chosen because the shallow dimensions of the actuator don't lend themselves well to be modelled in 2D where an infinite depth assumption would be made.

Details of the Material Specifications

1. Permanent magnet

For the FEA, an N35 grade of the magnet from the ANSYS library was used. The magnet is by K&J Magnetic Inc. with a magnetic coercivity of $8.9 \times 10^5$ A/m (11.2 kOe). The magnet used to build the prototype was of grade N42, which has a coercivity of greater than 11 kOe. The actual coercivity will have a range but be close to 11 kOe. The relative permeability used is 1.00998.

2. Stator and Rotor

Steel 1010 from the material library was used for FEA with the default nonlinear properties. The material used for the prototype is low carbon steel from McMaster Can. The actual material properties are close to the values used for FEA.

Due to coating of the magnet and the adhesive bonding and alignment of the magnet to the stator in assembly, there will be an offset in position which is shown as $y_{off}$ and $x_{off}$. This is the setup of the model used for further analysis.

At the neutral position, i.e., at the position where the air-gap is equal to 0.2 mm on both poles of the stator, the magnetic flux from the permanent magnets is symmetric on both sides and there is no net torque. As the rotor tilts and moves closer to one pole, the magnetic flux through that side increases and correspondingly decreases through the other side, resulting in a net torque about the z-axis in the direction of the closer pole face as shown in FIGS. 24A and 24B. The net torque increases as the rotor gets close to the pole face until it finally makes contact. This process depends upon the fluxes from both the PM and the coil The maximum air gap on the side not in contact with a stator pole face is then 0.4 mm and the rotor has tilted by an angle of about 1°.

Modeling of latching forces (rotor touching stator pole face on one side) in the state with no current in the winding as well as the force on the rotor as the Amp-turns are increased when flipping the rotor was as follows.

0 Current Through the Winding

Figure 25B:
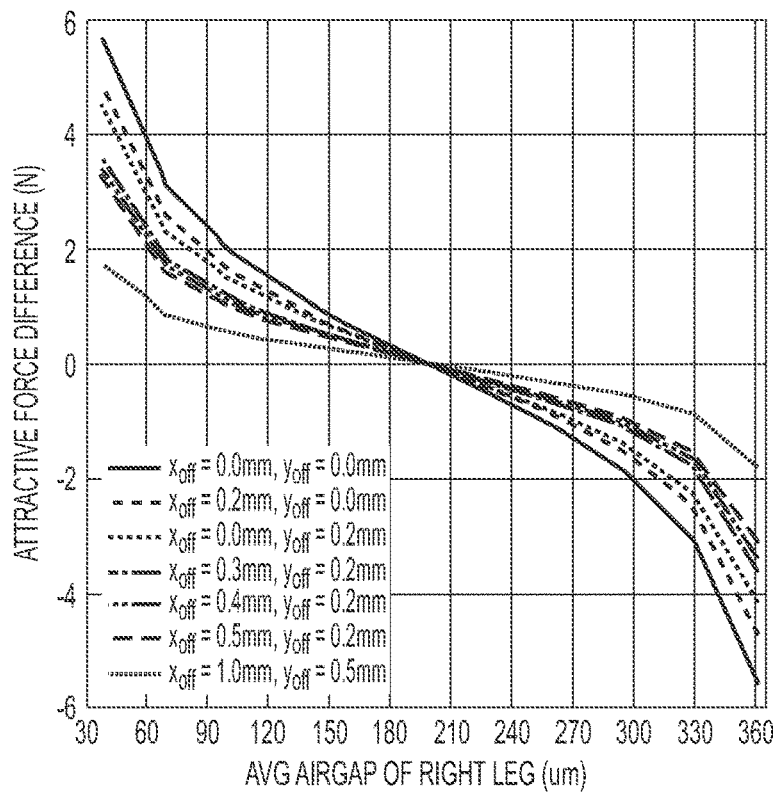

FIGS. 25A and 25B show a plot of net torque vs. rotor angle for 0 current through the winding and thus depending only on the permanent magnets. FIG. 25A shows the difference of the forces on each side vs. the air-gap at the right pole face of the stator-rotor combination. A change in the forces and torques due to the $x_{off}$ and $y_{off}$ values was seen. This was due to high intensity of B-field close to the permanent magnets which result in large forces. At small air-gaps, the forces are high and even small offsets modify the air-gap and hence significantly modify the forces. The maximum force difference when the $x_{off}$ and $y_{off}$ are zero is around 5.5 N.

Figure 25C:
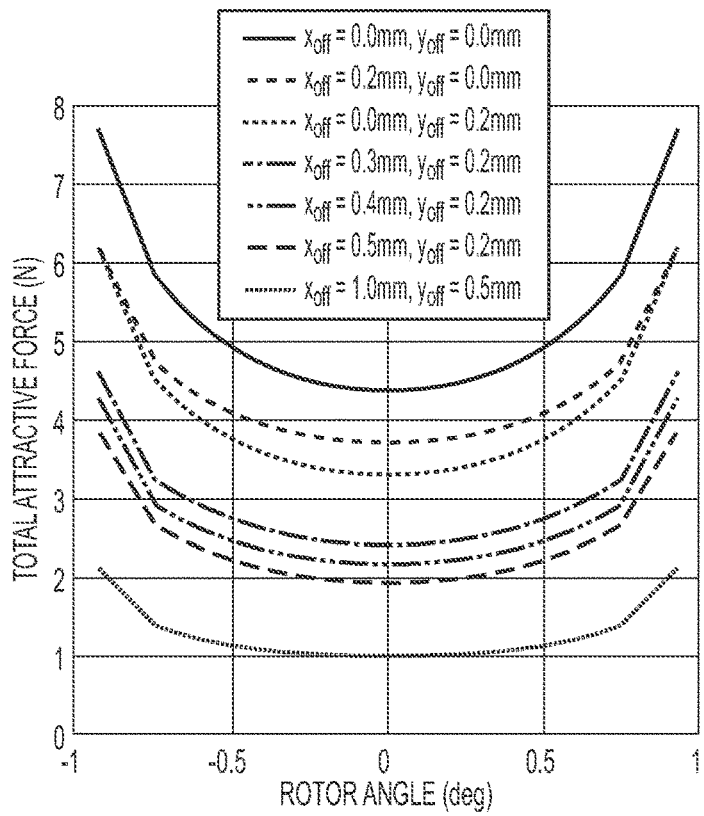

FIG. 25C shows the total attractive force, which is the sum of the forces on the right and left side on the rotor at various rotor angles. The notch flexure bearing experiences this load in operation. Again, there is no current through the winding. Magnetic force is very sensitive to air-gap and therefore the highest when the rotor is in contact with the stator pole face. When the rotor is in contact with the pole faces, the total vertical force increases and is the lowest at the neutral position. The maximum vertical force, when $x_{off}$ and $y_{off}$ are zero is around 7.5 N.

Amp-Turns Through the Winding:

FIGS. 26A-26C show the torque and force difference for various coil Amp-Turns (AT). The actuator configuration is such that for the assumed coil polarity, the magnetic field due to current in the winding adds to the magnetic field from the permanent magnet and increases the total magnetic field and the force on the left leg. On the other side, the field from the winding current counteracts the magnetic field from the permanent magnet and reduces the total magnetic field and force on the right side.

The result is a net force which is greater on the left side and will cause the rotor to tilt in the opposite direction and make contact with the left pole face. Approximately 100 Amp-turns may be the minimum threshold current in the winding to cause the flipping of the rotor. Thus, if a current greater than 100 Amp-turns is provided, it should cause the rotor to flip. Of note here is that since even with 0 Amp-turns, once the rotor crosses the neutral point, there is net force on the left side. Therefore, if the current is switched off after the rotor crosses the neutral point, the net force is still on the left side which will bring the rotor to make contact on the left pole face. This latching behavior is due to the permanent magnets and is used to reduce power consumption in the actuator.

Figure 26D:
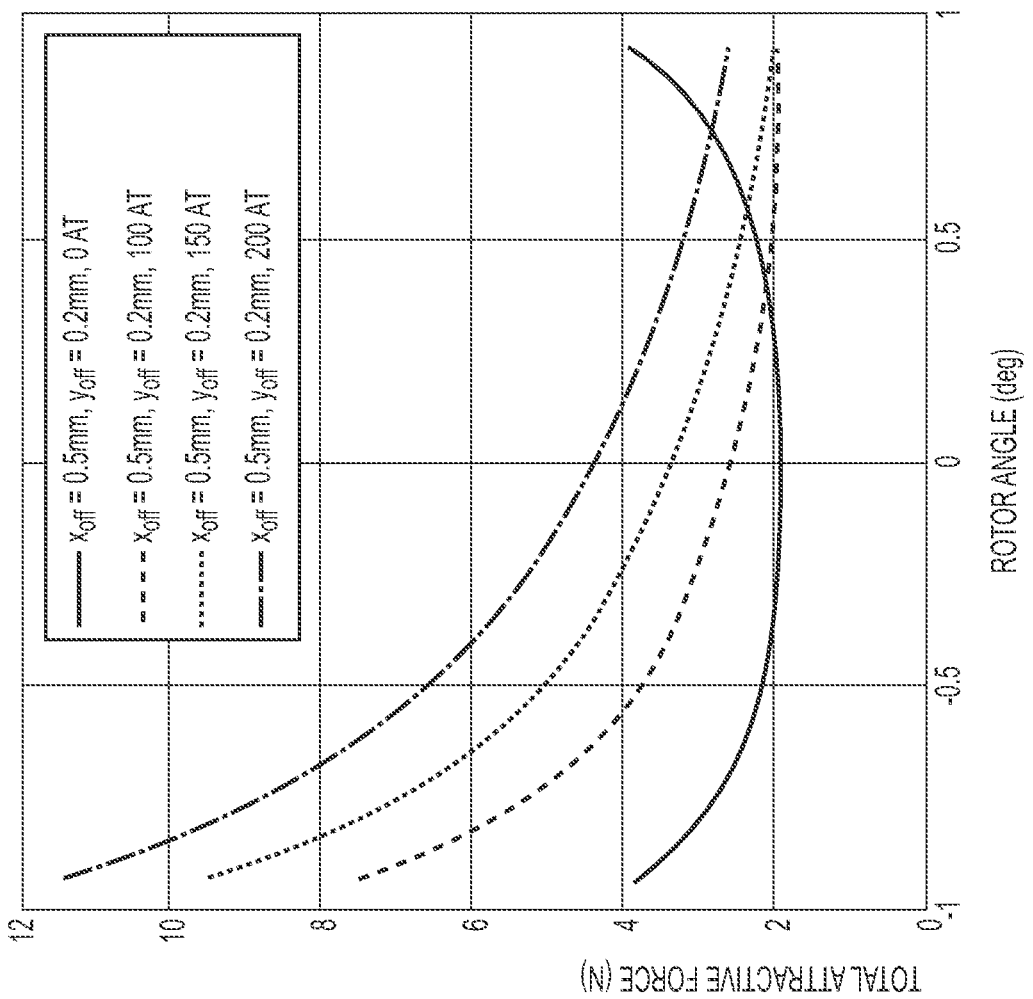

FIG. 26D shows the total attractive force, which is the sum of the forces on the left and the right side of the pole faces for the actuator when current flows through the winding. This is the total bearing force experienced by the notch flexure in operation. It is interesting to note that when the rotor is in contact on the right side, the total force reduces as Amp-turns are increased and reaches a minimum force at around 100 Amp-turns beyond which it increases again. At that minimum point, the total vertical force is almost zero as the magnetic flux from the winding almost completely cancels the magnetic flux from the permanent magnet on the right side. On the left side, due to the comparatively large air-gap, the forces due to the permanent magnet and the winding magnetic flux are much weaker.

Magnetic Field Distribution within the Stator and Rotor During Operation

FIGS. 12A-12F shows the magnetic flux density (B) plots as a vector plot depicting magnitude and direction of the B-field on the right. The plots in FIGS. 12A, 12C, and 12E represent the case with no current through the winding. The plots in FIGS. 12B, 12D, and 12F represent the case with 150 Amp-turns of current through the winding. These plots provide the behavior of the actuator. When the rotor is contacting the right pole face, the field from the permanent magnet on the right side makes a short loop through the pole face, into the rotor on the right side and closes back on the right permanent magnet travelling through air. This results in a strong latching force. On the left side, a smaller fraction of the magnetic flux goes through the rotor on the left side. The majority of flux from the left side permanent magnet goes through the stator to the right leg and returns to the left permanent magnet through the rotor and through air. There is slight saturation at some regions on the right side of the stator and rotor, but majority of the stator and rotor are not saturated.

When current is switched on in the winding with an associated flux direction shown by the arrow, the winding B-field counteracts the permanent magnet B-field on the right side while it adds to the permanent magnet B-field on the left side. There is no saturation of B-field in most regions in this case as well. This results in a net torque on the rotor and the rotor starts tilting to make contact with the left side pole face (FIGS. 12D and 12F). When the rotor makes contact on the left side pole face, the magnetic field is saturated on the left side near the pole face in the stator and the rotor. When the current is switched off (FIG. 12E), the system return to a state which is the mirror image about the vertical axis of the actuator with rotor contacting the right side with no current in the winding (FIG. 12A). When the rotor is in the neutral position, with equal air gap on both sides with no current in the winding (FIG. 12C), the magnetic field pattern is symmetric on both left and right sides and therefore there is negligible net torque on the rotor. When the coil is actuated (FIG. 12D), there is considerable B-field on both the left and the right pole faces. The field on the left side is much greater than the field on the right side and therefore, there is a net torque on the rotor titling it towards the left pole face.

In practice though, due to asymmetry in the manufacturing, there will be a net torque on the rotor even in the neutral position, but its value would be small compared to the net torque when the rotor makes contact with either pole face.

The simulations show that that a latching force in the range of 2-4.5 N may be achieved. The latching force is defined as the minimum force required to tilt the rotor to the other side when the rotor is in contact with a stator pole face. There will be a vertical force in the range of 2-8 N which will be supported by the notch flexure bearing. Flipping of the state of the rotor requires a current greater than about 100 Amp-turns.

2. Mechanical Design and Modeling

Force Required to Deflect the Membrane

The use of fluidic plates with the bonded COC membrane manufactured by microfluidic ChipShop GmbH as the platform is used to demonstrate pumping by these actuators. These fluidic plates are described in more detail in Example 4. "Fluidic plate" here refers to the top plate of the injection-molded test blocks. COC has a Young's modulus of 1.3-1.5 GPa. This translates to a reasonably high stiffness value and can therefore generate a modest amount of suction pressure to fill the pump chamber during the suction phase as well as to open the valves.

Table 8 summarizes the pressure required for a conical chamber of various diameters and depth of 0.1 mm for the diaphragm to make contact with the chamber walls. It was found that the force for deflecting a 3 mm diaphragm is around 525 mN. To achieve a back-pressure capability of around 15-20 kPa, that pressure should be added to actuation. For a 5 mm diameter diaphragm which is as large as may be used, a 20 kPa pressure translates into a force (pressure times area) of around 400 mN. Therefore, the total force at the contact point between the contact push button and the membrane may be about 1 N. The stiffness of the diaphragm is non-linear, with a small value for small forces and then the stiffness increases at an increasing rate as the force increases. For simplified analysis of the forces and deflections in the actuator elements, the stiffness is linearized. It takes 1 N for the push-button to deflect the membrane by 0.1 mm, including the back-pressure, so the linearized stiffness of the membrane is about 10 N/mm.

Forces and Deflections in the Actuator Elements

Figure 27A:
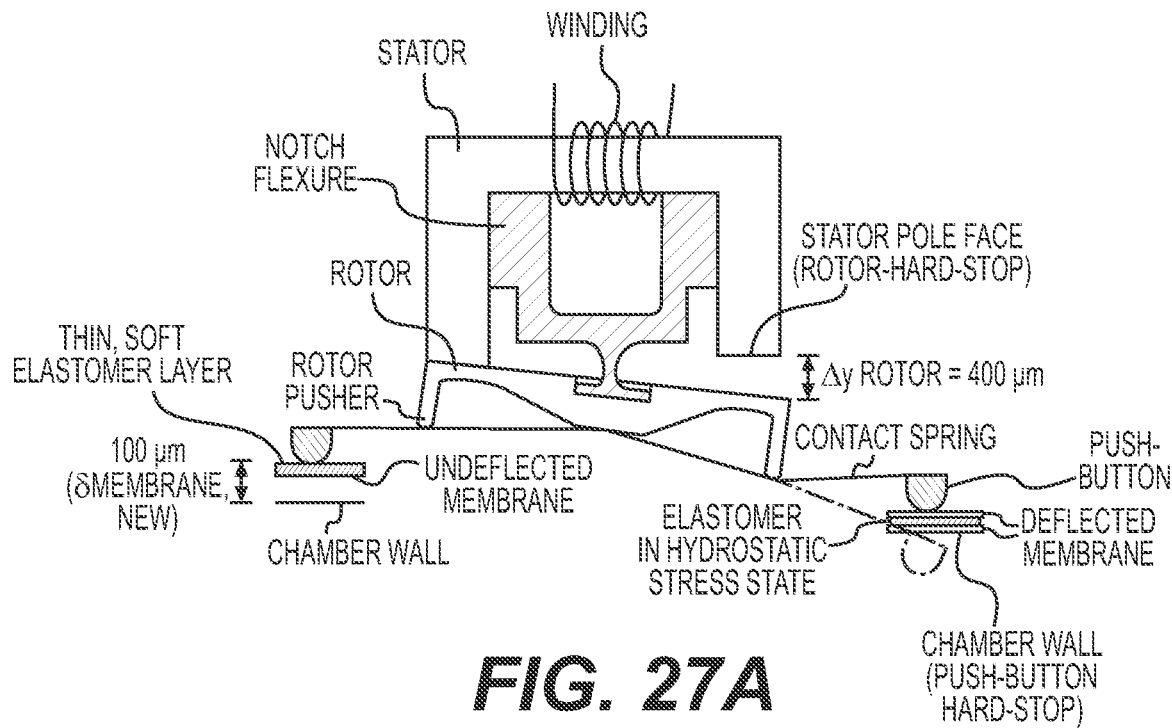
FIGS. 27A and 27B are schematics of the actuator deflecting the membrane on the right and no contact with the membrane on the left.
Figure 27B:
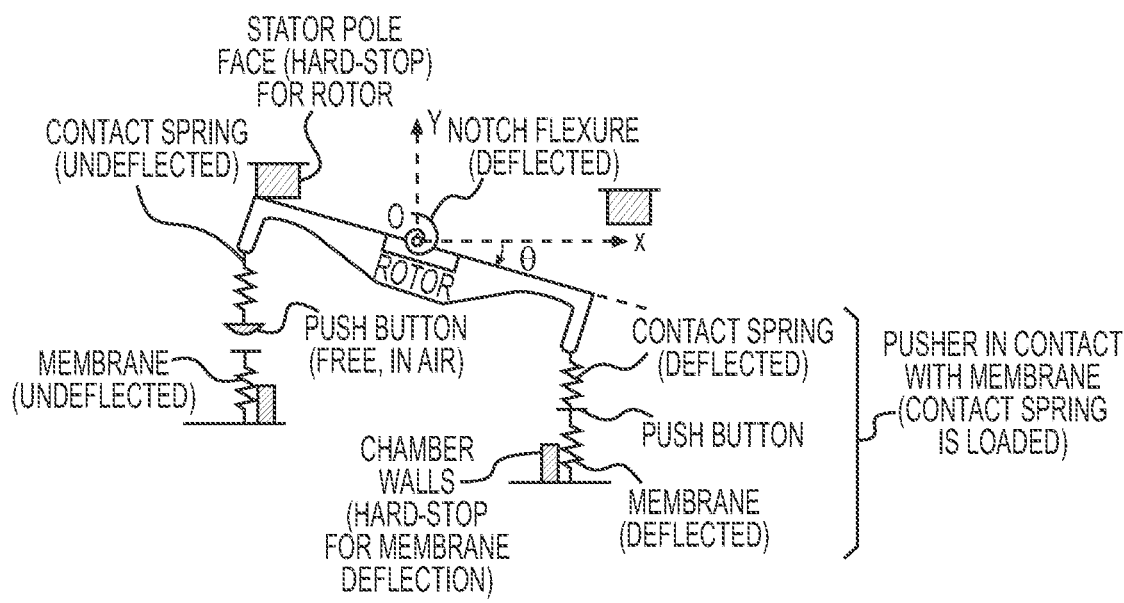
Figure 28:
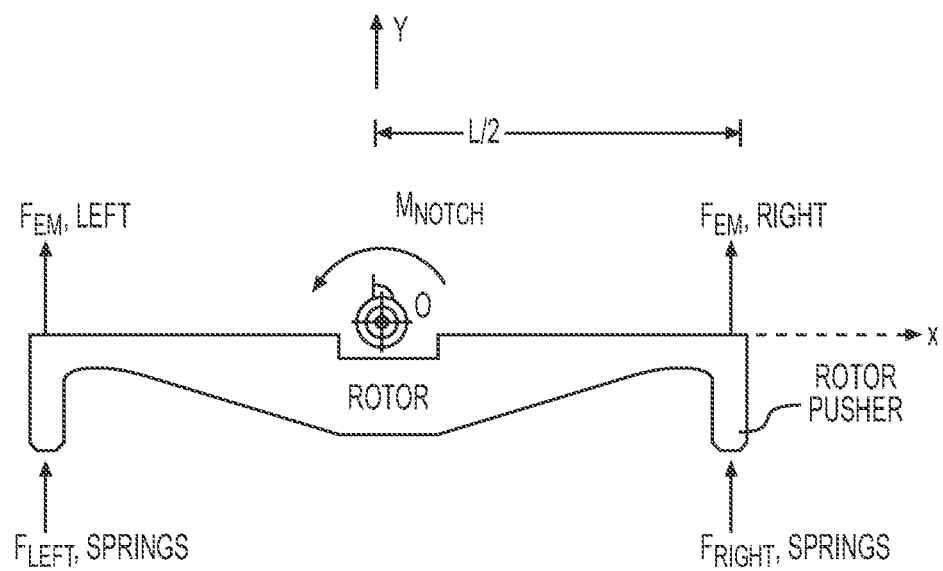
FIG. 28 is a free-body diagram of the rotor showing the forces acting on the rotor. The EM forces, shown in red are from the permanent magnet and the winding current. The spring forces the force from the contact spring onto the pusher.

When the rotor rotates about the notch, the displacement of the rotor at each pole face is distributed between the contact spring, and the membrane which act as springs in series as shown in FIGS. 27A, 27B, and 28. The notch flexure in parallel with the contact spring and membrane and has the same total deflection. The rotor is assumed to be rigid compared to the other elements in the system. The sum of the deflections in the contact spring and the membrane add up to the total displacement of the rotor, while the notch flexure deflection is the same as the rotor displacement. Therefore, the force is the same through the contact spring and membrane and the total force from the rotor is distributed between the notch flexure and the contact spring and the membrane.

There are limits to deflection of the rotor and the notch flexure by the stator pole faces, and the membrane deflection is limited by the chamber walls. The maximum membrane deflection allowed is 0.1 mm. The maximum rotor deflection is 0.4 mm. As the membrane stiffness has been estimated above, provided here is an estimate of the stiffness and deflection range for the contact spring to have enough force (approximately 1N) and deflection capability at the point of contact with the diaphragm.

Preferably, the most of the force from the rotor is exerted at the contact with the membrane. Therefore, minimizing the stiffness in the notch flexure results in a low force in the notch flexure for a given deflection. In operation, the notch flexure is always engaged with 0 deflection at the neutral position of the rotor. During operation, for example, when the rotor is flipping after being latched with the right side pole face, the push button on the right side is initially not in contact with the membrane. The rotor has to move a certain distance before the push-button makes contact (FIGS. 27A and 27B). After the push-button makes contact with the membrane, the contact spring and the membrane are in series and further deflections of the rotor are distributed between them in the inverse ratio of their stiffnesses. Once the membrane bottoms out at the chamber wall, the membrane deflection stops and all further deflection of the rotor is accommodated only by the contact spring. Finally, the rotor deflection stops rapidly when the rotor comes in contact with the pole face on the left side.

Design of the Notch Flexure

The notch flexure is the bearing and the hinge for the rotor. In operation, it has to carry the preload from the permanent magnets as well as the net vertical force when the rotor switches to the other side. In addition, some fraction of the latching force is taken by the notch flexure while the remaining portion of the force is taken up by the contact spring and membrane combination.

Soemers, *Design Principles for Precision Mechanisms*. Enschede, the Netherlands: T-Point Print VoF, (2010), gives the design charts and rules for designing notch flexures for small rotation angles of up to 1°. An excel spreadsheet was made to easily evaluate various materials and actuation conditions. The important geometrical dimensions of the notch flexure are the notch height h, notch diameter D and the thickness t. An exemplary design is a notch flexure made of poly-carbonate, with h=0.3 mm, D=1.5 mm and t=4.763 mm (same as thickness of the stator). For such a notch, the stiffness in the vertical direction is around 2000 N/mm which results in a vertical deflection of approximately 5 μm for a vertical load of 10 N, which is much smaller compared to the membrane deflection of 100 and the maximum actuator air gap of 400 Since there is further motion of the rotor after the membrane bottoms out, this deflection can be accommodated in that extra motion. The rotational stiffness of the notch flexure along the notch axis is around 80 Nmm/rad. For a rotation angle of approximately 1°, the torque required is thus around 1.5 Nmm. This translates to a linearized stiffness of 0.8 N/mm at the rotor edge. The pole faces are approximately 10 mm away from the notch center and therefore, the force at the pole face taken by the notch flexure when the rotor is latched is around 0.15 N. This is less than 10% of the latching force of 2-4.5 N, and hence the force in the notch flexure may be neglected when designing the contact spring. The maximum stress in the notch flexure is around 10-15 MPa, which is less than ⅓rd of the yield strength of polycarbonate—around 60 MPa (nominal). Therefore, the poly-carbonate notch flexure should have a long life in operation.

The deflection of the notch flexure using mechanical FEA was also verified. The displacement and the stresses were within acceptable range. Since the stresses were within ⅓ times the yield stress, the notch flexure is expected to have a long life in operation.

Autodesk Fusion 360 in non-linear simulation mode was used for the FEA. Due to the contribution of the vertical force in addition to the moment, the deflections and forces are higher than calculated above, but still remain within an acceptable range. The beam supporting the notch has a bending deflection of around 10 μm which can be reduced by reinforcing the beam against the winding and the permanent magnets (FIG. 10), as will be the case if the actuator is potted in epoxy or some other material as a part of the manufacturing process.

Design of the Contact Spring

The contact spring helps bound the contact force with the membrane due to its lower stiffness and low mass of the push-button. It also ensures that independent of the exact membrane deflection, the rotor always goes into a latched state. In addition, the spring stores energy which serves to decelerate the rotor into contact, and which can be used on the return stroke to assist in faster switching of the actuator.

Figure 30A:
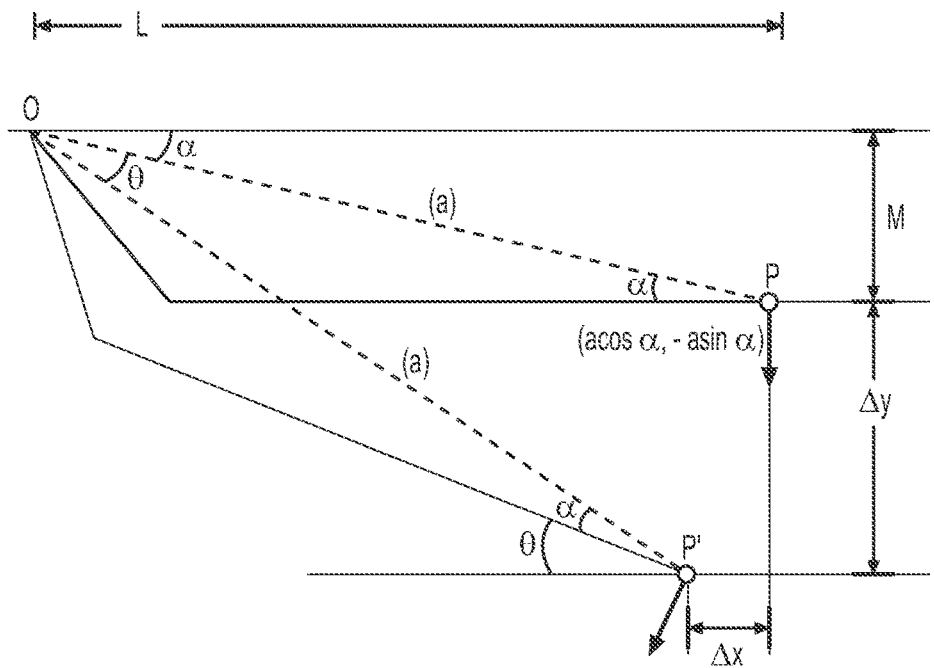
FIGS. 30A and 30B are diagrams showing the rotation of the rotor and contact spring. O is the notch rotation axis and P is the push-button's bottom surface. When the rotor 752 rotates and the pusher 754 moves down by Δy, there is a horizontal component of the displacement, Δx and also a tilt angle, θ.

The kinematics of contact is an important consideration. The required deflection of the membrane is in the vertical direction into the pump and valve chambers. When the rotor tilts along the pivot axis, it creates a horizontal component of the motion along with vertical which can cause sliding of the push-button on the membrane surface (FIG. 30A). In addition, the push button in contact with the membrane is also tilted with respect to the vertical. This tilting is potentially problematic as the displaced volume would then be limited to the intersection of the tilted push button geometry when the membrane comes in contact with the walls of the pump chamber. This volume is lower than if the push-button comes down vertically into the chamber. For valves, a conformal contact of the diaphragm against the sealing lands is needed to create a seal and the tilted push button may increase chances of gaps between the diaphragm and the sealing lands.

To accommodate these deviations, an elastomeric layer was used between the pushbutton and the membrane (FIG. 27A). The thicker the elastomeric layer, the larger deviations it can accommodate, but in return it reduces the vertical stroke of the actuator acting to deflect the membrane or to store energy. To minimize these deviations minimizing the tilt and horizontal motion of the push-button may help. Therefore, the contact spring is designed such that it can deflect and transmit force to the membrane as the rotor rotates and at the same time, minimizes the horizontal travel and the tilt at the point of contact of the push-button when the membrane is in its fully deflected condition.

FIG. 30A shows the rotation of point P about a point O. Point O corresponds to the center of the pivot flexure. Point P corresponds to the tip of the push-button, which would lie at the end of the contact spring. Point P is located at a vertical distance H below and horizontal distance L to the right of O. When the rotor rotates, point P moves to P'. The distance moved vertically is Δy. The corresponding distance moved in the horizontal direction, to the left is Δx. The horizontal motion is, $$\Delta x = \frac{H}{L} \Delta y \qquad \text{Equation 5.1}$$

For a vertical motion of Δy=0.2 mm downwards, and nominal L=12 mm (the horizontal distance between the vertical mid-plane to a stator pole face) and nominal H=6 mm (the vertical distance between the pivot center point and the bottom of the push-button), therefore, Δx=0.1 mm to the left and a θ=Δy/L=1° tilt to the left with respect to the vertical. This horizontal motion is a fraction H/L times the vertical motion. Since the chambers are shallow, the push-button can potentially accommodate this motion by moving into position by sliding on the membrane. The tilt is potentially more problematic and therefore the tilt may be removed and the horizontal motion for a given vertical motion of the push-button may be minimized and at the same time allow the rotor to rotate about the pivot center and make contact with the pole faces. As described earlier, further deviations are accommodated by the elastomeric layer below the push-button.

Figure 29A:
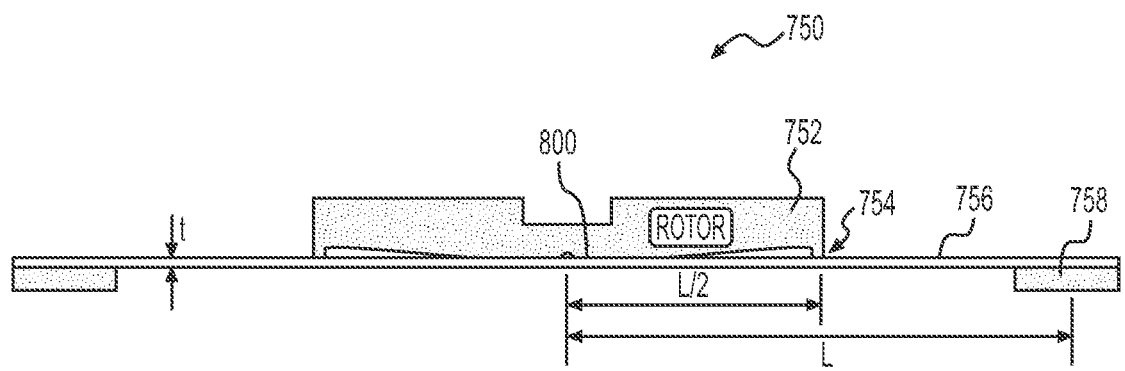
FIG. 29A is a diagram showing the front view of the contact spring and rotor assembly 750 and FIG. 29B is a diagram showing the plan view of the contact spring 756. The pusher 754 is at the edge of the rotor 752 and engages with the contact spring 756 after the push-button 758 makes contact with the membrane (not shown). It deflects the contact spring at the middle and removes the tilt from the push-button after membrane contact. The spring is micro-TIG welded to the rotor at the center point 800.
Figure 29B:
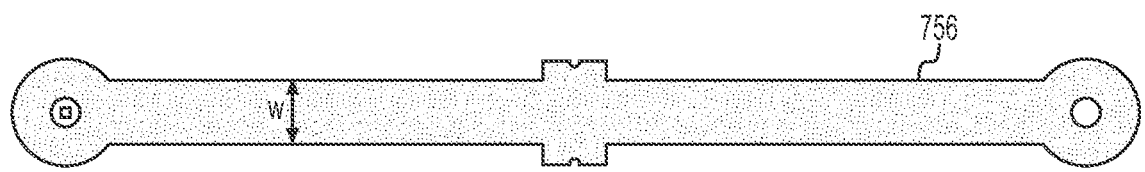
Figure 30B:
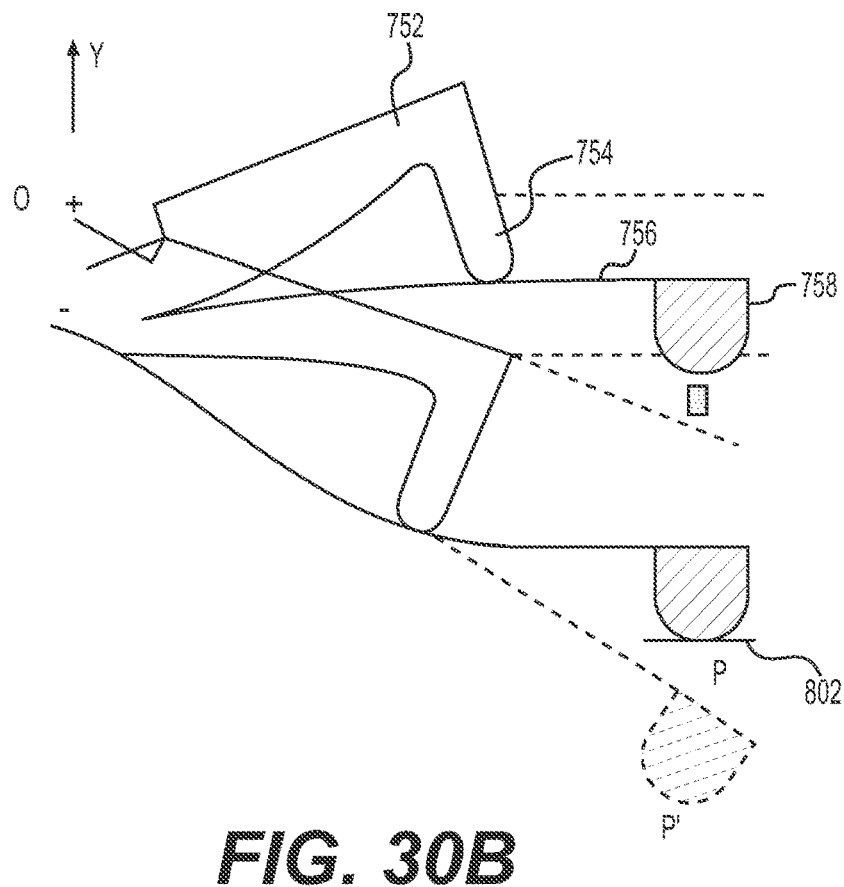

One of the solutions to resolve this is to have a force acting vertically between points O and P to provide a counter moment in between the O and P to remove the tilt once the push-button makes contact with the membrane. This is accomplished as shown in FIGS. 30A and 30B. The rotor is modified to have a contact point at the mid-point of the contact spring and thus pushes in the middle of the contact spring as shown in FIGS. 29A and 29B. When the contact spring makes initial contact with the membrane, the effective length of the contact spring is from the center of the rotor to the push button. After contact with the membrane, due to the membrane resistance, the pusher engages with the contact spring. Consequently, the effective length is reduced by half, to the distance between the pusher to the push-button. Therefore, the contact stiffness at the time of contact is around 8 times smaller than the stiffness after contact. This is because the vertical stiffness of a loaded beam is inversely proportional to cube of the length. The reduction of effective length by 2 times, increases the stiffness by 8 times after contact. This minimizes the impact forces on the membrane. Once the pusher is engaged, it also provides a counter moment which removes the tilt from the pusher as shown in FIGS. 30A and 30B. The modified design of the rotor with the pusher at the middle of the contact spring is shown in FIGS. 29A and 29B. The contact spring is attached to the rotor by micro-TIG welding at the center since the joint will bear significant moments which try to peel the contact spring away from the rotor. Welding gives a joint which is strong in all directions whereas bonding is typically weak in peeling and cleavage directions.

An alternative solution may be to attach a cantilevered beam at the end of the rotor. Kinematically, the cantilever at the push-button will move horizontally to accommodate the reduction in vertical height at the rotor. In addition, the contact stiffness of the cantilevered spring is almost 8 times the contact stiffness of the midpoint pusher design. This may have a higher stiffness (almost 8 times) during impact compared to one described above. In addition, as the rotor edge moves down, the cantilever at the push-button will move horizontally to accommodate the reduction in vertical height at the rotor. The solution presented here minimizes the vertical downward motion by keeping the other end close to the pivot point and consequently minimizes the horizontal motion. Other flexure spring designs may be such to keep the push-button vertical as the rotor edge moves down but they would be more complex than the solution described earlier and were therefore not utilized.

Contact Spring Deflections

After membrane contact, the region from the pusher to the push-button acts as a cantilever beam with spring stiffness given by $$k_{contact\text{-}spring} = \frac{F}{\delta} = \frac{3EI}{(L/2)^3} \quad \text{Equation 5.2}$$

where F is the force on the push-button, δ is the deflection of the cantilever beam (contact spring deflection), E is the Young's modulus of the contact spring material, I is the beam bending moment of inertia, and L is the length of the contact spring from the rotor center to the push-button.

The contact spring and the membrane act like springs in series. As the pusher moves down by a certain amount, $\Delta y_{pusher}$, the pushbutton moves down by $2 \times \Delta y_{pusher}$ if unobstructed. The actual motion would be smaller due to resistance by the membrane. At the end of motion, when a side of the rotor (pusher) is in the lower-most position, $\Delta y_{pusher}$=400 µm, the contact spring should be parallel to horizontal. This position would be the lowermost position of the pump/valve chambers and hence is a hard-stop for the membrane and the contact spring deflection. If unobstructed, the position of the push-button would be at 800 µm, but due to being stopped by the chamber walls, it is at 400 µm, keeping the slope 0. Hence the contact spring deflection is 800 µm−400 µm=400 µm.

This spring deflection can be increased by giving an offset deflection in the vertical direction by increasing the length of the pusher by Δo. In the electromagnetic design, a Δo=200 µm is considered. The maximum spring deflection achievable then is $\delta_{contact}$=400 In this configuration, the contact spring is at the neutral position line when the rotor is at the top most position. In manufacturing, the pusher length offset may be implemented, Δo either by increasing the length of the pusher or by using thin shim strips of the required thickness between the pusher and the contact spring.

After contact of the push-button with the membrane, the contact spring and membrane have the same force F and distribute the deflections. Let the membrane deflection be $\delta_{membrane}$ (maximum value=0.1 mm), and the deflection of the contact spring be $\delta_{contact\text{-}spring}$. Further, define the total deflection at the push-button as $\delta_{cm}$. The equation describing the forces and deflections is then, $$F = k_{contact\text{-}spring}\delta_{contact\text{-}spring} = k_{membrane}\delta_{membrane} = k_{series}\delta_{cm} \quad \text{Equation 5.3}$$

where $k_{series}$ is the series spring-stiffness of the contact spring and the membrane together given by, $$k_{series} = \frac{k_{contact\text{-}spring} k_{membrane}}{k_{contact\text{-}spring} + k_{membrane}} \quad \text{Equation 5.4}$$

The deflections are related as, $$\delta_{cm} = \delta_{contact} + \delta_{membrane} \quad \text{Equation 5.5}$$

The stiffness required of the contact spring may then be estimated. For a deflection value of the contact spring, $\delta_{contact\text{-}spring}$=0.4 mm, the membrane should deflect by $\delta_{membrane}$=0.1 mm. Since the force in the contact spring and the membrane is the same (Eq. 5.4), the stiffness of the contact spring is, $$k_{contact} = \frac{k_{membrane}\delta_{membrane}}{\delta_{contact\text{-}spring}} \quad \text{Equation 5.6}$$

Substituting the values, with $k_{membrane}$=10 N/mm, then, $k_{contact}$=2.5 N/mm. This is the lower bound of $k_{contact}$ and is determined by the ability to deflect the membrane within the deflection range allowed (1 N for 0.4 mm deflection). The upper limit of $k_{contact}$ is determined by the force available from the electromagnetic latching force between the rotor and the stator pole faces.

The elastomer below the push-button has negligible stiffness till a critical deflection. Once the critical deflection is crossed, the stiffness drastically increases and the elastomer acts like a rigid component. This critical deflection is assumed to be equal to half the thickness. For the analysis, the overall effect of the elastomer at the end of the rotor stroke is that is reduces the total available deflection of the contact spring by half the thickness of the elastomer.

If the contact spring is stiffer, the membrane bottoms out by touching the chamber walls before the rotor has completed its stroke. Once that happens, the additional displacement of the rotor is accommodated by the deflection of the contact spring. If there is a large excess latching force, then making the contact spring stiffer helps increase the energy storage in the spring. This stored energy is released in the reverse stroke and increases the speed of latching. Conversely, for a given speed of latching, the Amp-turns required would be reduced. The storage of energy in the springs also reduces the force on the rotor when it is neat the permanent magnets and helps reduce the velocity of impact of the rotor with the stator pole face.

For sizing the contact spring, the length is twice the distance between the rotor center to edge, i.e., L=25 mm. Spring steel was used as it has a high yield strength of 400 MPa. It has a young's modulus, E=200 GPa. To get a stiffness greater than 2.5 N/mm, a thickness, t=0.015 in (0.381 mm), and width, w=3 mm was chosen (FIGS. 29A and 29B). The resulting bending moment of inertia, I is $1.4 \times 10^{-2}$ mm⁴, and the stiffness of the contact spring, $k_{contact\text{-}spring}$ is 4.2 N/mm.

Em Actuator Elements During Motion: Forces, Deflection and Dynamics

Figure 31:
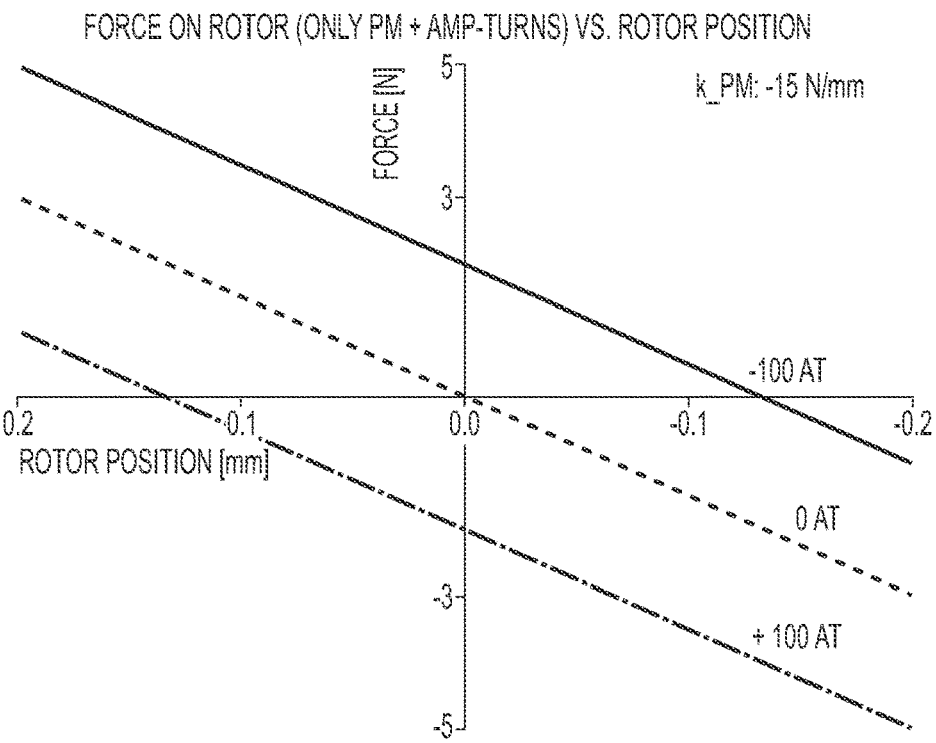
FIG. 31 is a graph showing the net force (N) on the rotor right-side due to the permanent magnet (PM) as it depends on the winding current (AT) vs. rotor position (mm). Positive force is in the upward direction on the rotor right-side. The rotor position is the vertical displacement of the rotor right-side from the neutral position. When there is no current in the winding, the latching force is 3 N at ±0.2 mm displacement associated with pole face contact. The addition of ±100 Amp—turns of current offsets the force due to the PM by ±2 N, thus causing almost enough force to switch the rotor.

To simplify the dynamic modeling, a linear force displacement curve was estimated for each of the spring elements and derive the stiffness values. The same was done for the force due to the permanent magnets, which behave like springs with negative stiffness. When there is current though the winding, it is an approximation that the forces go up or down with a constant offset of 2N (FIG. 31). This is obtained by fitting a linear curve to the attractive magnetic force difference vs. rotor position with and without Amp-turns, shown in FIGS. 25A and 25B and FIGS. 26A, 26B, and 26C for the case of xoff of 0.5 mm and yoff of 0.2 mm. The stiffness values used are tabulated in Table 9. The model neglects frictional forces in the system.

TABLE 9

Linearized stiffness [N/mm] used for dynamics modeling. All stiffnesses are referenced to act at the pusher (rotor contact point with the contact spring).

| | |
|---|---|
| Permanent magnet | −15 |
| Membrane | 10 |
| Contact spring | 4.2 |
| Notch flexure | 0.8 |

Once the push-button makes contact with the membrane, the contact spring and membrane are like springs in series and the force is the same in both springs. The push-button moves twice the amount of the rotor if unobstructed.

In the discussions below, the stroke considered is the switching of the rotor from contacting the right pole face to making contact with the left pole face. All forces and displacements are referred to the right pusher of the rotor. The corresponding displacement of the right rotor (pusher) is from +0.2 mm to −0.2 mm. When the push-button is in air, the force on the push-button is negligible and therefore, as the rotor moves down by an amount $\Delta y_{pusher}$, the push-button moves down by an amount of $2 \times \Delta y_{pusher}$.

The total rotor stroke is 0.4 mm. The maximum displacement of the push-button is limited to 0.4 mm by the chamber walls once the membrane is fully deflected. When the rotor latches to the left side, the contact spring should be parallel to horizontal. The membrane, when it is not deflected, sits 0.1 mm above the chamber walls. Once the push-button comes in contact with the membrane, the contact spring and the membrane come in series and the deflection gets distributed. The displacement of the push-button, $y_{push\text{-}button}$ is, $$y_{push\text{-}button} = \min(\Delta y_{airgap} + \delta_{membrane}, 0.4) \quad \text{Equation 5.7}$$

where, $\Delta y_{airgap}$ is the airgap motion, and $\delta_{membrane}$ is the membrane deflection. The push-button displacement is limited to a maximum value of 0.4 mm.

The deflection in the contact spring is then the difference between the total displacement ($2 \times \Delta y_{pusher}$) and the push-button displacement ($y_{push\text{-}button}$).

$$\delta_{contact\text{-}spring} = 2 \cdot \Delta y_{pusher} - y_{push\text{-}button} \quad \text{Equation 5.8}$$

The relation between the membrane deflection and the contact-spring deflection, from Equation 5.6 is, $$\delta_{membrane} = \min\left(\frac{k_{contact\text{-}spring}}{k_{membrane}} \delta_{contact\text{-}spring}, 0.1\right) \quad \text{Equation 5.9}$$

where, $k_{membrane}$ and $k_{contact\text{-}spring}$ are the membrane and contact-spring stiffnesses.

These provide all the relations to calculate $y_{push\text{-}button}$, $\delta_{membrane}$ and $\delta_{contact\text{-}spring}$ as a function of rotor (right pusher) displacement, $\Delta y_{pusher}$.

Figure 32:
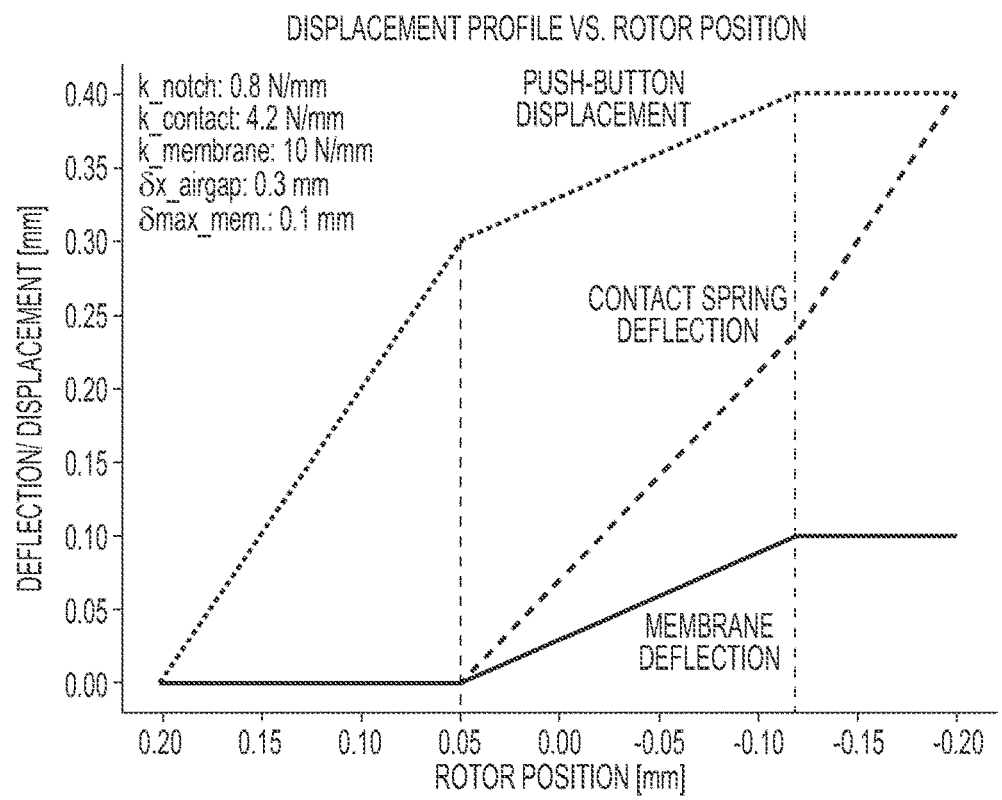
FIG. 32 is a graph showing displacement (mm) relative to rotor position (mm) of push-button, and deflection of contact-spring and membrane during rotor switching. The push-button moves freely through the air-gap until it comes in contact with the membrane. Then the displacement slope reduces due to resistance by the membrane and by the chamber walls after the membrane bottoms out, at which point the displacement is saturated at 0.4 mm.

The modeled push button displacement and the membrane and the contact spring deflections are shown in FIG. 32. When the push-button is traveling in air, till 0.3 mm, the deflection in the membrane and the contact spring is 0. After contact, the membrane and the contact spring deflect together until the membrane touches the chamber wall. After that, the push-button stays at the same vertical position due to the rigid chamber wall and the contact spring continues to deflect until it reaches a maximum deflection of 0.4 mm.

Figure 33A:
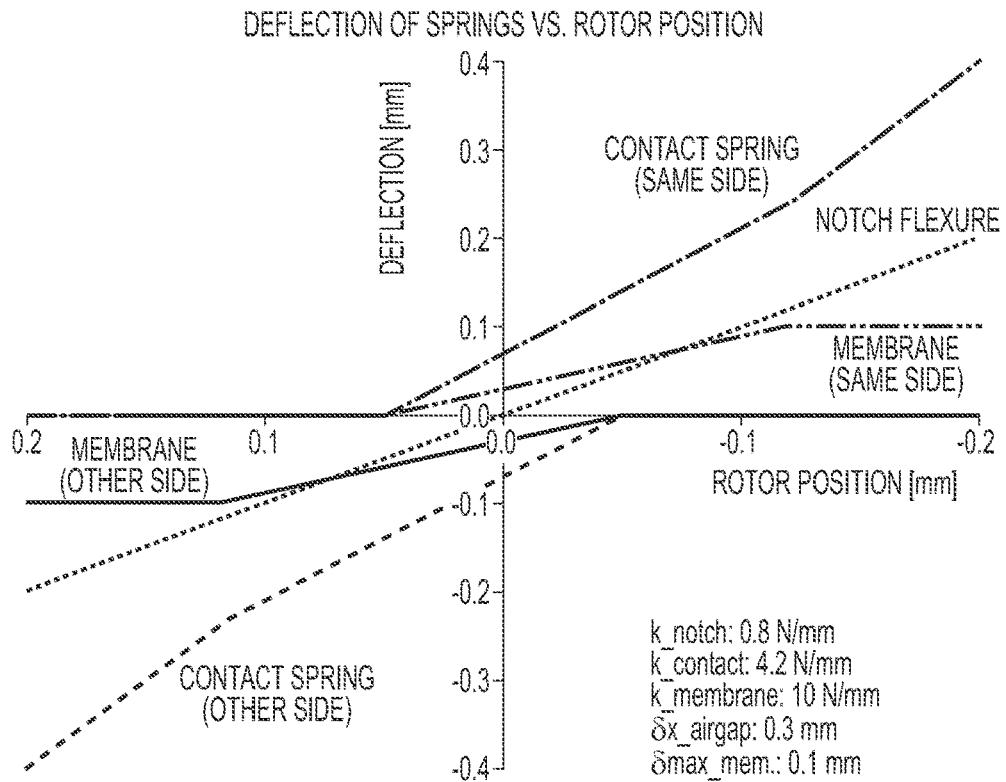
FIGS. 33A and 33B are graphs showing deflection (mm) of springs versus rotor position (mm) (FIG. 33A) and force (N) in springs versus rotor position (mm) (FIG. 33B).
Figure 33B:
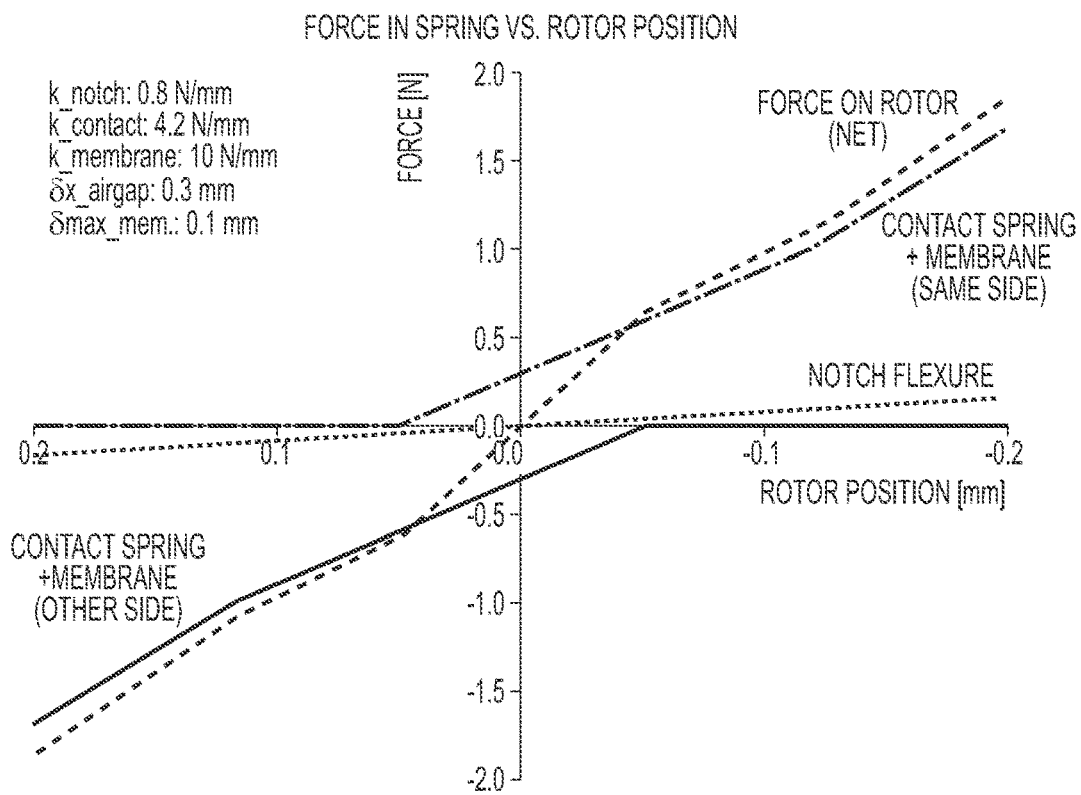

When the rotor is latched on the right, the contact spring on the left side is in its maximum deflected state. The deflection of the membrane, contact spring, and notch flexure is given in FIG. 33A. The corresponding forces in these spring elements is shown in FIG. 33B. All forces are referenced as if acting on the right side rotor pusher, with the up as the positive direction.

When the rotor is in contact with the right pole face, the springs on the left side are deflected which try to bring the rotor down. On the other hand, when the rotor is in the lower most position on the right side (in contact with the left pole face), the springs on the right side are deflected and try to push the rotor back up.

To simplify the modeling, symmetric deflections and stiffnesses on the left and right sides are considered. FIG. 33B shows the maximum force on the membrane at the end of deflection to be about 1.7 N. The force due to the notch flexure (0.15 N) is small compared to the forces in other spring elements and could have been neglected from the model.

Figure 34:
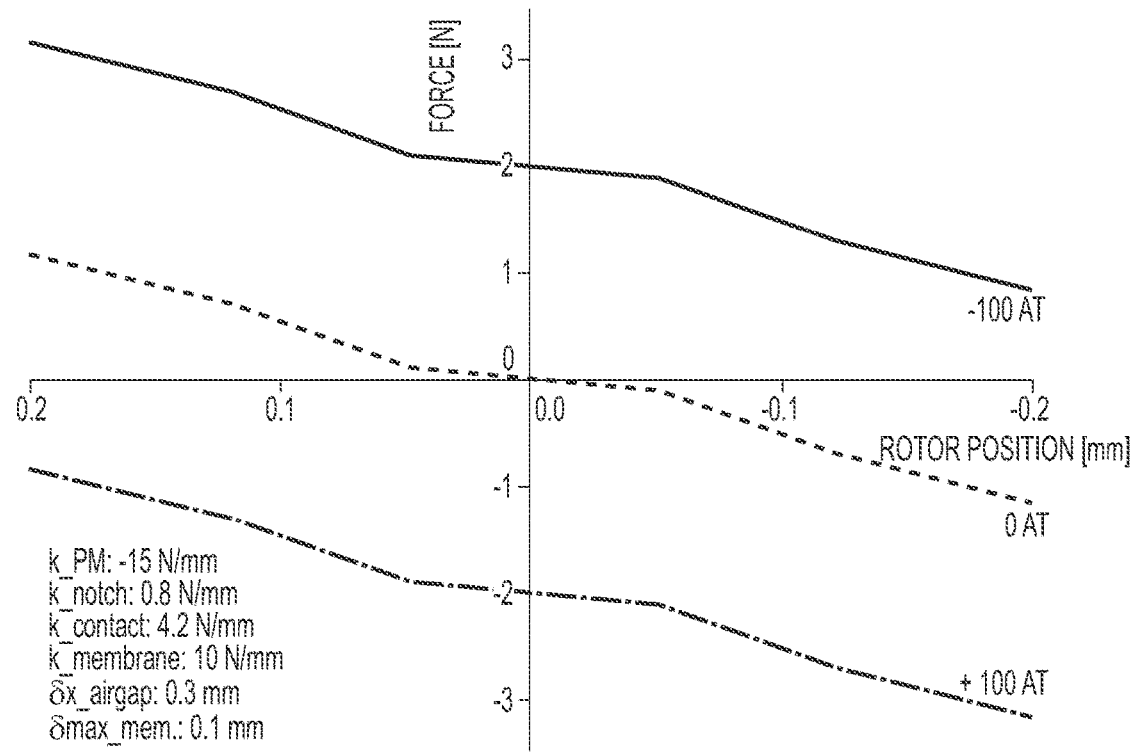
FIG. 34 is a graph showing force (N) on rotor versus rotor position (mm). Net force on the rotor including the effect of the electromagnet (FIG. 31 and the springs (FIG. 33B). The net latching force is reduced from 3 N (PM only) to about 1 N.

The spring forces can be superposed upon the electromagnetic forces, as modeled in FIG. 31 to obtain the net force on the rotor as shown in FIG. 34. When there is no current in the winding and the rotor is in contact with the top pole face, there is a net latching force of 1N. This is the buffer in force to accommodate variations in forces due to uncertainties in material properties, manufacturing and alignment. When there is a positive current of 100 Amp-turns in the winding, the net force becomes negative, which pulls the rotor down and causes it to move into latching on the other side. After the rotor crosses the neutral position, the net force is negative even if the current is turned off and the rotor will proceed to latch on the left side pole face.

Having obtained the net force on the rotor at every position in its stroke, the motion parameters—position, velocity and acceleration of the rotor with time may be found. Ignoring the damping and friction effects which would act to reduce the net force on the rotor, a rough estimate of the switching time may be obtained.

The angular acceleration of the rotor is $$\alpha_{rotor} = \frac{F_{net_{rotor}} \frac{L}{2}}{I_{rotor}} \quad \text{Equation 5.10}$$

where, $Fnet_{rotor}$ is the net force on the rotor at the right pusher, L/2 is approximately the radial distance of the pusher from the pivot point and $I_{rotor}$ is the rotational moment of inertia of the rotor. Since the mass of the contact springs and the contact push-buttons is negligible compared to the rotor, only the rotor mass is considered in calculating the rotor moment of inertia. The rotor is approximated as a slender bar of mass $m_{rotor}$ and length L, and its moment of inertia is, $$I_{rotor} = \frac{m_{rotor} L^2}{12} \quad \text{Equation 5.11}$$

The acceleration at the right pusher then is $\ddot{y} = \alpha_{rotor}(L/2)$. Given the net forces defined above, an expression for the acceleration of the rotor at every point y in its stroke is obtained. The position as a function of time is found using the following set of equations.

$$\ddot{y} = \frac{d\dot{y}}{dt} = \frac{d\dot{y}}{dy}\frac{dy}{dt} = \dot{y}\frac{d\dot{y}}{dy} \quad \text{Equation 5.12}$$

$$\int_{v_0}^{v} \dot{y} \cdot d\dot{y} = \int_{y_0}^{y} \ddot{y} \cdot dy$$

$$\frac{v^2(y) - v^2(0)}{2} = \int_{y_0}^{y} \ddot{y} \cdot dy$$

The initial velocity v(0) is 0 and the right-hand side is numerically integrated to get velocity as a function of position v(y). To find the position from velocity, $$v(y) = \frac{dy}{dt} \qquad \text{Equation 5.13}$$

Here, integrating dt to get the time on the left-hand side and integrating dy/v(y) to get the position on the right hand side. That is, $$\int_0^t dt = \int_{y_0}^y \frac{dy}{v(y)} \qquad \text{Equation 5.14}$$

Again, by numerically integrating the right-hand side, the time vector is obtained as a function of position, t(y). Therefore, the position and time information along the rotor stroke are obtained.

Figure 35:
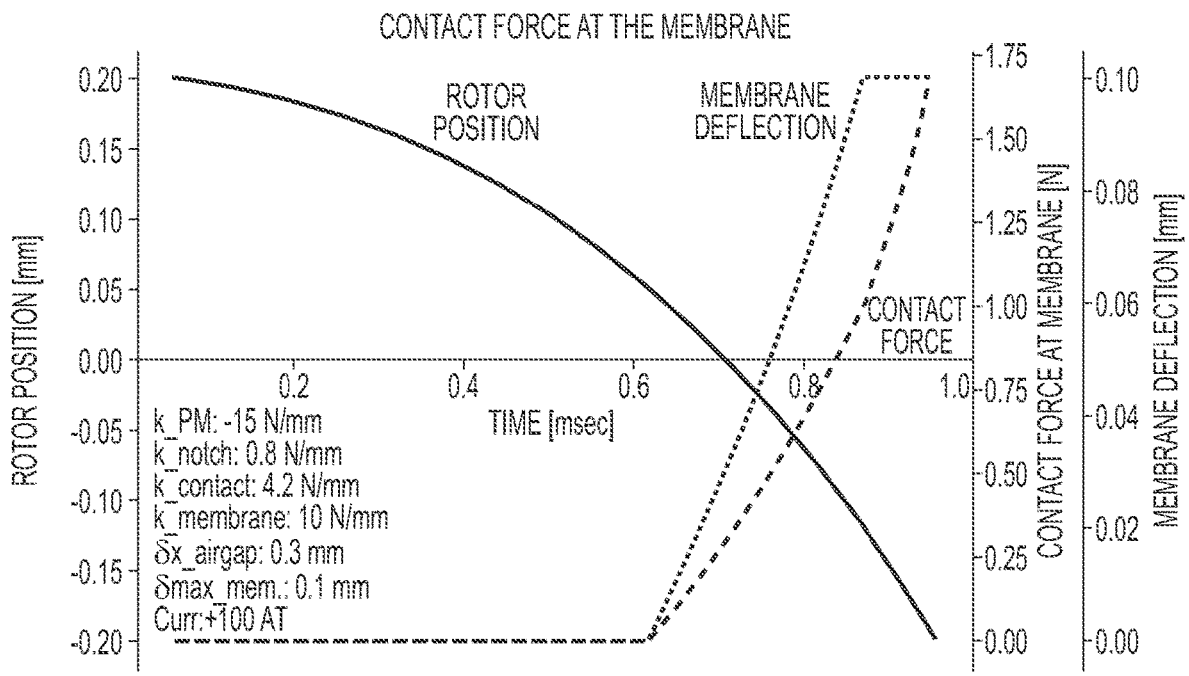
FIG. 35 is a graph showing contact force at the membrane (N) and the corresponding membrane deflection (mm) at different rotor position (mm). It is assumed that the rotor is initially latched to the right stator pole face. At time t=0, a current of 100 A-turns is applied in the winding, causing the rotor to begin to switch to the left side. Modeling predicts that the rotor should take about 1 msec for switching. The net force (sum of contact spring force and the electromagnetic (EM) force) acting on the rotor at the beginning of the stroke is small. The EM force rapidly increases as the rotor gets closer to the left side. This increasing force causes net acceleration of the rotor towards the other side and the velocity of the rotor keeps increasing. Rotor position is measured as displacement of the rotor measured at the right pusher. 0.2 mm stands for contact with the right pole face and −0.2 mm for contact with the left pole face.

A plot of the rotor position with time and the corresponding membrane deflection and contact force at the membrane is given in FIG. 35. The model predicts that the stroke should be completed in about 1 msec. The maximum contact force on the membrane is around 1.7 N, under the reasonable assumption that the spring and the push-buttons are massless.

Energy and Power Estimates

An estimate of the power consumption per stroke for the actuator can be obtained. Each pulse would need to be $\Delta t \sim 2$ msec (conservative bound) based on the modeling. The energy input to the actuator is by the current flowing through the winding. If there are 300 turns of wire, then 100 A-turns of current means 0.3 A of current, i flowing through the wire. As a conservative estimate, an assumption is i=0.5 A if 150 A-turns are required.

A conservative winding resistance of 10Ω is used. A measured resistance of same number of winding in similar actuators to be about 5-6Ω. Then, the energy consumption per stroke is, $$E = i^2 R \Delta t \qquad \text{Equation 5.15}$$

Figure 36:
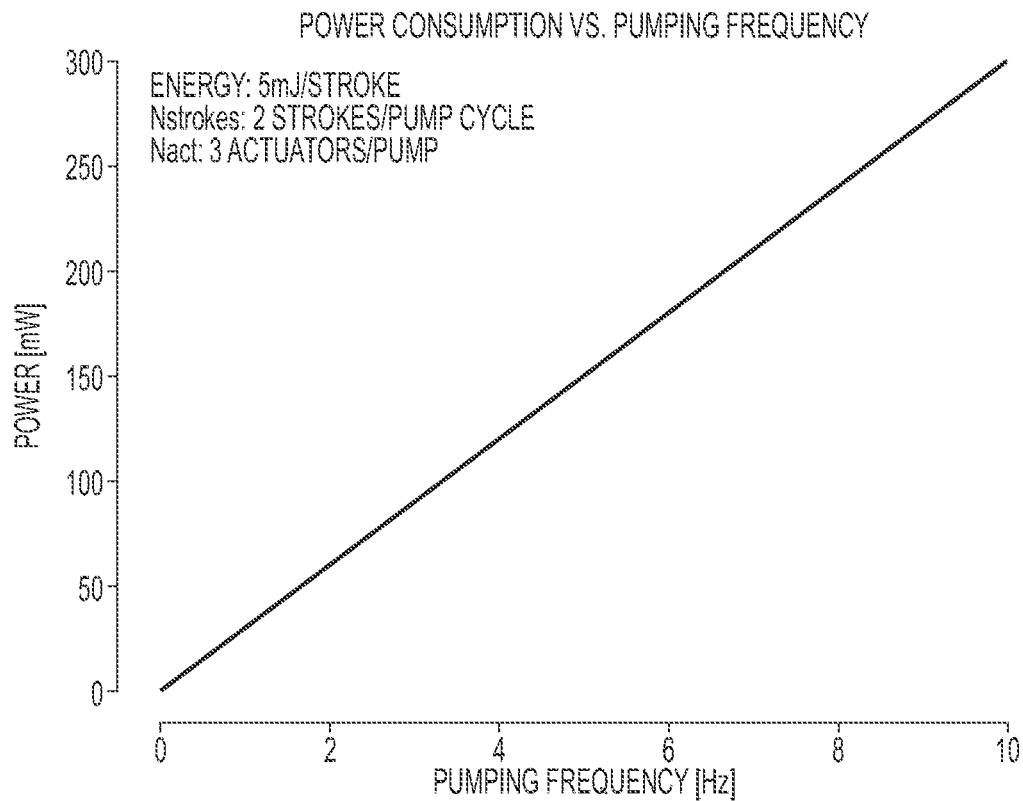
FIG. 36 is a graph showing power (mW) consumption versus pumping frequency (Hz) of the EM actuator. Modeled power consumption vs. pumping frequency for the EM actuators is shown.

Substituting the values, $E = 0.5^2 \times 1 \times 10^{-3} = 5$ mJ/stroke. Needed are 3 actuators (valve, pump, valve) for a pump channel. In each pumping cycle, every actuator undergoes two strokes—on and off. Then the power consumption is the product of the number of actuators and the actuation frequency which is shown in FIG. 36. In terms of power consumption, it is advantageous to operate the pump at lower frequencies. On the other hand, operating at higher frequencies allows for lower flow pulsatility. At 1 Hz actuation, the predicted power consumption is about 30 mW per pump, which is significantly lower than the power consumption of 500 mW per pump for the available 3-port pneumatic solenoid valves (SMC S070B-6CG). These valves are used to switch between pressure and vacuum for the pneumatic pumps and have a power consumption of 0.35 W per solenoid. Normally in a pump cycle, they are on approximately for half of the pumping cycle time.

Example 6. Integration, Manufacturing and Assembly of EM Micro-Pumps

Materials and Methods
Integration and Assembly Considerations

To enable pumping with the actuators, the injection molded, bonded membrane pump test blocks were used. The actuators were assembled such that the push-buttons could deflect the membranes by the desired amount, maintaining the desired deflection geometry of the various spring elements.

A rigid reference for the push-buttons was needed, once the membrane was deflected to the chamber walls. Therefore, the plate holder had a thick beam to support the platform. The plate holder had slots on either side of the beam and is elevated using rubber feet to allow for fluidic connections to the top plates from below. The pump block was secured using standard toe-clamps.

The actuator height above the membrane was determined by machined aluminum standoffs with shims. The whole actuator was secured with machined aluminum clamps using bolts which fix into threaded holes in the plate holder.

The parallelism of the rotor and the contact spring was achieved by machining flat the mating surfaces of the stand-offs and the stator. There was a clearance fit of the bolt within the holes of the clamps which allowed minor adjustments of the actuator in the horizontal plane so as to fine align with the pumps/valve areas on the top plate.

The electromagnetic actuator elements contained design features:

1. Stator

Stator modifications to facilitate easier assembly include features to bound the winding width (these may be snapped off after winding), extended handle (goes into a lathe or a rotary tool and can be cot after winding) connected to the connecting region of the stator, and features to give a reference surface for actuator mounting. The winding width is smaller than the distance between the stator legs so as to accommodate the notch flexure. This is achieved during winding by using template bars which are secured at the required distance using KAPTON® tape (E. I. du Pont de Nemours and Company, Wilmington, Del.).

2. Rotor and Contact Spring

The faces of the rotor contacting the stator poles are angled to have better contact and minimize the air-gap between the rotor and the stator pole contact faces.

The rotor also has a recessed surface at the bottom such that the rotor contacts the contact spring only at the center where the two are welded together and at the raised areas (pushers) on either side of the rotor. The rotor also has notch features to locate and align the contact spring before welding. The contact spring has corresponding notch features to locate on the rotor before welding, as well locating features to mount the pushbuttons. The assembly with the push-buttons bonded to the contact spring and the contact spring micro-TIG welded to the rotor was manufactured.

Manufacturing of the Components

Table 10 lists the materials and the fabrication methods used to fabricate the various components.

Assembly of the FM Actuator Pump

The sequence of steps followed to assemble the EM actuator module and integrating them on the plate holder were as follows:

1. The stator with the features was cut from stock low-carbon steel sheet on a water-jet cutter. Then the stator pole faces and the stand-off resting faces were milled on a machine tool to be flat and parallel to each other. The template for winding was then attached using KAPTON® tape and wound manually with the stator held in a rotating tool. For the final prototype, 450 turns were wound using AWG-30 winding wire. After winding, the extra features were removed, by snapping off or cutting on a band-saw.

TABLE 10

Component material and fabrication details.

| Component | Material | Source | Fabrication |
|---|---|---|---|
| Stator | 3/16" Thick Low-Carbon Steel | McMaster-Carr | Water-jet, Milling |
| Rotor | 3/16" thick low-carbon steel | McMaster-Carr | water-jet, milling |
| Permanent magnet | NdFeB N42 grade 3/16" × 3/16" × 1/8" | K&J Magnetics | — |
| Notch flexure | 3/16" thick poly-carbonate | McMaster-Carr | Water-jet |
| Contact spring | 0.015" thick 1095 spring steel | McMaster-Carr | Water-jet |
| Push-button | clear SLA resin | Formlabs, Inc. | SLA 3D-printing |
| Winding | enamel coated winding wire | McMaster-Carr | — |
| Platform holder | 1/2" thick 6061 aluminum | McMaster-Carr | Milling |
| Actuator Standoff | 1/8" thick 6061 aluminum | McMaster-Carr | Water-jet, Milling |
| Actuator Clamp | 1/4" thick 6061 aluminum | McMaster-Carr | Water-jet |
| Elastomer layer | sorbothane, silicon | McMaster-Carr | |

2. The rotor was cut from stock low-carbon steel sheet on a water-jet cutter. The contact spring was cut from stock 1095 spring steel sheet on a water-jet cutter. The rotor and the contact spring surfaces were prepared for welding by sanding. They were then bonded together using a micro-TIG welder (Sunstone 200i2—Pulse Arc/Micro TIG Welder).

3. The notch flexure was cut from stock polycarbonate sheet on a water-jet cutter. The mating surfaces with the rotor and the stator were sanded, as preparation for bonding. First, the notch flexure was bonded to the rotor using cyanoacrylate (Henkel LOCTITE® 4851 and LOCTITE® 408, Henkel IP & Holding GMBH, Dusseldorf, Germany) adhesive. Then, the permanent magnets were placed on the stator with the correct magnet orientation, with both permanent magnets' north pole pointing into the stator. The notch-flexure bonded to the rotor was then aligned in position in the stator. An equal gap of 0.2 mm was maintained between the rotor top-face and the stator pole faces using shim-stock. The notch flexure and the permanent magnets were then adhesively bonded using cyanoacrylate (Henkel LOCTITE® 4851 and LOCTITE® 408) at the same time to the stator and allowed to set. An assembled EM actuator module is shown in FIG. 10.

4. The plate holder was milled on a vertical milling machine. Rubber feet were attached to it at 4 corners to give an elevation. Actuator standoffs and clamps were cut from stock aluminum sheet on a water-jet cutter. The bottom legs and top surface of the standoffs are milled flat and parallel on a machine tool.

5. The fluidic top plate was placed on the plate holder with one of its edges in contact with the reference edge on the plate holder. The electromagnetic actuator modules were then assembled on the plate holder. The required pump lane was aligned with the nominal center of the push-buttons and the top plate was secured with a toe-clamp. The actuators were then adjusted by hand to place the push-buttons over the center of the chambers.

6. Circular discs of 4-5 mm diameter were cut from layer of sorbothane (0.2-1 mm) using a knife or a die punch. This disc was then kept underneath the push-button for the valves with the help of forceps. A 4-5 mm circular disk was similarly cut from a thin layer of 0.050 mm silicone and kept under the pump push-button. A larger thickness was used for the valves as the valve deflection depth was smaller and a larger deflection from the contact springs could be obtained. This was because of the reduced effect of tilt in the push-button with increasing elastomer layer thickness. It was the pressure within the elastomer region that deflected the membrane against the sealing lands and caused it to seal. That is, the elastomer acted as a hydrostatic equalizer for the pressure from the push-button. For the pump chambers, it was important to have a deterministic deflection stroke and therefore, the elastomer layer was thinner.

7. The stators were positioned at the height required, with shims between the stator and the standoffs. The actuators were then secured in position using actuator clamps.

8. An electrical terminal block was attached to an edge of the plate holder. The winding leads were affixed to this terminal for easy connection to the amplifiers and to isolate them from any external strains.

Example 7. Testing of the EM Actuator

Materials and Methods

The EM actuators were tested independently, after assembly and before mounting on the plate holder, to measure the latching force and the current required to switch. For this, the actuator was mounted on its side, with the stator legs clamped using toeclamps. A square wave excitation was applied at a low frequency, and the current gradually increased in amplitude till the rotor flips. The current at which the rotor first flips is the minimum current required to flip without any restoring force from deflection of the contact springs. The associated latching force was measured by pushing on the air-gap rotor side with air-gap slowly increasing force until the rotor flips. The threshold force at which the rotor just flips is the latching force.

For the built actuators, there were 450 turns in winding. The winding resistance varied between 5.5-6Ω. The observed threshold current to flip was of 140-160 Amp-turns and a latching force between 4.3-4.7 N. The actuator inductance was measured to be about 15 mH, using Agilent 4284A Precision LCR Meter. The measurement frequency was 20 Hz, at a current level of 10 mA under the Ls-Rs function. At 100 mA current level, the inductance increased to about 23 mH.

A small variation in the minimum flipping current and the latching forces between the left and the right side were observed. This was most likely due to asymmetry in manufacturing to assemble the permanent magnets. When the rotor was close to the pole face, even small differences in geometries and placement of the permanent magnet can cause an observable difference in forces.

For pumping, the actuators and the fluidic top plate were mounted on the plate holder. The EM pump test setup included power supplies, PA10 linear power amplifiers, NI Compact RIO controller, fluidic tubing (connected to top plate), and a plate holder with top plate and EM actuator modules, with a close-up of the plate holder. The actuators run in a 6-step pumping sequence shown in Table 11. In each step of the sequence, there is change in state of one of the actuators. The actuation wave-forms are generated in National Instruments COMPACTRIO® (NI cRIO-9076, National Instruments Corporation, Austin, Tex.) running LABVIEW® Real-Time (National Instruments Corporation, Austin, Tex.). The software was developed using NI LAB VIEW® (National Instruments Corporation, Austin, Tex.). The waveforms were output as analog voltage signals between −10 and +10 V. They went to PA10 linear amplifier which amplifies the signal by 2 times and this amplified voltage is the voltage across the winding. The voltage divided by the winding resistance was the average current when the actuator was turned on. This current gave rise to a net differential in the magnetic flux between the left and the right side stator pole face, causing the actuator to switch its state.

For pumping actuation 3 degrees of freedom were used. The actuation voltage and the duration of excitation were the two degrees of freedom available in the actuator module. For each pump stroke, the duration that the pump stayed in a particular state before moving to the next state was specified (Table 11). This was the third degree of freedom. After the 6th step was completed, the system returned to step-1 and the cycle repeated.

Lane-5 of the fluidic top-plate, which had mid-wall valves with a chamber diameter of 4 mm and depth of 0.075 mm, and a conical pump chamber with diameter of 5 mm and depth of 0.1 mm was used. The actuators were tested for valve sealing by switching the actuators to open or close the valve. When the valve is open, the fluid is pushed through with a pressure-head and when the valve is actuated to a closed position, the valve stops the flow. Then the pressure head is increased till flow through the valve is observed. The flow-rate was measured using the time taken to travel a given distance of a fluid-air meniscus though the connection tube.

TABLE 11

6-step pump sequence for peristaltic diaphragm pumps with active valves. This sequence causes fluid flow in direction of valve-1 to valve-2. To reverse the flow, the pumping sequence may be reversed or the states between valve-1 and valve-2 may be switched.

| Step | Valve-1 | Pump | Valve-2 | Remarks |
|---|---|---|---|---|
| 1 | close | close | close | |
| 2 | open | close | close | |
| 3 | open | open | close | Suction stroke |
| 4 | close | open | close | |
| 5 | close | open | open | |
| 6 | close | close | open | Discharge stroke |

Results

The results showed that the valves sealed well up to a pressure of 60 kPa. This value was larger than the required 20 kPa sealing pressure. Pumping with the suction side (inlet) at atmospheric pressure and with 0 back-pressure was observed. Actuating at a 1 Hz pumping cycle, the volume discharged per cycle was found to be 0.45 µL/cycle. This was close to the maximum displaced volume possible of 0.48 µL for an intersection of a spherical cap of 15 mm radius with the conical pump chamber. The pumping sequence described in Table 11 was used with 340 ms for step-3 (suction stroke), 100 ms for step-6 (discharge stroke) and 15 ms for all other steps. It was observed that as the frequency increased, the flow-rate per stroke reduced. This was likely due to the low stiffness of the diaphragm near the zero deflection point. The pump chamber therefore, was unable to generates a high suction pressure and hence a high suction flow-rate. Therefore, it required a long time for the pump chamber to be filled during the suction stroke. Thus, the flowrate was primarily limited by the time required to fill the pump chamber in the suction stroke, which is driven by the diaphragm stiffness.

The testing showed that for an actuation voltage above 8 V, it was possible to switch for an excitation duration greater than or equal to 1 ms. The associated current through the winding for that short duration raised to about 0.4 A. The winding resistance was approximately 6Ω. Therefore, the instantaneous power dissipation in the winding was about 1 W, and the energy consumption per stroke was $E=i^2Rt \approx 1$ mJ/stroke which was lower than the initial estimate of the energy. At 1 Hz pump operation, the actuation frequency is 2 Hz and with 3 actuators per pump results in an average power consumption of $1 \times 3 \times 2=6$ mW per pump lane, which is low.

The steady-state temperature rise of the EM pumps was measured and was found to be less than 0.1° C. at the actuator winding coils. The pump was run at a pumping frequency of 1 Hz (2 strokes per second for the actuator) for over 90 minutes. The ambient room temperature was 22° C. throughout the experiment. A thermocouple connected to a multimeter with 0.1° C. temperature resolution was used to measure the temperature. This result makes the actuator suitable for use within a cell-culture incubator with very small effects on the nominal 37° C. temperature of the cell-culture medium, even for a platform using multiple actuators.

Preliminary tests with the actuator running for around 105 strokes (5 hours×5 Hz×2 strokes/actuation) showed all the elements of the actuator performing well at the end of the test.

Therefore, a scaled-up version of the electromagnetic pump was developed and tested as described herein. The pump used a teeter-totter EM actuator having a low energy consumption of about 1 mJ/stroke. This was achieved by a latching design which required only a short pulse of energy to switch its state and where springs store some of the actuator kinetic energy, which was then recovered in the reverse stroke. This further reduces the energy consumption of the actuator.

The results show the potential for the EM actuator for electromagnetic pumping. The actuators may be made sufficiently small, such as about 4 times smaller, to enable integrated actuation of multiple pump lanes while fitting onto a single platform.

Example 8. Linear Actuators

FIGS. 13F-13I are diagrams of linear variants of the EM actuators. FIG. 13J is a diagram of linear actuator with a cylindrical design.

FIG. 13H is a diagram of a linear actuator. The stator 522 is linear with a section in the middle ("inverted U") with coil windings 523. The permanent magnets 524 and 525 are attached to the two ends of the stator legs. The u-shaped mover 526 (in linear embodiments, the rotor is identified as "mover" since the motion is linear and not rotational) is attached to the stator using blade flexure 527. Any other flexure configuration providing constraints in 5 degrees of freedom may be used. The mover 526 moves linearly along the horizontal axis when actuated. The contact spring 528 is attached to the side of the mover leg, which helps with bounding the impact force, controlling the diaphragm deflection profile and angle, and stores energy used for the return stroke.

FIG. 13I is a diagram of another embodiment of the linear actuator shown in FIG. 13H. In this embodiment, the stator does not have an "invented U" middle section.

FIG. 13J is a diagram of another example of a linear actuator of a coaxial or a radially symmetric configuration. It can be made in cut sections of a cylinder or a cuboid, with access to the center winding. The inner region shows the stator 534 with the windings 536 and the permanent magnets with a bushing 530, which slides against the outer core, the mover 532.

Example 9. Modifications to Electromagnetically Actuated Diaphragm Micro-Pumps

The actuators may be made about 4 times smaller for integrated actuation of multiple pump lanes while fitting onto a single platform. Many of the principles described in the Examples 5, 6, and 7 may be used to guide the design as the actuator scales down.

A move may be made towards using more flexible membranes and then have some other means to provide a quick return to the diaphragm. This would enable working with smaller diameters and drastically reducing the force requirement. For example, to generate 20 kPa back-pressure with a 3 mm diaphragm, the force requirement is only about 0.15 N if the force required to deflect the diaphragm is negligible.

Figure 37:
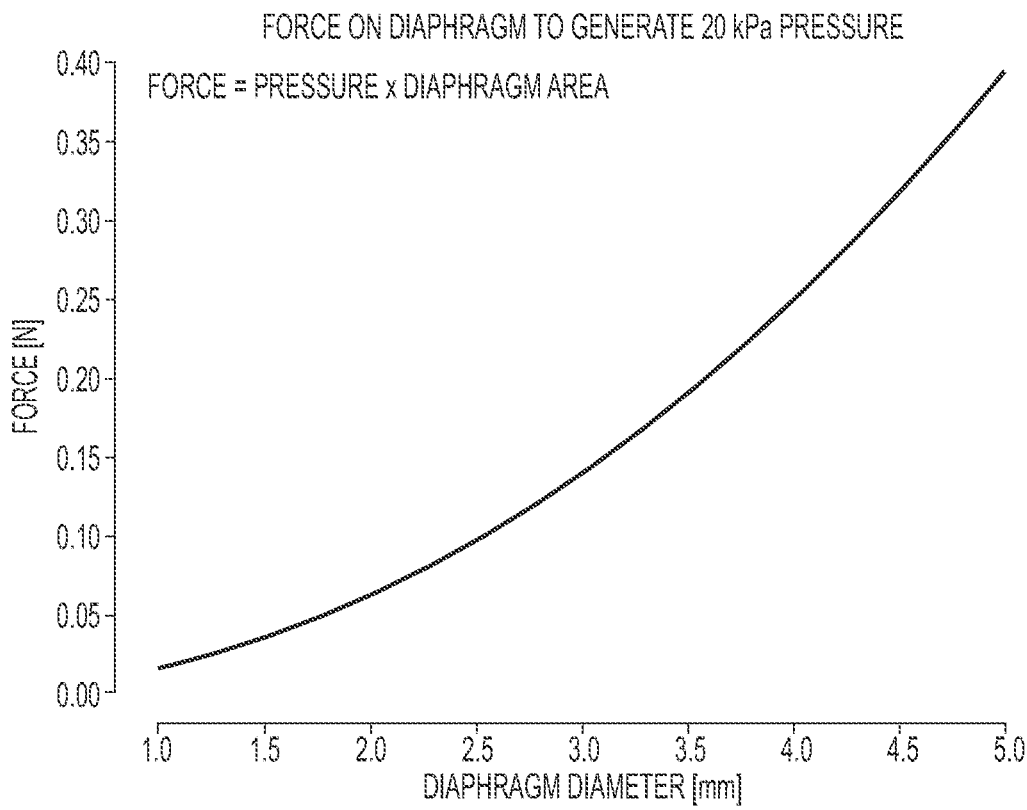
FIG. 37 is a graph showing the relationship between the diaphragm diameter (mm) and change in force (N) on diaphragm required to generate 20 kPa pressure. The force required to generate a given pressure quadratically increases with increasing diameter.

As shown in FIG. 37, the actuation force increases quadratically with increasing diameter of the diaphragm. For example, the force requirement, just to increase pressure to 20 kPa in a constrained volume of fluid through a 5 mm diaphragm is, force=pressure×area=0.4 N. Thus, going to a smaller diameter reduces the force requirement to generate a given pressure.

The diaphragm stiffness drastically increases with decreasing diaphragm diameter for the same thickness of the diaphragm (Example 1). Hence, the force required for a given deflection increases with decreasing diameter. In the described pumps, the return of the diaphragm is through this "self-stiffness" of the diaphragm. Therefore, the total force requirement is 1 N for a 5 mm diameter diaphragm against 20 kPa of back-pressure. These two requirements of larger diameter to reduce force requirement to deflect the membrane and smaller diameter to reduce the force required for a given pressure requirement are provided for guiding a scaling-down or scaling-up efforts.

Figure 38:
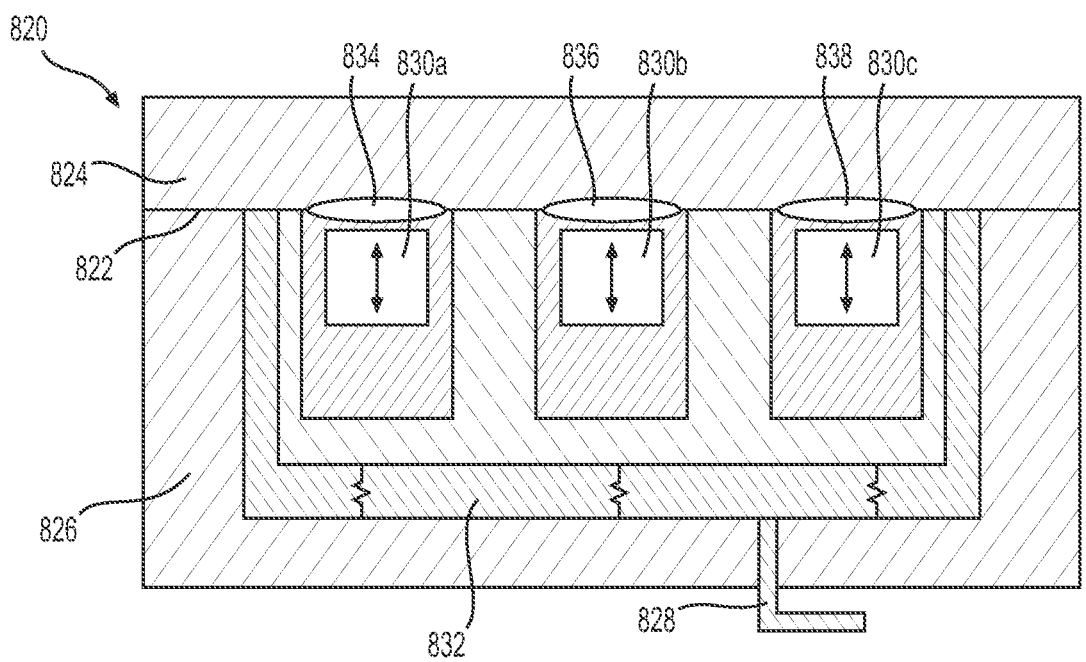
FIG. 38 is a diagram showing a segment of an MPS platform 820 with a vacuum preload for the diaphragm. The diaphragm 822 is bonded to the fluid plate 824. The fluid plate is preloaded against the pumping plate 826 using vacuum provided through the vacuum line 828. When unassembled, the EM modules 830a, 830b, and 830c rest within the pumping plate 826 on the preload springs 832. When the fluid plate 824 is assembled and vacuum is applied, the pumping plate 826 and the fluid plate 824 come into contact and push on each other. In addition, the vacuum pulls the fluid plate 824 towards the EM modules 830a, 830b, and 830c and the vertical position is controlled by the contact between lands (not shown) of the EM module 830a and the fluid plate 824 surface. In operation, vacuum pulls the diaphragm 822 away from the pump chamber 836 and valve chambers 834 and 838 and towards the EM actuators 830*a*, 830*b*, and 830*c*. In operation, the EM actuator pushes the diaphragm towards the chamber walls and the diaphragm return is by the vacuum preload.

One solution to provide the return force for the diaphragm is to bias the diaphragm deflection as shown in FIG. 38. This approach uses vacuum to pull the diaphragm away from the pump chambers when the actuator is not pushing on the diaphragm.

Figure 39:
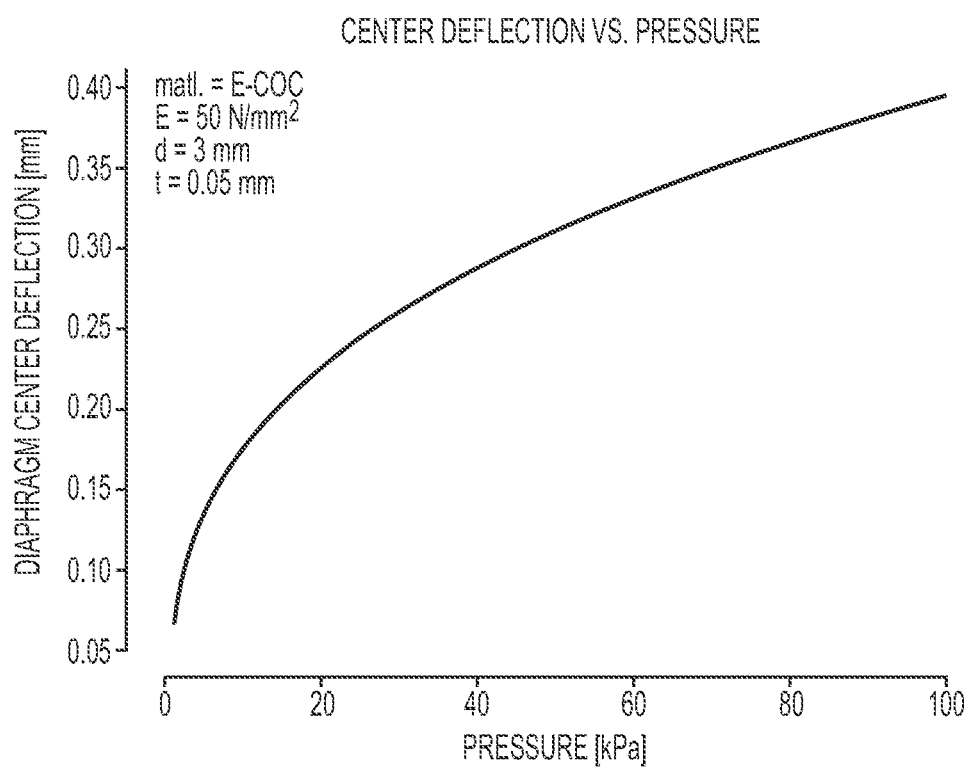
FIG. 39 is a graph showing the change in diaphragm center deflection [mm] with varying pressure (kPa) for the E-COC membrane. E-COC membrane has much lower stiffness compared to regular COC membrane. The pressure required for 0.1 mm diaphragm deflection is only around 5 kPa, which translates to a force of 0.04 N for a 3 mm diaphragm. This data is generated from the Timoshenko model. The initial diaphragm tension is assumed to be 0.

Other ways to increase the diaphragm stiffness, especially near the zero deflection point. Using a more flexible membrane material such as Elastomeric Cyclic Olefin Copolymer (E-COC), which has a Young's modulus of 50 MPa compared to 1300-1500 MPa for the COC membrane used in the present designs, can greatly reduce the force required for diaphragm actuation. As shown in FIG. 39, for a 3 mm diameter diaphragm, the force required for the membrane deflection of 0.1 mm is about 0.04 N.

Then, the total force including the force to pressurize the fluid and to deflect the membrane is about 0.2 N. In addition, the actuator will need to overcome the spring element or vacuum which brings the diaphragm back to the neutral position. Assuming symmetric loading in both directions, a total force requirement of 0.4 N is obtained. With a factor of 1.5, for the additional spring deflection, the force requirement from the actuator is 0.6 N, which is less than the present 1 N.

Bounding Calculations for Permanent Magnet and Winding

For a surface with normal magnetic field B, the magnetic stress normal to the surface, acting on a ferromagnetic material to bring the two surfaces close together is given by (Haus, et al., *Electromagnetic Fields and Energy*, Prentice Hall Books (1989)), $$P_{magnetic} = \frac{B^2}{2\mu_0} \qquad \text{Equation 9.1}$$

where, $\mu 0$ is the permeability of free space and equal to $1.257 \times 10^{-6}$ NA$^{-2}$. For a field of 1 T, normal at the surface of a permanent magnet, this stress calculates to Pmagnetic≈0.4 MPa. For 0.6 N of force, the pole face area required is thus 0.6/0.4=1.5 mm$^2$.

Figure 40:
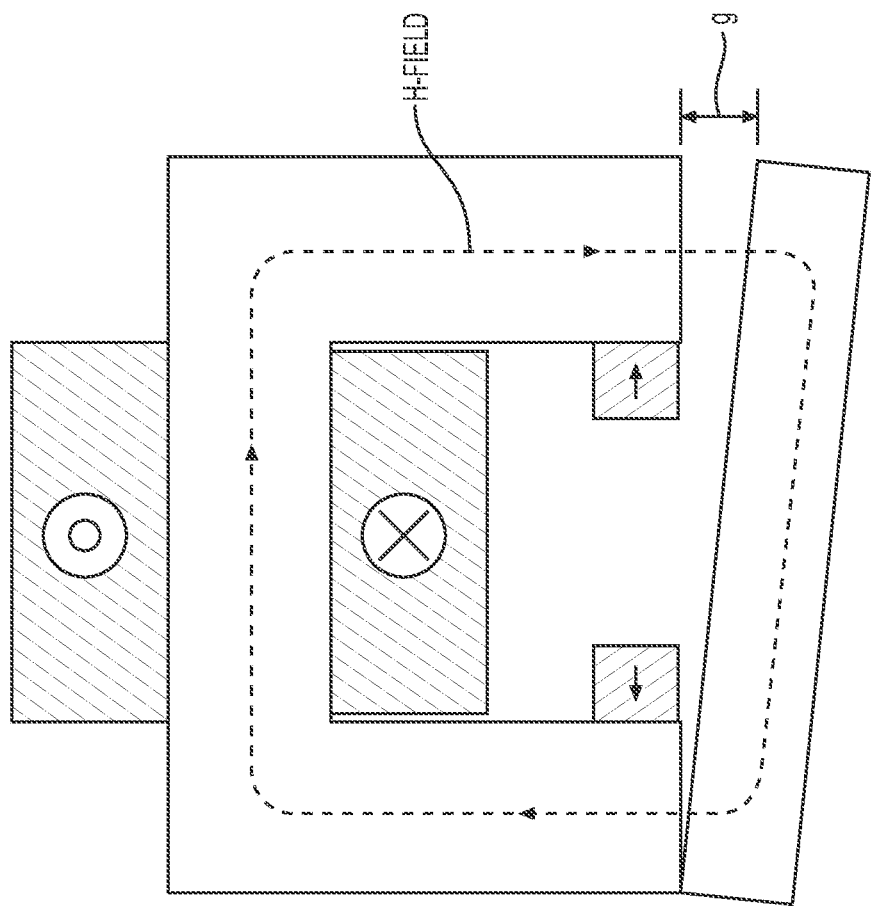
FIG. 40 is a diagram showing a schematic of the actuator to get estimates of the winding area. The rotor is latched to the left pole face. The winding current drives an H-field which counteracts the B-field on the left side pole face causing the rotor to flip. The stator and rotor are assumed to have an infinite permeability. Therefore, the H-field inside them is 0. Most of the H-field in the magnetic circuit is then in the air-gap. The winding area may be found using Ampere's law (Equation 9.2).

The winding magnetic field counteracts this latching B-field from the permanent magnet. FIG. 40 shows a schematic with the rotor latched on the left pole face. Assuming a relative permeability of low carbon steel to be $\mu_r$=1000, and maximum winding current density, $J_{max}$ of 10 A/mm$^2$ for a short pulse, the required winding area can be estimated. For simple estimate, the relative permeability of the low-carbon steel may be assumed to have an infinite permeability compared to the air-gap. Then, the H-field inside the low-carbon steel material (stator and rotor) is negligible and most of the drop in H occurs at the air-gap (g). In the scaled up actuator, an air-gap of 0.4 mm is considered. Assuming the same air-gap, and using Ampere's law (Haus, et al., *Electromagnetic Fields and Energy*, Prentice Hall Books (1989)), $$\oint_C H \cdot dl = \iint_S J \cdot dA. \qquad \text{Equation 9.2}$$

Equation 9.2 can be used to get an estimate of the winding area required. To get a B-field of 1T, the H-field in the air gap should be H=B/$\mu_0$≈800 A/mm. Then, the required coil area is given by, $$A_{coil} = \frac{H \cdot g}{J_{max}} \qquad \text{Equation 9.3}$$

Substituting the values, $A_{coil}$=800×0.4/10=32 mm$^2$. Assuming a coil packing fraction of 0.5, the winding area then becomes $A_{winding}$=64 mm$^2$.

With a B-field of 0.6 T, the magnet area required becomes about 4 mm$^2$ and the winding area $A_{winding}$ becomes about 38 mm$^2$. The total number of Amp-turns is then approximately 200 Amp-turns. One way of reducing the amp-turn requirement is to have a larger area of the stator at the winding and focus that flux with a smaller area at the pole faces. The reduction in area increases the B-field to keep the flux constant, and since the normal force varies quadratically with B-field and linearly with area, the total force at the pole faces should then increase until the B-field within the low-carbon steel saturates.

Design with Reduced Actuator Size

Figure 41A:
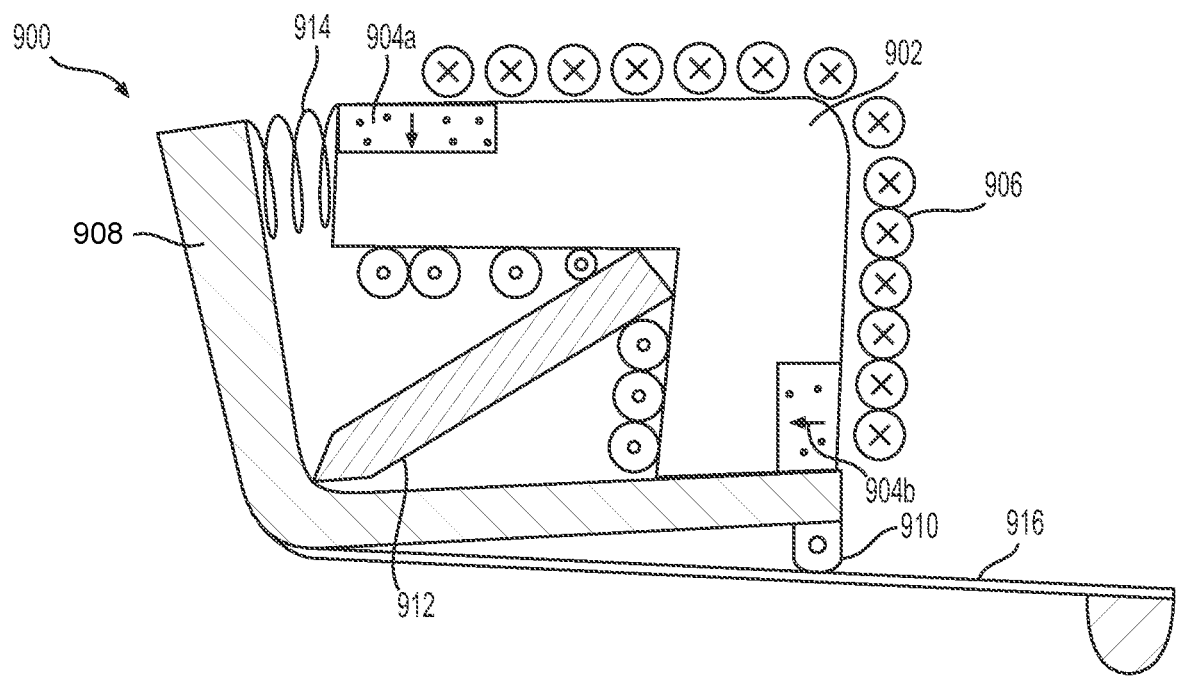
FIGS. 41A and 41B are diagrams showing different embodiments for EM actuators.
Figure 41B:
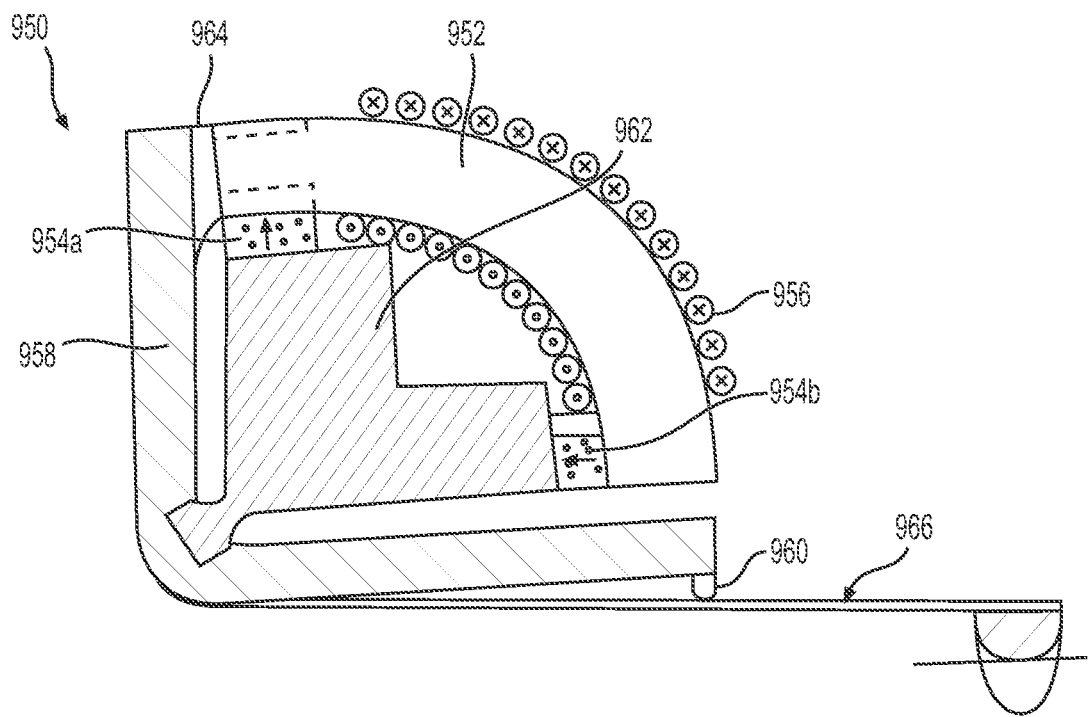

By making the stator smooth and curved, without sharp corners, the coil winding may be simplified. In addition, the actuator may be made more compact by keeping the pusher only on one side and folding the other side of the rotor to have a 90° included angle as shown in FIGS. 41A and 41B. FIG. 41A shows an EM actuator 900 which uses a rigid blade 912 as a pivot (notch flexure), which simplifies the pivot design. The EM actuator 900 includes stator 902, permanent magnets 904a and 904b, winding 906, rotor 908, pusher 910, blade 912, spring 914, and contact spring 916. The radius on the rotor provides the rolling contact. The tension spring (elongated) on top pulls the rotor to the top pole face when the contact spring is not loaded. FIG. 41B shows a different embodiments of a notch flexure. The EM actuator 950 includes stator 952, permanent magnets 954a and 954b, winding 956, rotor 958, pusher 960, notch flexure 962, pole face 964, and contact spring 966. Making the stator without sharp bends makes it easier to wind. The magnet may be embedded within the stator geometry by making a cut-out, to reduce the pole face area compared to the area at the winding, to amplify the B-field. Pusher is only needed on one side to make contact with the membrane. The other side can store energy in a small spring which elongates when the rotor moves away from the pole face. The stator, PM and notch flexure (or pivot blade) can be bonded together.

The pole surface area can be reduced compared to the stator cross-section area at the winding to focus the magnetic flux and therefore amplify the B-field. The approximate dimensions can be about 15-20 mm for each edge of the rotor and the contact spring can be about 30-40 mm. This would give a winding length of about 20 mm (circumference of the quarter circle). Smaller actuators should have a lower inertia and hence exhibit faster dynamics.

Example 10. Vacuum Clamping as an Alternative to a Bonded and Screw Based Clamped Membrane Vacuum Clamping with Membrane-Bonded Top Plates The benefit of vacuum clamping is that it allows for easy assembly of top plates with reusable bottom plates. The bottom plates can use either EM or pneumatic actuators. This has benefit for both membrane-bonded platform 1000 and membrane-clamped platform 2000.

Figure 42A:
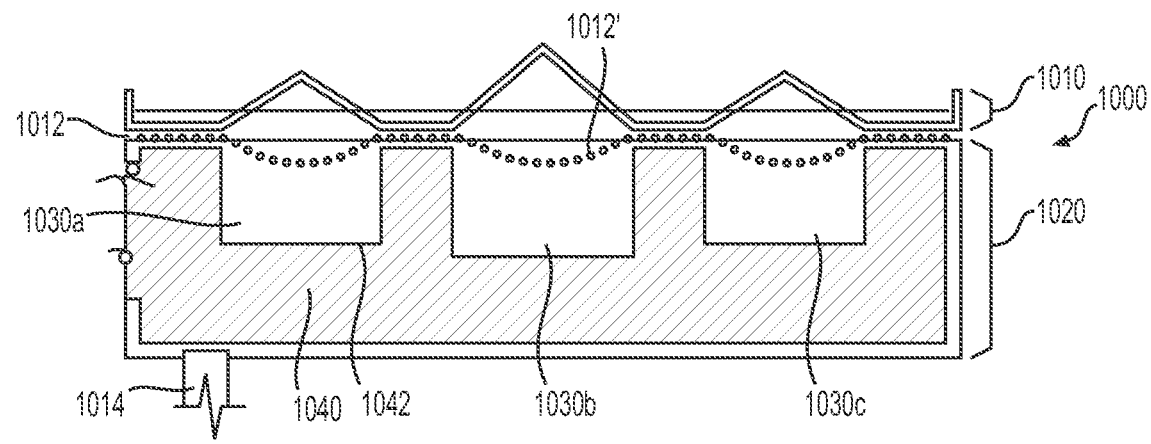
FIGS. 42A-42E are diagrams showing vacuum clamping with membrane-bonded top plates.
Figure 42B:
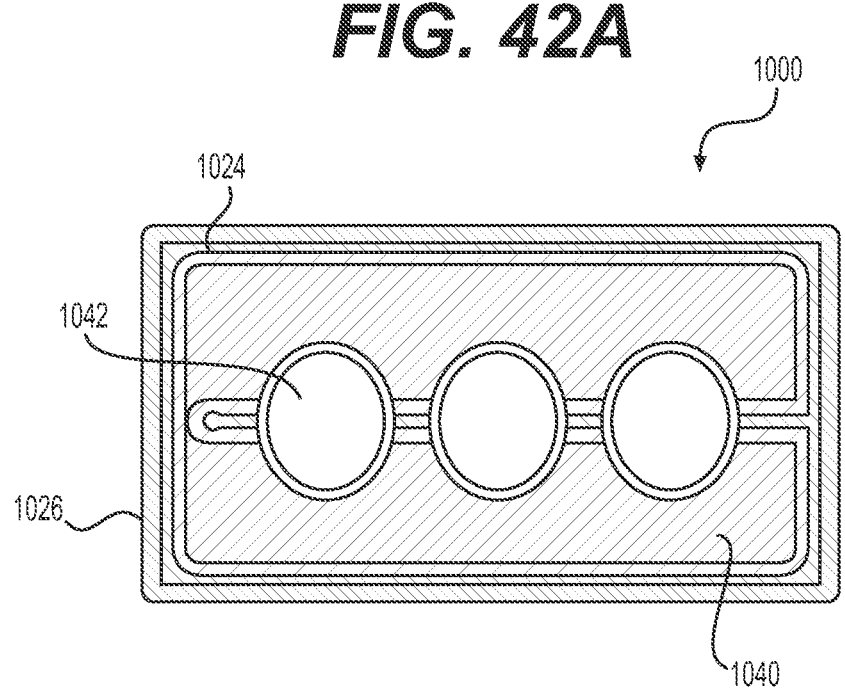

Membrane bonded top plate 1010 may be disposable while the bottom plate 1020 may be reusable. The fluid sealing is achieved by the bonding of the membrane 1012 to the bottom surface of the top plate 1010. The membrane 1012 has free regions 1012' which deflect with the application of the vacuum through the vacuum port 1014 (FIG. 42A)

Figure 42C:
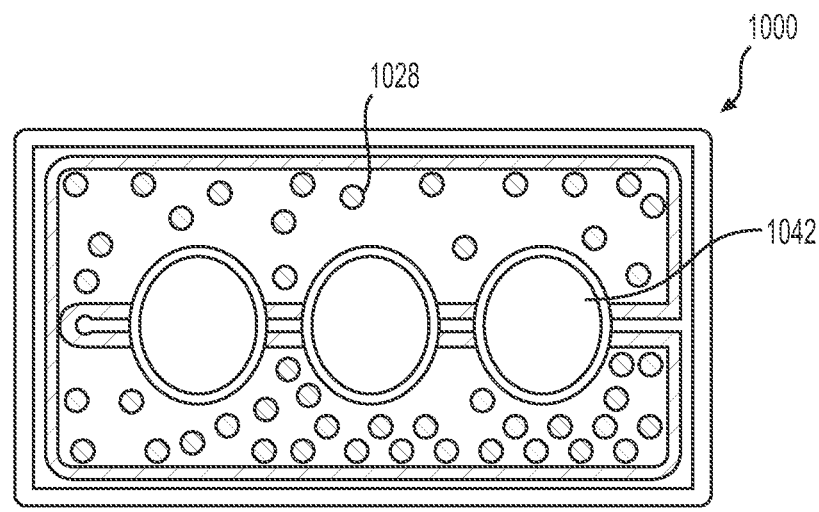
Figure 42D:
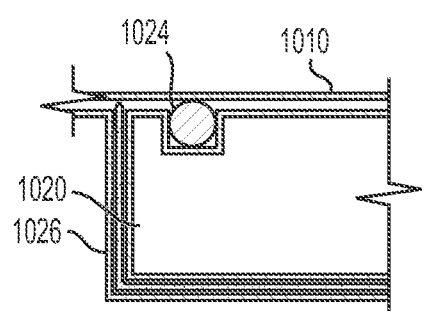
Figure 42E:
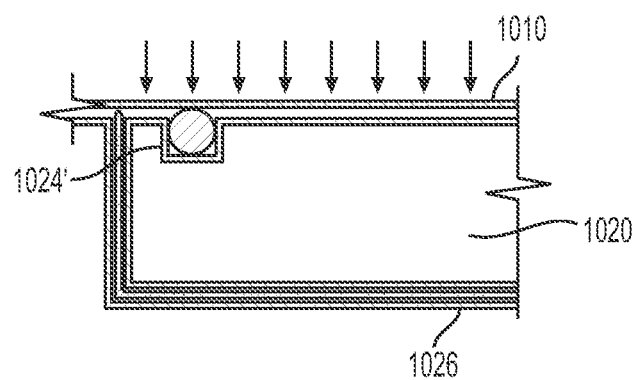

The membrane-clamped platforms eliminate the screws required for clamping. In larger platforms (e.g. 7-way), the number of screws is 72. FIG. 42A is a diagram of vacuum clamping with membrane-bonded top plate 1010. Either a porous stone 1040 (such as graphite, or porous aluminum oxide ($Al_2O_3$)) or a manufactured structure out of solid plastic, metal or composites, such as pillars 1028, may be used to form the bottom plate 1020. The gasket details are:

Porous stones are commonly used for air-bearings for machines such as Coordinate Measuring Machine (CMM). The benefit of porous stone is that the user can get a support surface which also a surface which provides negative air pressure (vacuum) at the pores on the surface. Therefore, the user can have a flat surface with cavities 1042 for the EM actuators 1030a, 1030b, and 1030c, and the pump and valve diaphragm deflections (FIG. 42A). A gasket 1024 around the fluidic features helps seal the vacuum within the system. The porous stones 1040 have a thin film 1026 covering their outer surfaces to help seal the vacuum inside the system. The gasket 1024 may be compressed forming compressed gasket 1024' under the force of the top plate (FIGS. 42D and 42E).

Solid plastic, metal or composites may be used, by vertically raising the clamping and support regions (pillars 1028 in FIG. 42C) and depressing surfaces which expose the top plate to vacuum.

Vacuum Clamping of Clamped Membrane Platforms

Figure 43A:
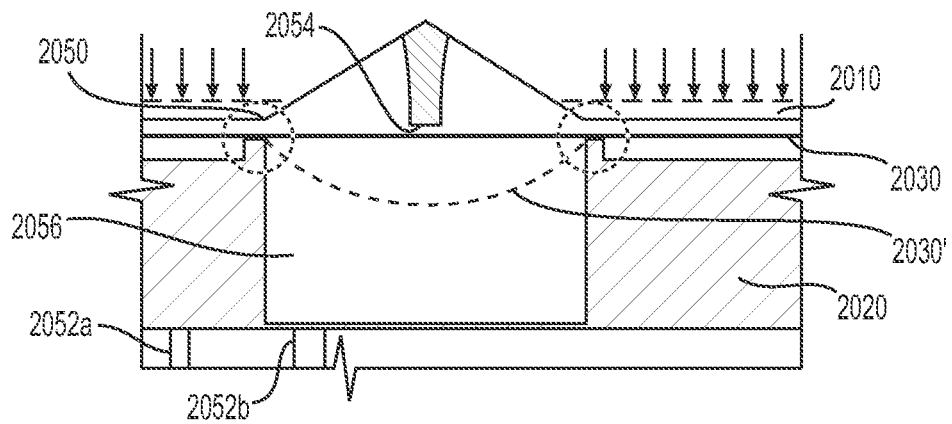
FIGS. 43A-43E are diagrams showing vacuum clamping for clamped membrane platforms.
Figure 43B:
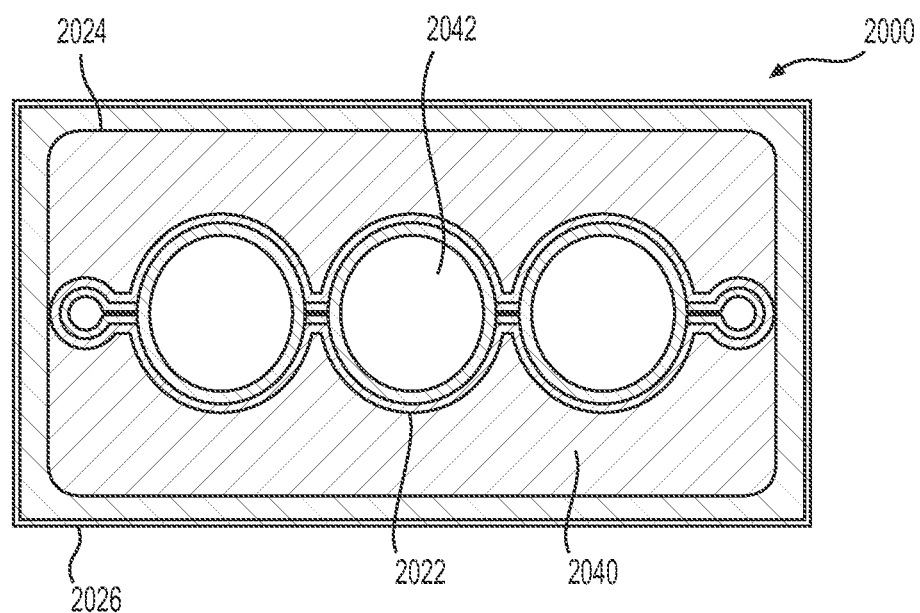
Figure 43C:
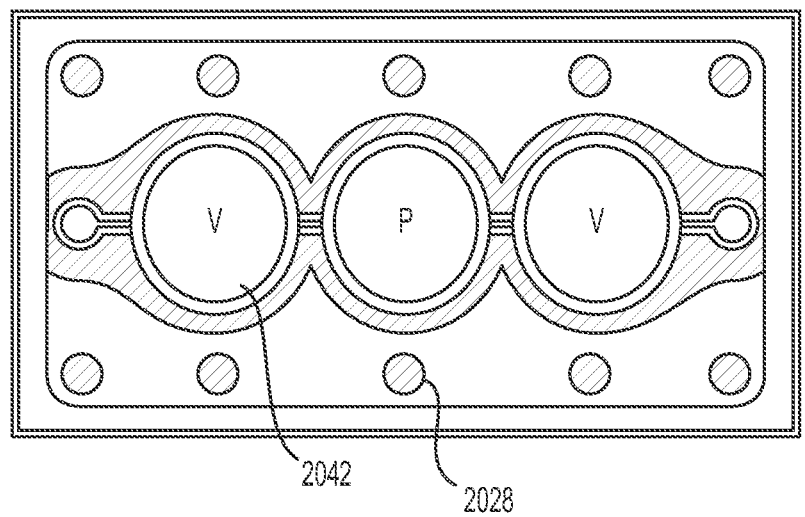

FIGS. 43A-43E are diagrams showing vacuum clamping for clamped membrane platforms. FIG. 43A shows that vacuum clamps the membrane 2030 to the bottom plate 2020, and provides sufficient seal of the membrane 2030 on the boundaries 2050 between the plate and the cavities 2056 for valve chambers and pump chamber. The actuators positioned in the cavities 2056 generate a force sufficient to seal the membrane 2030 to the midwall valve 2054 (or chamber wall, not shown) in the top plate 2010 while overcoming the vacuum needed to create suction on the membrane 2030 outside of valve chamber or pump chamber and also deflect the membrane 2030' and seal the fluid. Vacuum is provided through vacuum ports 2052a and 2052b.

The membrane 2030 is placed between the top plate 2010 and the bottom plate 2020 and are then clamped together using vacuum. In this case, to provide sealing of the fluid, gaskets around the fluid channels and the pump and valve chambers are needed. A custom-cut gasket 2022 may be used at the boundaries for sealing the vacuum inside.

Figure 43D:
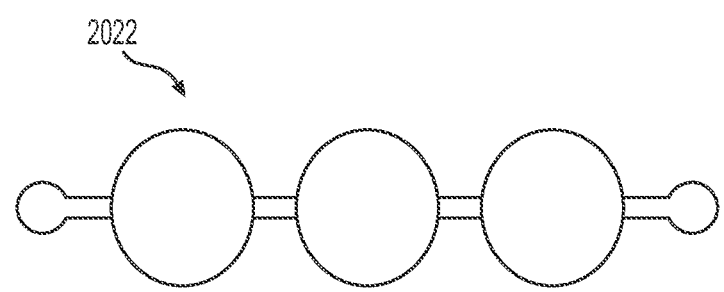
Figure 43E:
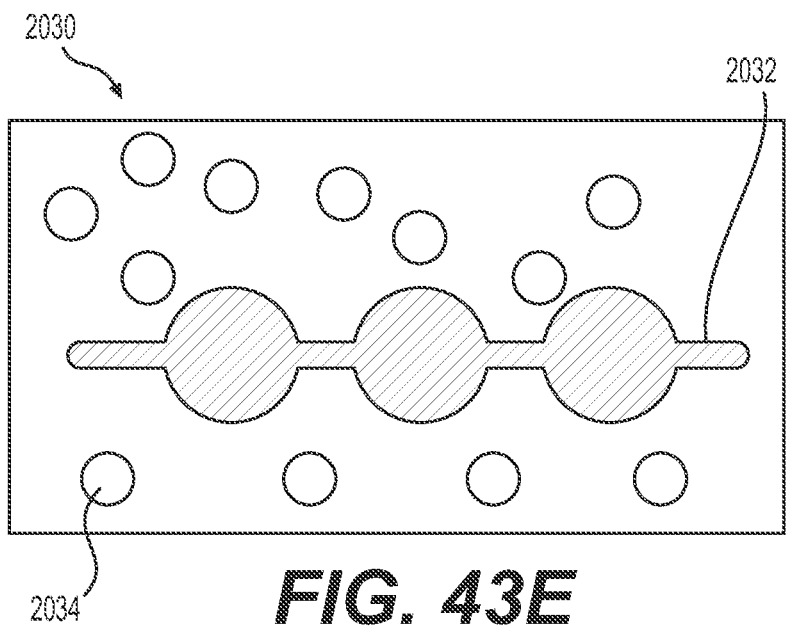

A porous stone 2040 (FIG. 43B) or solid material—plastic or metal, such as pillars 2028 (FIG. 43C) may be used to form the bottom plate. The porous stones 2040 have a thin film 2026 covering their outer surfaces to help seal the vacuum inside the system. The uniform distribution of clamping force over area is from the pillars 2028. The membrane 2030 should have holes 2034 in the region other than the pillars, the raised regions and the pump and valve chamber diaphragm regions 2032 should have no holes (FIG. 43E). These holes provide pathway for vacuum to reach the top plate surface, thereby providing the force due to vacuum which helps in sealing.

At the sealing regions, the membrane and compressed gasket 2022' are used as the deflecting members which seal the membrane 2030 against the top plate 2010 leading to fluidic sealing. The gasket may be compressed forming compressed gasket under the force of the top plate (as shown in FIGS. 43D, 43E). Bottom surface of the membrane and the compressed gasket cause pneumatic sealing.

The vacuum clamping (FIGS. 42A-43E) seals the diaphragm fluidically. The area exposed to vacuum is much larger than the sealing area. Therefore, the pressure at the sealing regions is amplified to provide the required sealing pressures.

This method may be used with both electromagnetic (EM) and pneumatic actuators.

Calculations help to size the various parts of the platform. The area exposed to vacuum for the top plate should be maximized and the clamping area, the actuator force and the sealing force should all be minimized. Using porous stones helps in this aspect, as they have a uniformly distributed exposed area due to the porosity and have a uniformly distributed, and comparatively small clamped area.

The gasket is usually made of an elastomeric material such as silicone rubber, neoprene, VITON® (The Chemours Company Fc, LLC, Wilmington, Del.), butyl, fluoroelastomer, etc. Their stiffness can be modeled using the analysis for rubber bearings presented by Augusto Barton (Barton Martinelli A. E., *Rubber bearings for precision positioning systems,* 2005, MS thesis, MIT). The sealing pressure is the product of deflection of the gasket and the sealing area.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A low power consumption electromagnetic actuator comprising
   a) a stator body comprising at least one set of two protruding legs and a connecting segment connecting the at least one set of two protruding legs and having a vertical and a horizontal axis of symmetry,
   b) at least two permanent magnets attached to the stator body,
   c) a winding coil around the connecting segment,
   d) at least one flexure positioned between at least two pole faces,
   wherein the at least one flexure is formed of a material having a stiffness and a strain range sufficient for permitting rotor rotation or mover movement, formed of a material with a Young's modulus less than the Young's modulus of aluminum, and
   e) a rotor or mover comprising at least two opposing regions, the rotor contacting the at least one flexure, and
   a contact spring connected to the rotor or the mover for transfer to and storage of energy in the contact spring,
   wherein each permanent magnet forms a pole face on the stator body about the site of its attachment and on one end of the flexure and not within a primary magnetic flux path.

2. The actuator of claim 1, wherein the at least one flexure is selected from the group consisting of a blade flexures, notch flexures, wire flexures, torsion flexures, folded flexures, cross-flexures and bushings.

3. The actuator of claim 1, wherein the at least one set of two protruding legs are symmetrical to one another along the horizontal and/or the vertical axis of symmetry.

4. The actuator of claim 1, wherein at least one end of each of the at least one set of two protruding legs cross a plane perpendicular to the vertical axis of symmetry.

5. The actuator of claim 1, wherein the at least two opposing regions of the rotor or the mover comprise a pusher.

6. The actuator of claim 1, wherein the winding coil comprises a coated or uncoated metal wire having gauge of winding wire capable of producing a sufficient number of Amp-turns to generate force sufficient to flip the rotor or move the mover.

7. The actuator of claim 1, wherein the at least one flexure comprises a thin region and a thick region.

8. The actuator of claim 1, wherein the rotor is configured to rotate about the at least one flexure and sequentially latch to each of the at least two pole faces with its at least two opposing regions.

9. The actuator of claim 1, wherein the contact spring further comprises a pushing element selected from the group consisting of a plunger, pin, button, push-button, finger, and pusher.

10. A meso- or micro-scale fluidic device comprising
    a fluidic plate comprising fluidic channels and at least one chamber, and
    a pump block comprising
        a) an actuator comprising
            i) a stator body comprising at least one set of two protruding legs and a connecting segment connecting the at least one set of two protruding legs,
            ii) at least two permanent magnets attached to the stator body,
            iii) winding coil around the connecting segment,
            iv) at least one flexure positioned between at least two pole faces, and
            v) a rotor or mover comprising at least two opposing regions, the rotor or mover contacting the at least one flexure,
        the actuator comprising a contact spring connected to the rotor or the mover for transfer to and storage of energy in the contact spring,
    wherein the at least one chamber in the fluidic plate is positioned in operable proximity to the at least two opposing regions of the rotor or the mover, or to at least one end of the contact spring,
    wherein each permanent magnet forms a pole face on the stator body about the site of its attachment and on one end of the flexure and not within a primary magnetic flux path.

11. The fluidic device of claim 10, wherein the actuator comprises at least one flexure selected from the group consisting of a blade flexures, notch flexures, wire flexures, torsion flexures, folded flexures, cross-flexures and bushings.

12. The fluidic device of claim 10, wherein the at least one set of two protruding legs are symmetrical to one another along a horizontal and/or a vertical axis of symmetry.

13. The fluidic device of claim 10, wherein at least one end of each of the two legs cross a plane perpendicular to the vertical axis of symmetry.

14. The fluidic device of claim 10, wherein the at least two opposing regions of the rotor or the mover comprise a pusher.

15. The fluidic device of claim 10, wherein the winding coil comprises a coated or uncoated metal wire having gauge of winding wire capable of producing a sufficient number of Amp-turns to generate force sufficient to flip the rotor or move the mover.

16. The fluidic device of claim 10, wherein the at least one flexure comprises a thin region and a thick region, and is formed of a material having a stiffness and a strain range sufficient for permitting rotor rotation or mover movement, formed of a material with a Young's modulus less than the Young's modulus of aluminum.

17. The fluidic device of claim 10, wherein the rotor is configured to rotate about the at least one flexure and sequentially latch to each of the at least two pole faces with its at least two opposing regions.

18. The fluidic device of claim 10, wherein the contact spring further comprises a pushing element selected from the group consisting of a plunger, pin, button, push-button, finger, and pusher.

19. The fluidic device of claim 10, wherein the at least two permanent magnets are positioned apart from each other at a distance at least between 2 and 10 times the width of the at least one set of two protruding leg.

20. The fluidic device of claim 10, wherein the connecting segment of the stator body is positioned away from each of the at least two permanent magnets at a distance at least between 2 and 6 times the width of the at least two permanent magnets.

21. The fluidic device of claim 10, wherein the actuator is a low energy consumption actuator.

22. The fluidic device of claim 10, wherein the actuator operates without substantial increase in actuator, pump block, or fluid temperature.

23. The fluidic device of claim 10, comprising a diaphragm positioned between the at least one chamber and the contact spring, wherein the diaphragm is bonded to the fluidic plate by a mechanism selected from the group consisting of adhesive, solvent, thermal, anodic, and/or chemical bonding, clamping, and mechanical clamping, clamping using fluidic pressure, and clamping using vacuum.

24. The fluidic device of claim 10, comprising a diaphragm positioned between the at least one chamber and the contact spring, further comprising a bottom plate, wherein the diaphragm is bonded to the bottom plate by a mechanism selected from the group consisting of adhesive, solvent, thermal, anodic, and chemical bonding, mechanical clamping, clamping using fluidic pressure, and clamping using vacuum.

25. The fluidic device of claim 10, wherein operable proximity comprises a hydraulic bottom plate, having a cap contacting the at least two opposing regions of the rotor or the mover.

26. A method for actuating fluid in a fluidic device comprising contacting the fluid with the contact spring of the actuator of claim 10, by contacting the fluid through a diaphragm.

27. The method of claim 26, wherein the fluid is in a chamber in a fluidic plate of the fluidic device.

28. The method of claim 26, wherein the fluid is in a chamber of a fluidic plate and is separated from the contact spring by the diaphragm.

29. The method of claim 26, wherein portions of the diaphragm are bonded to a fluidic plate of the fluidic device.

30. The method of claim 29, wherein the portions of the diaphragm are bonded by a mechanism selected from the group consisting of adhesive, solvent, thermal, anodic, and chemical bonding, mechanical clamping, clamping using fluidic pressure, and clamping using vacuum.

31. The method of claim 26, wherein the actuator provides a constant, linear, or non-linear force sufficient to deflect the diaphragm against varying fluid back-pressure and to prevent fluid flow.

32. The method of claim 26, wherein the actuator operates with low energy consumption and provides varying displacement stroke with varying back-pressure.

33. The method of claim 26, wherein the actuator operates with low energy consumption and maintains constant displacement stroke with varying back-pressure.

34. The method of claim 26, wherein the actuator operates without substantial increase in actuator or fluid temperature.

35. The method of claim 26, wherein the contact spring is configured to adjust the contact angles when making contact with the diaphragm.

36. The method of claim 26, wherein the contact spring is configured to store sufficient energy while contacting through diaphragm, which is recovered in the opposite stroke of the actuator further reducing energy consumed by the low power consumption actuator.

* * * * *